(12) United States Patent
Yang et al.

(10) Patent No.: US 7,939,059 B2
(45) Date of Patent: May 10, 2011

(54) METHOD FOR THE GENERATION OF ANTIGEN-SPECIFIC LYMPHOCYTES

(75) Inventors: Lili Yang, Pasadena, CA (US); Luk Van Parijs, Cambridge, MA (US); David Baltimore, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 115 days.

(21) Appl. No.: 11/517,814

(22) Filed: Sep. 8, 2006

(65) Prior Publication Data

US 2007/0116690 A1   May 24, 2007

Related U.S. Application Data

(63) Continuation-in-part of application No. 10/789,938, filed on Feb. 27, 2004, now abandoned, which is a continuation-in-part of application No. 10/317,078, filed on Dec. 10, 2002, now abandoned.

(60) Provisional application No. 60/394,803, filed on Jul. 8, 2002, provisional application No. 60/339,375, filed on Dec. 10, 2001.

(51) Int. Cl.
*A61K 48/00* (2006.01)
*C12P 21/06* (2006.01)

(52) U.S. Cl. .................. 424/93.21; 424/93.1; 424/93.2; 435/69.1; 435/69.5; 435/69.7

(58) Field of Classification Search .................. None
See application file for complete search history.

(56) References Cited

U.S. PATENT DOCUMENTS

| | | | | |
|---|---|---|---|---|
| 5,830,755 A | * | 11/1998 | Nishimura et al. | 435/325 |
| 7,041,438 B2 | * | 5/2006 | Carpenter et al. | 435/4 |
| 7,531,648 B2 | * | 5/2009 | Kingsman et al. | 536/23.53 |
| 2005/0238626 A1 | * | 10/2005 | Yang et al. | 424/93.21 |

OTHER PUBLICATIONS

Dietz et al. Cytother 2001;3:97-105.*
Anderson, Hum Gene Ther 2002;13:1261-2.*
Luo et al. Blood 2009;113:1422-31.*
Barnden et al., "Defective TCR expression in transgenic mice constructed using cDNA-based α- and β-chain genes under the control of heterologous regulatory elements," *Immunology and Cell Biology*, vol. 76, (1998), pp. 34-40.
Berg et al., "Expression of T-Cell Receptor Alpha-Chain Genes in Transgenic Mice," *Molecular and Cellular Biology*, vol. 8, No. 12, Dec. 1998, pp. 5459-5469.
Berger et al. "Adoptive Transfer of Virus-Specific and Tumor-Specific T Cell Immunity," *Curr. Opin. Immunol.* vol. 21, No. 2, 2009, pp. 224-232.
Blüthmann et al., T-cell-specific deletion of T-cell receptor transgenes allows functional rearrangement of endogenous α- and β-genes, *Nature*, vol. 334, Jul. 14, 1988, pp. 156-159.
Clay et al., "Efficient transfer of a tumor antigen-reactive TCR to human peripheral blood lymphocytes confers anti-tumor reactivity," *Journal of Immunology* vol. 163, No. 1 pp. 507-513 (Jul. 1, 1999).
Clay et al., "Potential use of T cell receptor genes to modify hematopoietic stem cells for the gene therapy of cancer," *Pathology Oncology Research*, vol. 5, pp. 3-15 (1999).
Cooper et al., "Transfer of specificity for human immunodeficiency virus type 1 into primary human T lymphocytes by introduction of T-cell receptor genes," *Journal of Virology*, vol. 74, pp. 8207-8212 (2000).
Déglon et al., "Self-Inactivating Lentiviral Vectors with Enhanced Transgene Expression as Potential Gene Transfer System in Parkinson's Disease," *Human Gene Therapy*, vol. 11, Jan. 1, 2000, pp. 179-190.
Dembićet al., "Transfer of specificity by murine α and β T-cell receptor genes," *Nature*, vol. 320, Mar. 20, 1986, pp. 232-238.
Dong et al, *J. Experim. Med.* 200 (12), pp. 1547-1557 (2004).
Dudley et al., "Cancer Regression and Autoimmunity in Patients After Clonal Repopulation with Antitumor Lymphocytes," *Science*, vol. 298, Oct. 25, 2002, pp. 850-854.
Dull et al., "A Third-Generation Lentivirus Vector with a Conditional Packaging Sysyem," *Journal of Virology*, vol. 72, No. 11, Nov. 1998, pp. 8463-8471.
Finney et al., "Chimeric receptors providing both primary and costimulatory signaling in T cells from a single gene product," *Journal of Immunology*, vol. 161, pp. 2791-2797 (1998).
French Anderson, *Hum Gene Ther* 13:1261-2 (2002).
Fujio et al., "Functional Reconstitution of Class II MHC-Restricted T Cell Immunity Mediated by Retroviral Transfer of the αβ TCR Complex," *J. Immunology*, vol. 165, (2000), pp. 528-532. Hozumi et al., "Establishment of efficient reaggregation culture system for gene tarnsfection into immature T cells by retroviral vectors," *Immunology Letters*, vol. 71, No. 1, pp. 61-66 (Jan. 10, 2000).
Kessels et al., "Immunotherapy through TCR gene transfer," *Nature Immunology*, vol. 2, No. 10, pp. 957-961 (Oct. 2001).
Kouskoff et al., "Cassette vectors directing expression of T cell receptor genes in transgenic mice," *Journal of Immunological Methods*, vol. 180, (1995), pp. 273-280.

(Continued)

*Primary Examiner* — Q. Janice Li
(74) *Attorney, Agent, or Firm* — Knobbe, Martens, Olson & Bear LLP

(57) ABSTRACT

The invention provides systems and methods for the generation of lymphocytes having a unique antigen specificity. In a preferred embodiment, the invention provides methods of virally infecting cells from bone marrow with one or more viral vectors that encode antigen-specific antibodies for the production of, for example B cells and T cells. In some embodiments, the viral vectors include an IRES or 2A element to promote separation of, for example, the α subunit and β subunit of a T cell receptor (TCR) or heavy and light chains of a B-cell antibody. The resulting lymphocytes, express the particular antibody that was introduced in the case of B cells and TCR in the case of T cells. The lymphocytes generated can be used for a variety of therapeutic purposes including the treatment of various cancers and the generation of a desired immune response to viruses and other pathogens. The resulting cells develop normally and respond to antigen both in vitro and in vivo. We also show that it is possible to modify the function of lymphocytes by using stem cells from different genetic backgrounds. Thus our system constitutes a powerful tool to generate desired lymphocyte populations both for research and therapy. Future applications of this technology may include treatments for infectious diseases, such as HIV/AIDS, cancer therapy, allergy, and autoimmune disease.

16 Claims, 26 Drawing Sheets

OTHER PUBLICATIONS

Lois et al., "Germline Transmission and Tissue-Specific Expression of Transgenes Delivered by Lentiviral Vectors," *Science*, vol. 295, Feb. 1, 2002, pp. 868-872.

Mamalaki et al., "Positive and Negative Selection in Transgenic Mice Expressing a T-Cell Receptor Specific for Influenza Nucleoprotein and Endogenous Superantigen," *Developmental Immunology*, vol. 3, (1993), pp. 159-174.

May et al. "Therapeutic haemoglobin synthesis in beta-0thalassaemic mice expressing lentivirus-encoded human beta-globulin," *Nature*, vol. 406, pp. 82-86 (Jul. 6, 2000).

Mhashilkar et al., "Inhibition of human immunodeficiency virus type I replication in vitro in acutely and persistently infected human CD4+ mononuclear cells expressing murine and humanized anti-human immunodeficiency virus type 1 TAT single-chain variable fragment intrabodies," *Human Gene Therapy*, vol. 10, pp. 1453-1467 (1999).

Moss, Paul A.H., "Redirecting T cell specificity by TCR gene transfer," *Nature Immunology*, vol. 2, No. 10, Oct. 2001, pp. 900-901.

Orkin et al., *NIH Report*, (Dec. 1995).

Pandya et al., "Lentivirus and foamy virus vectors: novel gene therapy tools," *Expert Opinion on Biological Therapy*, vol. 1, pp. 17-40 (2001).

Patterson, "Statement of Amy Patterson, M.D.," (Feb. 2000).

Pircher et al., "Tolerance induction in double specific T-cell receptor transgenic mice varies with antigen," *Nature*, vol. 342, Nov. 30. 1989, pp. 559-561.

Pogulis et al., "Retroviral-mediated expression of an MHC class I-restricted T cell receptor in the CD8 T cell compartment of bone marrow-reconstituted mice," *Human Gene Therapy*, vol. 9, pp. 2285-2297 (1998).

Robbins et al., "Consistent, persistent, expression from modified retroviral vectors in murine hematopoietic stem cells," *Proceedings of the National Academy of Sciences of the United States of America*, vol. 95, pp. 10182-10187 (Aug. 1998).

Robbins et al., "Viral vectors for gene therapy," *Pharmacol. Ther.* vol. 80, No. 1, pp. 35-47 (1998).

Rosenburg, "Progress in human tumor immunology and immunotherapy," *Nature* vol. 411, pp. 380-384 (2001).

Stanislawski et al., "Circumventing tolerance to a human MDM2-derived tumor antigen by TCR gene transfer," *Nature Immunology*, vol. 2, No. 10, pp. 926-970 (Oct. 10, 2001).

Uematsu et al., "In Transgenic Mice the Introduced Functional T Cell Receptor β Gene Prevents Expression of Endogenous β Genes," *Cell*, vol. 52, Mar. 25, 1998, pp. 831-841.

Van Parijs et al., "Uncoupling IL-2 Signals that Regulate T Cell Proliferation, Survival, and Fas-Mediated Activation-Induced Cell Death," *Immunity*, vol. 11, Sep. 1999, pp. 281-288.

Yang et al., "Generation of functional antigen-specific T cells in defined genetic backgrounds by retrovirus-mediated expression of TCR cDNAs in hematopoietic precursor cells," *Proceedings of the National Academy of Sciences of the United States of America*, vol. 99, No. 9, pp. 6204-6209 (Apr. 30, 2002).

Yang et al., *PNAS*, 102:12, pp. 4518-4523 (2005).

Yee et al., *PNAS*, 99 (25) pp. 16168-16173 (2002).

Yee, C. et al., "Adoptive T cell therapy using antigen-specific CD8+ T cell clones for the treatment of patients with metastatic melanoma: In vivo persistence, migration, and antitumor effect of transferred T cells," *PNAS Early Edition*, www.pnas.org/cgi/doi/10.1073/pnas. 242600099, (2002), pp. 1-6.

Yee, J. et al., "Generation of High-Titer Pseudotyped Retroviral Vectors with Very Broad Host Range," *Methods in Cell Biology*, vol. 43, (1994), pp. 99-112.

Zufferey et al., "Woodchuck Hepatitis Virus Posttranscriptional Regulatory Element Enhances Expression of Trangenes Delivered by Retroviral Vectors," *Journal of Virology*, vol. 73, No. 4, Apr. 1999, pp. 2886-2892.

PCT International Search Report, PCT/US02/39527, mailed Dec. 24, 2003.

\* cited by examiner (SEQ ID NO: 1)

MIG retrovirus construct sequence tgaaagaccccacctgtaggtttggcaagctagcttaagtaacgccattttgcaagcatgaaatacatactgagaatagagaagttcagatcaaggttaggaacagagag
acagcagaatatgggccaaacagtatctgtgtaagcagcagtcctgccccagatgccaagcacgtccccagatgccctcagcagtttcagagaaac
catcagatgtttcaggtgcccaagacccgtgccttatttgaactaaccaatcagtccgcttctcgcttctgttcgcgcttctgctcccgagctca
ataaaagaccccacaacccccactggcgccagtcctccgagactgactgcccagtcctccgtattccacccgagattggaggtccacccgcctgttgcatccgaatcgtggactc
gctgatccttggagggtctcctcagattgactgcgtcgtttcgtgcgttgtgccgcatctaatgtttgcgcctggtctgctgtactagttagctaactagctctgt
ccgggagtaagctggaccggtgtgaactgacgagttctcgaacaccgggccgcaacccctggagacgtcccaggacctttggggccgttttgtggcccgacctgaggaagtcg
atctggaatccgaccgtcaaggatatgtttctgttctggtctgtttcgtctgactgtgttctgtatttgtctgaaaataggcgcagatgtaccactcccttaagtttgaccttaggt
tgtctgctgcagcgctgcagcacgttctgtgtgtttctcagcaaccagtcgtagatgtcaagaagagacgttgggttacctctgtctgcagaatgccaacctaacgtcgatgccgca
cactggaaagatgtcgagcggatcgtcacaaccagtcgtaagatcaagtctttcacccgcctctcgtgtaggcgttggctcgacgtttaaaacgacggcgcaaagttctttcagccgcgcaaaccctttaacgcgcctctctctgatcc
gacgcacttaaccgagacctcgagcggatcgtcacaaccagtcgtaagatcaagtctttcacccgcctctcgtgtaggcgttggctcgacgtttaaaacgacggcgcaaagttctttcagccgcgcaaaccctttaacgcgcctctctctgatcc
tttgaccccccctcctgggcctcactcctctgtacacccgtaaccagatctctctaggcgccgagatctctgagacgttactcatatgttatttcaccacatattgcgtctcttgcaatgtgaggcgcgaaactg
tccctttatcgcctaacgttcagcaacccgagtcgtcactggcgagagcttcctaagggtcttttcccctctcagccgagatctcgttggccctacttgcccctggactctgctggggggctgcgctatcccccccgagacccagttgcctctgcggcaaagcgaacacgtgataaagctcgtcgtgaaggaagcagtcctctgaagcttctgaagacaaa
cccctgtcttcttgacgacccctttcaggcagccgagaaagagtcaaatggctctctccccaccctgtctctcctcaagcgtctaggccccccacccgagctcgagtcgagctccgatcctggtcgagcgtgacgcgaagtcgacgtgacaaaggacggcgggccgagggcgagggcgagcgcatgcgactaccccgaccca
gcaagctgcctgaagttcacacgcaggaaggctcctgcccatcctggtcgcgactccgagctcgagtcgagctccgatcctggtcgagcgtgacgcgaagtcgacgtgacaaaggacggcgggccgagggcgagggcgagcgcatgcgactaccccgacca
gcaagctgcctgaagttcacacgcaggaaggctcctgcccatcctggtcgcgactccgagctcgagtcgagctccgatcctggtcgagcgtgacgcgaagtcgacgtgacaaaggacggcgggccgagggcgagggcgagcgcatgcgactaccccgacca
tgaagcagcacgactctcttcaagccgcatgccgaaggcgatcgagctcgagtcgacgtccgaaggctgacttcaaggaggacaacatccggggcacaacaaggacgcacaacaaccctaccgagaactcaacagccacagaacacccccatgcgacggcc
ggcgacaagcagagaagaacggcatcaagagcgccaactgagcggtcgccgagctcgagctcgagcgccagctcctgctgcgagacatcaagagaggagcgagacaaccagaggagcggtgcagctcgcggatcgtcaacagaacaccccatggacggcc
ccgtgctgctgcccgacaaccagctgccgacgagctcgcctacaagtaagctgaccgtgcagctgagctgaccccggtcatatgatttatttagtctccagaaaaggggggaatgaaagaccccaccctgta
ctctactcggcgcgcgcgctaagcttacggccatgctgcccggggtcttcagtatgagctaactcacctattaattgcggttagctcgctcactgaggccgggcgaccaaaggtcgctgttcctcgttcctgctcgctgttccgccgtatattcacacaacatacgagctcgagctcgagctcgagctcgagctcggtcgcc
tcctggatccgcgcgcgctaagcttacggccatgctgcccggggtcttcagtatgagctaactcacctattaattgcggttagctcgctcactgaggccgggcgaccaaaggtcgctgttcctcgttcctgctcgctgttccgccgtatattcacacaacatacgagctcgagctcgagctcgagctcgagctcggtcgccccgagcagctgacctcgatcgctcgagctcgagctcgagctcgagctcgagctcggtcgccccgagcagctgacctcgatcgct
cggaagcataaagtgtaaagcctggggtgcctaatgagtgagctaactcacctattaattgcgttgcgctcactgcccgctttccagtcgggaaacctgtcgtgccagctgcattaatgaatcggccaacgcgcggggagaggcggtttgcgtattgggcgct
aatgaatcggccaacgcgcggggagaggcggtttgcgtattgggcgctcttccgcttcctcgctcactgactcgctgcgctcggtcgttcggctgcggcgagcggtatcagctcactcaaaggcggtaatacggttatccacagaatcaggggataacgcaggaaagaacatgtgagcaaaaggccagcaaaaggccaggaaccgtaaaaaggccgcgttgctggcgt
actcaaaggcggtaatacggttatccacagaatcaggggataacgcaggaaagaacatgtgagcaaaaggccagcaaaaggccaggaaccgtaaaaaggccgcgttgctggcgt

FIG. 5A

```
ttttccataggctccgcgcccctgacgagcatcacaaaatcgacgctcaagtcagaggtggcgaaacccgacaggactataaagataccaggcgtttccccctgaagctccc
tcgtgcgctcctgttccgaccctgccgcttaccggatacctgtccgcttctccccttgagccttctcatagctcacgctgtaggtatctcagttcggtgt
agtcgttcgctccaagctgggctgtgtgcacgaaccccccgttcagccgcctaatctcgtcttgagtccactagtcttgaaggacagtatttgta
cactgcagcagccactggtaacagattagcagagagcgaggtatgtgtagcgtgctaactacgtctctttgatcggcaaacaaacccgctagtacccgcagattacgc
tctgcgctctgctgaagcagtctcaagaagatcctttgatcttctacgggtctgacgctcagtcagtgaacgaaaactcacgtgtaggatttgtcatgaaagcagattatcaaaaggatct
gcagaaaaaggatccttttaaattaaaaatgaagtttttaaatcaatctaaagtatataacttgtctgacagttaccatgcttaatcagtgaggcacctatctcagcga
tctgtctattcgttcatccagatttatcagcaataatagttgccattgctgccgcttcatcgcgtctacagccacccggtccagtgctgcaactacgataacggcgcagaaggccgagcgcagaaagtggctcctgcaactctcctatttatcgcctcgtttcattcagctccgttccaacgat
cacccggctccagattttatcagcaataatagttgccattgctgccgcttcatcgcgtctacagccacccggtccagtgctgcaactctcctatttatcgcctcgtttcattcagctccgttccaacgat
gagtaagtagttcgccagtttaatagtttgcgcaacaaccggcaagcgttgtgcaacaaaagcggttagctcctccgtgttgtgcaaaaaagcggttagctcctccgtcatcgtcagaagtaagttggccgcagtgttatcactcatggttatggcag
caaggcgagttacatgatcccccatgttgtgcaaaaaagcggttagctcctccgtcatcgtcagaagtaagttggccgcagtgttatcactcatggttatggcag
cactgcataattctcttactgtccatccgtaagatgcttttctgtgactactcaacaagtcattctgagaatagtgtatgcggcgaccgagttgctcttgcc
cggcataacgggatataccgtccaccaactctcttcaggatctcatcattgaaaacgttcttcgggtcaaaaacaggaagcaaaaatgccgcaaaaaaggaatagg
gttcgatgtaaccactgttgaatactcatactctccctgcacccaactctcttcaggatcttcaatattattgaaagcattatgaagcatcatgaaaaccattattatcatgacattaaccctatcacgaggccgtcagcgtc
cgattttcggtgatgacgtgaaacctctgacagcaggtgacagatcagcggtatttactgagagttgtcaccatattgcgggcgaaataccgttaagcggatgcggatccttgtctgtcgagccatatgcgtaagcgggatgagccgagcagaggagagacaacaagccgtcagggccgtcagcgg
gtgttggcgggtgtcgggctggcttaactatggcgggctgcgcaacgacgttgaaatacccacagattgtactgagagtgcaccataccagcagatt
tcaggcgccattcagccgccattttcccagtcctgctccggcctcttcgctattacgccagctggcgaaagggatgtgctgcaaggcgatt
gggtaacgccagggttttcccagtcacgacgttgtaaaacgacggccagtgccaagctttaaaacgacgttgtaaaagcagcgcccaacagtcccccccccccccacgcacccagttcgagcagttgtgcaaggcgttg
agcaccgccgccgcaaggaatggtgcatgcaaggagatgcggcagatcccaacagtccccggcctgcccaaccgcgcgcaagcctgaaacaagcgctcatgagcagttgtgcaaggcgttg
cgagcccgatcttccccatcggtgatgtcggcgatataggcgccagcaaccgcacctgtggcgccggtgatgccgacgatgcgtccggcgtagag
```

FIG. 5B

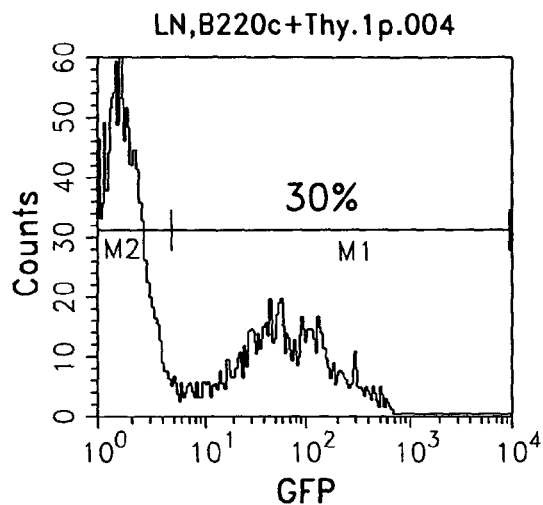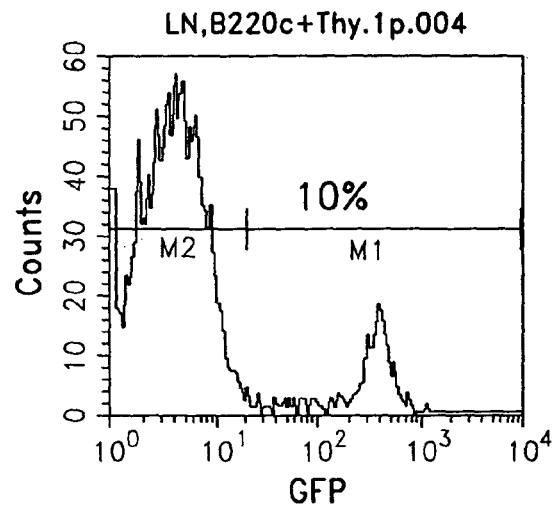
*FIG. 12A*
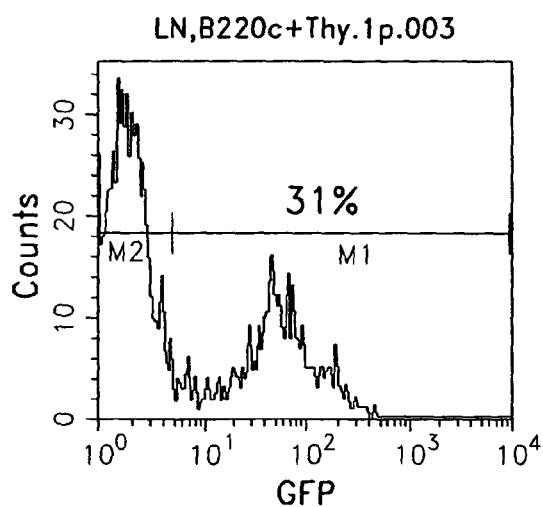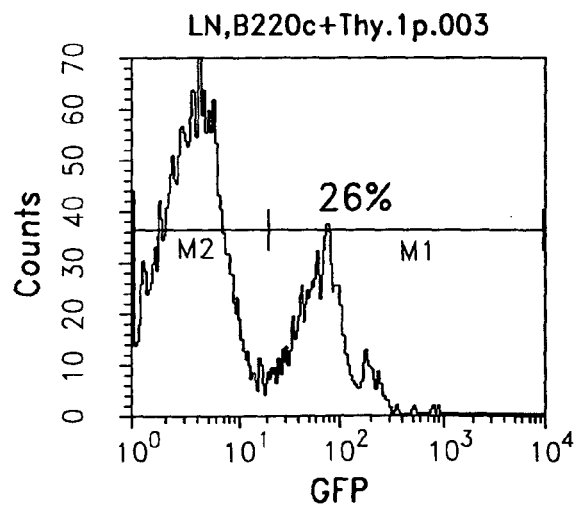
*FIG. 12B*

| | | | |
|---|---|---|---|
| F2A | VKQTLNFDLLKLAGDVESNPG | P | SEQ ID NO: 6 |
| E2A | QCTNYALLKLAGDVESNPG | P | SEQ ID NO: 7 |
| T2A | EGRGSLLTCGDVEENPG | P | SEQ ID NO: 8 |
| P2A | ATNFSLLKQAGDVEENPG | P | SEQ ID NO: 9 |

2A-mediated 'Cleavage'

FIG. 13B

F: foot-and-mouth disease virus
E: equine rhinitis A virus
T: Thosea asigna virus
P: porcine teschovirus-1

SEQUENCE LISTING

<160> NUMBER OF SEQ ID NOS: 14

<210> SEQ ID NO 1
<211> LENGTH: 6254
<212> TYPE: DNA
<213> ORGANISM: Artificial Sequence
<220> FEATURE:
<223> OTHER INFORMATION: This represents a retroviral vector derived
      from the murine stem cell virus

<400> SEQUENCE: 1

```
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaaatgacc ctgtgcctta tttgaactaa ccaatcagtt     300
cgcttctcgc ttctgttcgc gcgcttctgc tccccgagct caataaaaga gcccacaacc     360
cctcactcgg cgcgccagtc ctccgataga ctgcgtcgcc cgggtacccg tattcccaat     420
aaagcctctt gctgtttgca tccgaatcgt ggactcgctg atccttggga gggtctcctc     480
agattgattg actgcccacc tcgggggtct ttcatttgga ggttccaccg agatttggag     540 accctgcct agggaccacc gacccccccg ccgggaggta agctggccag cggtcgtttc     600
gtgtctgtct ctgtctttgt gcgtgtttgt gccggcatct aatgtttgcg cctgcgtctg     660
tactagttag ctaactagct ctgtatctgg cggacccgtg gtggaactga cgagttctga     720
acacccggcc gcaaccctgg gagacgtccc agggactttg ggggccgttt ttgtggcccg     780
acctgaggaa gggagtcgat gtggaatccg accccgtcag gatatgtggt tctggtagga     840
gacgagaacc taaaacagtt cccgcctccg tctgaatttt tgctttcggt ttggaaccga     900
agccgcgcgt cttgtctgct gcagcgctgc agcatcgttc tgtgttgtct ctgtctgact     960
gtgtttctgt atttgtctga aaattagggc cagactgtta ccactccctt aagtttgacc    1020
ttaggtcact ggaaagatgt cgagcggatc gctcacaacc agtcggtaga tgtcaagaag    1080
agacgttggg ttaccttctg ctctgcagaa tggccaacct taacgtcgg atggccgcga     1140 gacggcacct ttaaccgaga cctcatcacc caggttaaga tcaaggtctt ttcacctggc    1200
ccgcatggac acccagacca ggtccccta atcgtgacct gggaagcctt ggcttttgac    1260 cccctccct gggtcaagcc ctttgtacac cctaagcctc cgcctcctct tcctccatcc    1320
gccccgtctc tccccttga acctcctcgt tcgaccccgc ctcgatcctc cctttatcca    1380
gccctcactc cttctctagg cgccgagatc tctcgaggac gttaacgcag tttaaacgac    1440
gcggccgcgc aaagcttgac gaattccgcc cctctccctc cccccccct aacgttactg    1500 gccgaagccg cttggaataa ggccggtgtg cgtttgtcta tatgttattt tccaccatat    1560
tgccgtcttt tggcaatgtg agggcccgga aacctggccc tgtcttcttg acgagcattc    1620
ctaggggtct ttcccctctc gccaaaggaa tgcaaggtct gttgaatgtc gtgaaggaag    1680
cagttcctct ggaagcttct tgaagacaaa caacgtctgt agcgaccctt gcaggcagc    1740 ggaaccccc acctggcgac aggtgcctct gcggccaaaa gccacgtgta taagatacac    1800
ctgcaaaggc ggcacaaccc cagtgccacg ttgtgagttg gatagttgtg gaaagagtca    1860
aatggctctc ctcaagcgta ttcaacaagg ggctgaagga tgcccagaag gtaccccatt    1920
gtatgggatc tgatctgggg cctcggtgca catgctttac atgtgtttag tcgaggttaa    1980
```

```
aaaacgtcta ggccccccga accacgggga cgtggttttc ctttgaaaaa cacgatgata    2040
atatggccac aaccaagggc gaggagctgt tcaccggggt ggtgcccatc ctggtcgagc    2100
tggacggcga cgtgaacggc cacaagttca gcgtgtccgg cgagggcgag ggcgatgcca    2160
cctacggcaa gctgaccctg aagttcatct gcaccaccgg caagctgccc gtgccctggc    2220
ccaccctcgt gaccaccctg acctacggcg tgcagtgctt cagccgctac cccgaccaca    2280
tgaagcagca cgacttcttc aagtccgcca tgcccgaagg ctacgtccag gagcgcacca    2340
tcttcttcaa ggacgacggc aactacaaga cccgcgccga ggtgaagttc gagggcgaca    2400
ccctggtgaa ccgcatcgag ctgaagggca tcgacttcaa ggaggacggc aacatcctgg    2460
ggcacaagct ggagtacaac tacaacagcc acaacgtcta tatcatggcc gacaagcaga    2520
agaacggcat caagcgcaac ttcaagatcc gccacaacat cgaggacggc agcgtgcagc    2580
tcgccgacca ctaccagcag aacacccca tcggcgacgg ccccgtgctg ctgcccgaca    2640
accactacct gagcacccag tccgcccctga gcaaagaccc caacgagaag cgcgatcaca    2700
tggtcctgct ggagttcgtg accgccgccg ggatcactca cggcatggac gagctgtaca    2760
agtaagtcga cctgcagcca agcttatcga taaaataaaa gattttattt agtctccaga    2820
aaaagggggg aatgaaagac cccacctgta ggtttggcaa gctagcttaa gtaacgccat    2880
tttgcaaggc atggaaaata cataactgag aatagaaag ttcagatcaa ggttaggaac    2940
agagagacag cagaatatgg gccaaacagg atatctgtgg taagcagttc ctgccccggc    3000
tcagggccaa gaacagatgg tccccagatg cggtcccgcc ctcagcagtt tctagagaac    3060
catcagatgt ttccagggtg ccccaaggac ctgaaaatga ccctgtgcct tatttgaact    3120
aaccaatcag ttcgcttctc gcttctgttc gcgcgcttct gctccccgag ctcaataaaa    3180
gagcccacaa cccctcactc ggcgcgccag tcctccgata gactgcgtcg cccgggtacc    3240
cgtgtatcca ataaaccctc ttgcagttgc atccgacttg tggtctcgct gttccttggg    3300
agggtctcct ctgagtgatt gactacccgt cagcggggt cttt cagtat tcgtaatcat    3360 ggtcatagct gtttcctgtg tgaaattgtt atccgctcac aattccacac aacatacgag    3420
ccggaagcat aaagtgtaaa gcctggggtg cctaatgagt gagctaactc acattaattg    3480
cgttgcgctc actgcccgct ttccagtcgg gaaacctgtc gtgccagctg cattaatgaa    3540
tcggccaacg cgcggggaga ggcggtttgc gtattgggcg ctcttccgct tcctcgctca    3600
ctgactcgct gcgctcggtc gttcggctgc ggcgagcggt atcagctcac tcaaaggcgg    3660
taatacggtt atccacagaa tcaggggata acgcaggaaa gaacatgtga gcaaaaggcc    3720
agcaaaaggc caggaaccgt aaaaaggccg cgttgctggc gtttttccat aggctccgcc    3780
cccctgacga gcatcacaaa aatcgacgct caagtcagag gtggcgaaac ccgacaggac    3840
tataaagata ccaggcgttt ccccctggaa gctccctcgt gcgctctcct gttccgaccc    3900
tgccgcttac cggatacctg tccgcctttc tcccttcggg aagcgtggcg ctttctcata    3960
gctcacgctg taggtatctc agttcggtgt aggtcgttcg ctccaagctg ggctgtgtgc    4020 acgaacccc cgttcagccc gaccgctgcg ccttatccgg taactatcgt cttgagtcca    4080
acccggtaag acacgactta tcgccactgg cagcagccac tggtaacagg attagcagag    4140
cgaggtatgt aggcggtgct acagagttct tgaagtggtg gcctaactac ggctacacta    4200
gaaggacagt atttggtatc tgcgctctgc tgaagccagt taccttcgga aaaagagttg    4260
gtagctcttg atccggcaaa caaaccaccg ctggtagcgg tggttttttt gtttgcaagc    4320
agcagattac gcgcagaaaa aaaggatctc aagaagatcc tttgatcttt tctacggggt    4380
```

```
ctgacgctca gtggaacgaa aactcacgtt aagggatttt ggtcatgaga ttatcaaaaa    4440
ggatcttcac ctagatcctt ttaaattaaa aatgaagttt taaatcaatc taaagtatat    4500
atgagtaaac ttggtctgac agttaccaat gcttaatcag tgaggcacct atctcagcga    4560
tctgtctatt tcgttcatcc atagttgcct gactccccgt cgtgtagata actacgatac    4620
gggagggctt accatctggc cccagtgctg caatgatacc gcgagaccca cgctcaccgg    4680
ctccagattt atcagcaata aaccagccag ccggaagggc cgagcgcaga agtggtcctg    4740
caactttatc cgcctccatc cagtctatta attgttgccg ggaagctaga gtaagtagtt    4800
cgccagttaa tagtttgcgc aacgttgttg ccattgctac aggcatcgtg gtgtcacgct    4860
cgtcgtttgg tatggcttca ttcagctccg gttcccaacg atcaaggcga gttacatgat    4920
cccccatgtt gtgcaaaaaa gcggttagct ccttcggtcc tccgatcgtt gtcagaagta    4980
agttggccgc agtgttatca ctcatggtta tggcagcact gcataattct cttactgtca    5040
tgccatccgt aagatgcttt tctgtgactg gtgagtactc aaccaagtca ttctgagaat    5100
agtgtatgcg gcgaccgagt tgctcttgcc cggcgtcaat acgggataat accgcgccac    5160
atagcagaac tttaaaagtg ctcatcattg gaaaacgttc ttcggggcga aaactctcaa    5220
ggatcttacc gctgttgaga tccagttcga tgtaacccac tcgtgcaccc aactgatctt    5280
cagcatcttt tactttcacc agcgtttctg ggtgagcaaa aacaggaagg caaaatgccg    5340
caaaaaaggg aataagggcg acacggaaat gttgaatact catactcttc ctttttcaat    5400
attattgaag catttatcag ggttattgtc tcatgagcgg atacatattt gaatgtattt    5460
agaaaaataa acaaataggg gttccgcgca catttccccg aaaagtgcca cctgacgtct    5520
aagaaaccat tattatcatg acattaacct ataaaaatag gcgtatcacg aggccctttc    5580
gtctcgcgcg tttcggtgat gacggtgaaa acctctgaca catgcagctc ccggagacgg    5640
tcacagcttg tctgtaagcg gatgccggga gcagacaagc ccgtcagggc gcgtcagcgg    5700
gtgttggcgg gtgtcggggc tggcttaact atgcggcatc agagcagatt gtactgagag    5760
tgcaccatat gcggtgtgaa ataccgcaca gatgcgtaag gagaaaatac cgcatcaggc    5820
gccattcgcc attcaggctg cgcaactgtt gggaagggcg atcggtgcgg gcctcttcgc    5880
tattacgcca gctggcgaaa gggggatgtg ctgcaaggcg attaagttgg gtaacgccag    5940
ggttttccca gtcacgacgt tgtaaaacga cggccagtgc cacgctctcc cttatgcgac    6000
tcctgcatta ggaagcagcc cagtagtagg ttgaggccgt tgagcaccgc cgccgcaagg    6060
aatggtgcat gcaaggagat ggcgcccaac agtcccccgg ccacggggcc tgccaccata    6120
cccacgccga acaagcgct catgagcccg aagtggcgag cccgatcttc cccatcggtg    6180
atgtcggcga tataggcgcc agcaaccgca cctgtggcgc cggtgatgcc ggccacgatg    6240
cgtccggcgt agag                                                      6254

<210> SEQ ID NO 2
<211> LENGTH: 7295
<212> TYPE: DNA
<213> ORGANISM: Artificial Sequence
<220> FEATURE:
<223> OTHER INFORMATION: This represents a retroviral vector encoding a
      T-cell receptor that recognizes an epitope of
      gp-100

<400> SEQUENCE: 2
tgaaagaccc cacctgtagg tttggcaagc tagcttaagt aacgccattt tgcaaggcat      60
ggaaaataca taactgagaa tagagaagtt cagatcaagg ttaggaacag agagacagca     120
```

```
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactcgg cgcgccagtc ctccgataga ctgcgtcgcc cgggtacccg tattcccaat    420
aaagcctctt gctgtttgca tccgaatcgt ggactcgctg atccttggga gggtctcctc    480
agattgattg actgcccacc tcggggggtct ttcatttgga ggttccaccg agatttggag    540 accccctgcct agggaccacc gaccccccccg ccgggaggta agctggccag cggtcgtttc    600
gtgtctgtct ctgtctttgt gcgtgtttgt gccggcatct aatgtttgcg cctgcgtctg    660
tactagttag ctaactagct ctgtatctgg cggacccgtg gtggaactga cgagttctga    720
acacccggcc gcaaccctgg gagacgtccc agggactttg ggggccgttt ttgtggcccg    780
acctgaggaa gggagtcgat gtggaatccg accccgtcag gatatgtggt tctggtagga    840
gacgagaacc taaaacagtt cccgcctccg tctgaatttt tgctttcggt ttggaaccga    900
agccgcgcgt cttgtctgct gcagcgctgc agcatcgttc tgtgttgtct ctgtctgact    960
gtgtttctgt atttgtctga aaattagggc cagactgtta ccactccctt aagtttgacc   1020
ttaggtcact ggaaagatgt cgagcggatc gctcacaacc agtcggtaga tgtcaagaag   1080
agacgttggg ttaccttctg ctctgcagaa tggccaacct ttaacgtcgg atggccgcga   1140
gacggcacct ttaaccgaga cctcatcacc caggttaaga tcaaggtctt ttcacctggc   1200
ccgcatggac acccagacca ggtcccctac atcgtgacct gggaagcctt ggcttttgac   1260 cccccctccct gggtcaagcc ctttgtacac cctaagcctc cgcctcctct tcctccatcc   1320
gccccgtctc tccccctttga acctcctcgt tcgaccccgc ctcgatcctc cctttatcca   1380
gccctcactc cttctctagg cgccgagatc tctcgaggtt aacgaaacgg atccatggtg   1440
aagatccggc aattttttgtt ggctatttttg tggcttcagc taagctgtgt aagtgccgcc   1500
aaaaatgaag tggagcagag tcctcagaac ctgactgccc aggaaggaga atttatcaca   1560
atcaactgca gttactcggt aggaataagt gccttacact ggctgcaaca gcatccagga   1620
ggaggcattg tttccttgtt tatgctgagc tcagggaaga agaagcatgg aagattaatt   1680
gccacaataa acatacagga aaagcacagc tccctgcaca tcacagcctc ccatcccaga   1740
gactctgccg tctacatctg tgctgcctca ttaattcagg gagcccagaa gctggtattt   1800
ggccaaggaa ccaggctgac tatcaaccca aatatccaga accctgaccc tgccgtgtac   1860
cagctgagag actctaaatc cagtgacaag tctgtctgcc tattcaccga ttttgattct   1920
caaacaaatg tgtcacaaag taaggattct gatgtgtata tcacagacaa aactgtgcta   1980
gacatgaggt ctatggactt caagagcaac agtgctgtgg cctggagcaa caaatctgac   2040
tttgcatgtg caaacgcctt caacaacagc attattccag aagcacctt cttccccagc   2100 ccagaaagtt cctgtgatgt caagctggtc gagaaaagct ttgaaacaga tacgaaccta   2160
aactttcaaa acctgtcagt gattgggttc cgaatcctcc tcctgaaagt ggccgggttt   2220
aatctgctca tgacgctgcg gctgtggtcc agctgagaat ccgctgagg ctgtggtcca   2280 gttgacgccc ctctccctcc ccccccccta acgttactgg ccgaagccgc ttggaataag   2340
gccggtgtgc gtttgtctat atgttatttt ccaccatatt gccgtctttt ggcaatgtga   2400
gggcccggaa acctggccct gtcttcttga cgagcattcc tagggggtctt tcccctctcg   2460 ccaaaggaat gcaaggtctg ttgaatgtcg tgaaggaagc agttcctctg gaagcttctt   2520
```

```
gaagacaaac aacgtctgta gcgacccttt gcaggcagcg aaccccccca cctggcgaca    2580
ggtgcctctg cggccaaaag ccacgtgtat aagatacacc tgcaaaggcg gcacaacccc    2640
agtgccacgt tgtgagttgg atagttgtgg aaagagtcaa atggctctcc tcaagcgtat    2700
tcaacaaggg gctgaaggat gcccagaagg tacccattg tatgggatct gatctggggc     2760
ctcggtgcac atgctttaca tgtgtttagt cgaggttaaa aaacgtctag gccccccgaa    2820
ccacggggac gtggttttcc tttgaaaaac acgatgataa tatgccaca accatggact     2880 cctggacctt ctgctgtgtg tccctttgca tcctggtagc gaagcataca gatgctggag    2940
ttatccagtc accccgccat gaggtgacag agatgggaca agaagtgact ctgagatgta    3000
aaccaatttc aggccacaac tccctttttct ggtacagaca gaccatgatg cggggactgg   3060
agttgctcat ttactttaac aacaacgttc cgatagatga ttcagggatg cccgaggatc    3120
gattctcagc taagatgcct aatgcatcat tctccactct gaagatccag ccctcagaac    3180
ccagggactc agctgtgtac ttctgtgcca gcagccccgg gggcaatgag cagttcttcg    3240
ggccagggac acggctcacc gtgctagagg acctgaaaaa cgtgttccca cccgaggtcg    3300
ctgtgtttga gccatcagaa gcagagatct cccacaccca aaaggccaca ctggtatgcc    3360
tggccacagg cttctacccc gaccacgtgg agctgagctg gtgggtgaat gggaaggagg    3420
tgcacagtgg ggtcagcaca gacccgcagc ccctcaagga gcagcccgcc ctcaatgact    3480
ccagatactg cctgagcagc cgcctgaggg tctcggccac cttctggcag aaccccgca     3540 accacttccg ctgtcaagtc cagttctacg ggctctcgga gaatgacgag tggacccagg    3600
atagggccaa acccgtcacc cagatcgtca gcgccgaggc ctggggtaga gcagactgtg    3660
gcttcacctc cgagtcttac cagcaagggg tcctgtctgc caccatcctc tatgagatct    3720
tgctagggaa ggccaccttg tatgccgtgc tggtcagtgc cctcgtgctg atggccatgg    3780
tcaagagaaa ggattccaga ggctaggtcg acctgcagcc aagcttatcg ataaaataaa    3840
agattttatt tagtctccag aaaaaggggg gaatgaaaga ccccacctgt aggtttggca    3900
agctagctta agtaacgcca ttttgcaagg catggaaaat acataactga gaatagagaa    3960
gttcagatca aggttaggaa cagagagaca gcagaatatg ggccaaacag gatatctgtg    4020
gtaagcagtt cctgccccgg ctcagggcca agaacagatg gtccccagat gcggtcccgc    4080
cctcagcagt ttctagagaa ccatcagatg tttccagggt gccccaagga cctgaaaatg    4140
accctgtgcc ttatttgaac taaccaatca gttcgcttct cgcttctgtt cgcgcgcttc    4200
tgctccccga gctcaataaa agagcccaca acccctcact cggcgcgcca gtcctccgat    4260
agactgcgtc gcccgggtac ccgtgtatcc aataaaccct cttgcagttg catccgactt    4320
gtggtctcgc tgttccttgg gagggtctcc tctgagtgat tgactacccg tcagcggggg    4380
tctttcagta ttcgtaatca tggtcatagc tgtttcctgt gtgaaattgt tatccgctca    4440
caattccaca caacatacga gccggaagca taaagtgtaa agcctgggt gcctaatgag    4500 tgagctaact cacattaatt gcgttgcgct cactgcccgc tttccagtcg ggaaacctgt    4560
cgtgccagct gcattaatga atcggccaac gcgcgggga aggcggtttg cgtattgggc    4620
gctcttccgc ttcctcgctc actgactcgc tgcgctcggt cgttcggctg cggcgagcgg    4680
tatcagctca ctcaaaggcg gtaatacggt tatccacaga atcaggggat aacgcaggaa    4740
agaacatgtg agcaaaaggc cagcaaaagg ccaggaaccg taaaaaggcc gcgttgctgg    4800
cgtttttcca taggctccgc ccccctgacg agcatcacaa aaatcgacgc tcaagtcaga    4860
ggtggcgaaa cccgacagga ctataaagat accaggcgtt tcccctgga agctccctcg     4920
```

```
tgcgctctcc tgttccgacc ctgccgctta ccggatacct gtccgccttt ctcccttcgg   4980
gaagcgtggc gctttctcat agctcacgct gtaggtatct cagttcggtg taggtcgttc   5040
gctccaagct gggctgtgtg cacgaacccc ccgttcagcc cgaccgctgc gccttatccg   5100
gtaactatcg tcttgagtcc aacccggtaa gacacgactt atcgccactg gcagcagcca   5160
ctggtaacag gattagcaga gcgaggtatg taggcggtgc tacagagttc ttgaagtggt   5220
ggcctaacta cggctacact agaaggacag tatttggtat ctgcgctctg ctgaagccag   5280
ttaccttcgg aaaaagagtt ggtagctctt gatccggcaa acaaaccacc gctggtagcg   5340
gtggtttttt tgtttgcaag cagcagatta cgcgcagaaa aaaaggatct caagaagatc   5400
ctttgatctt ttctacgggg tctgacgctc agtggaacga aaactcacgt taagggattt   5460
tggtcatgag attatcaaaa aggatcttca cctagatcct tttaaattaa aaatgaagtt   5520
ttaaatcaat ctaaagtata tatgagtaaa cttggtctga cagttaccaa tgcttaatca   5580
gtgaggcacc tatctcagcg atctgtctat ttcgttcatc catagttgcc tgactccccg   5640
tcgtgtagat aactacgata cgggagggct taccatctgg ccccagtgct gcaatgatac   5700
cgcgagaccc acgctcaccg gctccagatt tatcagcaat aaaccagcca gccggaaggg   5760
ccgagcgcag aagtggtcct gcaactttat ccgcctccat ccagtctatt aattgttgcc   5820
gggaagctag agtaagtagt tcgccagtta atagtttgcg caacgttgtt gccattgcta   5880
caggcatcgt ggtgtcacgc tcgtcgtttg gtatggcttc attcagctcc ggttcccaac   5940
gatcaaggcg agtacatga tcccccatgt tgtgcaaaaa agcggttagc tccttcggtc   6000
ctccgatcgt tgtcagaagt aagttggccg cagtgttatc actcatggtt atggcagcac   6060
tgcataattc tcttactgtc atgccatccg taagatgctt ttctgtgact ggtgagtact   6120
caaccaagtc attctgagaa tagtgtatgc ggcgaccgag ttgctcttgc ccggcgtcaa   6180
tacgggataa taccgcgcca catagcagaa ctttaaaagt gctcatcatt ggaaaacgtt   6240
cttcggggcg aaaactctca aggatcttac cgctgttgag atccagttcg atgtaaccca   6300
ctcgtgcacc caactgatct tcagcatctt ttactttcac cagcgtttct gggtgagcaa   6360
aaacaggaag gcaaaatgcc gcaaaaaagg gaataagggc gacacggaaa tgttgaatac   6420
tcatactctt cctttttcaa tattattgaa gcatttatca gggttattgt ctcatgagcg   6480
gatacatatt tgaatgtatt tagaaaaata aacaaatagg ggttccgcgc acatttcccc   6540
gaaaagtgcc acctgacgtc taagaaacca ttattatcat gacattaacc tataaaaata   6600
ggcgtatcac gaggcccttt cgtctcgcgc gtttcggtga tgacggtgaa aacctctgac   6660
acatgcagct cccggagacg gtcacagctt gtctgtaagc ggatgccggg agcagacaag   6720
cccgtcaggg cgcgtcagcg ggtgttggcg ggtgtcgggg ctggcttaac tatgcggcat   6780
cagagcagat tgtactgaga gtgcaccata tgcggtgtga ataccgcac agatgcgtaa   6840 ggagaaaata ccgcatcagg cgccattcgc cattcaggct gcgcaactgt tgggaagggc   6900
gatcggtgcg ggcctcttcg ctattacgcc agctggcgaa agggggatgt gctgcaaggc   6960
gattaagttg ggtaacgcca gggttttccc agtcacgacg ttgtaaaacg acggccagtg   7020
ccacgctctc ccttatgcga ctcctgcatt aggaagcagc ccagtagtag gttgaggccg   7080
ttgagcaccg ccgccgcaag gaatggtgca tgcaaggaga tggcgcccaa cagtcccccg   7140
gccacggggc ctgccaccat acccacgccg aaacaagcgc tcatgagccc gaagtggcga   7200
gcccgatctt ccccatcgt gatgtcgcg atataggcgc cagcaaccgc acctgtggcg   7260
ccggtgatgc cggccacgat gcgtccggcg tagag                               7295
```

<210> SEQ ID NO 3
<211> LENGTH: 7277
<212> TYPE: DNA
<213> ORGANISM: Artificial Sequence
<220> FEATURE:
<223> OTHER INFORMATION: This represents a retroviral vector encoding a
      T-cell receptor that recognizes an epitope of
      Mart-1

<400> SEQUENCE: 3

| | | | | | |
|---|---|---|---|---|---|
| tgaaagaccc | cacctgtagg | tttggcaagc | tagcttaagt | aacgccattt | tgcaaggcat | 60 |
| ggaaaataca | taactgagaa | tagagaagtt | cagatcaagg | ttaggaacag | agagacagca | 120 |
| gaatatgggc | caaacaggat | atctgtggta | agcagttcct | gccccggctc | agggccaaga | 180 |
| acagatggtc | cccagatgcg | gtcccgccct | cagcagtttc | tagagaacca | tcagatgttt | 240 |
| ccagggtgcc | ccaaggacct | gaaaatgacc | ctgtgcctta | tttgaactaa | ccaatcagtt | 300 |
| cgcttctcgc | ttctgttcgc | gcgcttctgc | tccccgagct | caataaaaga | gcccacaacc | 360 |
| cctcactcgg | cgcgccagtc | ctccgataga | ctgcgtcgcc | cgggtacccg | tattcccaat | 420 |
| aaagcctctt | gctgtttgca | tccgaatcgt | ggactcgctg | atccttggga | gggtctcctc | 480 |
| agattgattg | actgcccacc | tcggggtct | ttcatttgga | ggttccaccg | agatttggag | 540 |
| accctgcct | agggaccacc | gacccccccg | ccgggaggta | agctggccag | cggtcgtttc | 600 |
| gtgtctgtct | ctgtctttgt | gcgtgtttgt | gccggcatct | aatgtttgcg | cctgcgtctg | 660 |
| tactagttag | ctaactagct | ctgtatctgg | cggacccgtg | gtggaactga | cgagttctga | 720 |
| acacccggcc | gcaaccctgg | gagacgtccc | agggactttg | ggggccgttt | tgtggcccg | 780 |
| acctgaggaa | gggagtcgat | gtggaatccg | accccgtcag | gatatgtggt | tctggtagga | 840 |
| gacgagaacc | taaaacagtt | cccgcctccg | tctgaatttt | tgctttcggt | ttggaaccga | 900 |
| agccgcgcgt | cttgtctgct | gcagcgctgc | agcatcgttc | tgtgttgtct | ctgtctgact | 960 |
| gtgtttctgt | atttgtctga | aaattagggc | cagactgtta | ccactcccct | aagtttgacc | 1020 |
| ttaggtcact | ggaaagatgt | cgagcggatc | gctcacaacc | agtcggtaga | tgtcaagaag | 1080 |
| agacgttggg | ttaccttctg | ctctgcagaa | tggccaacct | ttaacgtcgg | atggccgcga | 1140 |
| gacggcacct | ttaaccgaga | cctcatcacc | caggttaaga | tcaaggtctt | ttcacctggc | 1200 |
| ccgcatggac | acccagacca | ggtcccctac | atcgtgacct | gggaagcctt | ggcttttgac | 1260 |
| cccccctccct | gggtcaagcc | ctttgtacac | cctaagcctc | cgcctcctct | tcctccatcc | 1320 |
| gccccgtctc | tcccccttga | acctcctcgt | tcgacccgc | ctcgatcctc | cctttatcca | 1380 |
| gccctcactc | cttctctagg | cgccgagatc | tctcgaggtt | aacgaaacgg | atccatgttg | 1440 |
| cttgaacatt | tattaataat | cttgtggatg | cagctgacat | gggtcagtgg | tcaacagctg | 1500 |
| aatcagagtc | ctcaatctat | gtttatccag | gaaggagaag | atgtctccat | gaactgcact | 1560 |
| tcttcaagca | tatttaacac | ctggctatgg | tacaagcagg | accctgggga | aggtcctgtc | 1620 |
| ctcttgatag | ccttatataa | ggctggtgaa | ttgacctcaa | atggaagact | gactgctcag | 1680 |
| tttggtataa | ccagaaagga | cagcttcctg | aatatctcag | catccatacc | tagtgatgta | 1740 |
| ggcatctact | tctgtgctgg | tgggaccggt | aaccagttct | attttgggac | agggacaagt | 1800 |
| ttgacggtca | ttccaaatat | ccagaaccct | gaccctgccg | tgtaccagct | gagagactct | 1860 |
| aaatccagtg | acaagtctgt | ctgcctattc | accgattttg | attctcaaac | aaatgtgtca | 1920 |
| caaagtaagg | attctgatgt | gtatatcaca | gacaaaactg | tgctagacat | gaggtctatg | 1980 |
| gacttcaaga | gcaacagtgc | tgtggcctgg | agcaacaaat | ctgactttgc | atgtgcaaac | 2040 |

```
gccttcaaca acagcattat tccagaagac accttcttcc ccagcccaga aagttcctgt    2100
gatgtcaagc tggtcgagaa aagctttgaa acagatacga acctaaactt tcaaaacctg    2160
tcagtgattg ggttccgaat cctcctcctg aaggtggccg ggtttaatct gctcatgacg    2220
ctgcggctgt ggtccagctg agaattccgc tgaggctgtg gtccagttga cgcccctctc    2280
cctccccccc ccctaacgtt actggccgaa gccgcttgga ataaggccgg tgtgcgtttg    2340
tctatatgtt attttccacc atattgccgt cttttggcaa tgtgagggcc cggaaacctg    2400
gccctgtctt cttgacgagc attcctaggg gtctttcccc tctcgccaaa ggaatgcaag    2460
gtctgttgaa tgtcgtgaag gaagcagttc ctctggaagc ttcttgaaga caaacaacgt    2520
ctgtagcgac cctttgcagg cagcggaacc cccacctgg cgacaggtgc ctctgcggcc    2580
aaaagccacg tgtataagat acacctgcaa aggcggcaca accccagtgc cacgttgtga    2640
gttggatagt tgtggaaaga gtcaaatggc tctcctcaag cgtattcaac aaggggctga    2700
aggatgccca gaaggtaccc cattgtatgg gatctgatct ggggcctcgg tgcacatgct    2760
ttacatgtgt ttagtcgagg ttaaaaaacg tctaggcccc ccgaaccacg gggacgtggt    2820
tttcctttga aaaacacgat gataatatgg ccacaaccat gggcacaagg ttgttcttct    2880
atgtggccct ttgtctcctg tggacaggac acatggatgc tggaatcacc cagagcccaa    2940
gacacaaggt cacagagaca ggaacaccag tgactctgag atgtcaccag actgagaacc    3000
accgctatat gtactggtat cgacaagacc cggggcatgg gctgaggctg atccattact    3060
catatggtgt taaagatact gacaaaggag aagtctcaga tggctatagt gtctctagat    3120
caaagacaga ggatttcctc ctcactctgg agtccgctac cagctcccag acatctgtgt    3180
acttctgtgc catcagtgag gtaggggttg ggcagcccca gcattttggt gatgggactc    3240
gactctccat cctagaggac ctgaacaagg tgttcccacc cgaggtcgct gtgtttgagc    3300
catcagaagc agagatctcc cacacccaaa aggccacact ggtgtgcctg gccacaggct    3360
tcttccctga ccacgtggag ctgagctggt gggtgaatgg gaaggaggtg cacagtgggg    3420
tcagcacgga cccgcagccc ctcaaggagc agcccgccct caatgactcc agatactgcc    3480
tgagcagccg cctgagggtc tcggccacct tctggcagaa cccccgcaac cacttccgct    3540
gtcaagtcca gttctacggg ctctcggaga atgacgagtg gacccaggat agggccaaac    3600
ccgtcaccca gatcgtcagc gccgaggcct ggggtagagc agactgtggc tttacctcgg    3660
tgtcctacca gcaaggggtc ctgtctgcca ccatcctcta tgagatcctg ctagggaagg    3720
ccaccctgta tgctgtgctg gtcagcgccc ttgtgttgat ggccatggtc aagagaaagg    3780
atttctgagt cgacctgcag ccaagcttat cgataaaata aaagatttta tttagtctcc    3840
agaaaaaggg gggaatgaaa gaccccacct gtaggtttgg caagctagct taagtaacgc    3900
cattttgcaa ggcatggaaa atacataact gagaatagag aagttcagat caaggttagg    3960
aacagagaga cagcagaata tgggccaaac aggatatctg tggtaagcag ttcctgcccc    4020
ggctcagggc caagaacaga tggtcccag atgcggtccc gccctcagca gtttctagag    4080
aaccatcaga tgtttccagg gtgccccaag gacctgaaaa tgaccctgtg ccttatttga    4140
actaaccaat cagttcgctt ctcgcttctg ttcgcgcgct tctgctcccc gagctcaata    4200
aaagagccca aacccctca ctcggcgcgc cagtcctccg atagactgcg tcgcccgggt    4260
acccgtgtat ccaataaacc ctcttgcagt tgcatccgac ttgtggtctc gctgttcctt    4320
gggagggtct cctctgagtg attgactacc cgtcagcggg ggtctttcag tattcgtaat    4380
catggtcata gctgtttcct gtgtgaaatt gttatccgct cacaattcca cacaacatac    4440
```

```
gagccggaag cataaagtgt aaagcctggg gtgcctaatg agtgagctaa ctcacattaa   4500
ttgcgttgcg ctcactgccc gctttccagt cgggaaacct gtcgtgccag ctgcattaat   4560
gaatcggcca acgcgcgggg agaggcggtt tgcgtattgg gcgctcttcc gcttcctcgc   4620
tcactgactc gctgcgctcg gtcgttcggc tgcggcgagc ggtatcagct cactcaaagg   4680
cggtaatacg gttatccaca gaatcagggg ataacgcagg aaagaacatg tgagcaaaag   4740
gccagcaaaa ggccaggaac cgtaaaaagg ccgcgttgct ggcgtttttc cataggctcc   4800
gcccccctga cgagcatcac aaaaatcgac gctcaagtca gaggtggcga aacccgacag   4860
gactataaag ataccaggcg tttccccctg gaagctccct cgtgcgctct cctgttccga   4920
ccctgccgct taccggatac ctgtccgcct ttctcccttc gggaagcgtg gcgctttctc   4980
atagctcacg ctgtaggtat ctcagttcgg tgtaggtcgt tcgctccaag ctgggctgtg   5040
tgcacgaacc ccccgttcag cccgaccgct gcgccttatc cggtaactat cgtcttgagt   5100
ccaacccggt aagacacgac ttatcgccac tggcagcagc cactggtaac aggattagca   5160
gagcgaggta tgtaggcggt gctacagagt tcttgaagtg gtggcctaac tacggctaca   5220
ctagaaggac agtatttggt atctgcgctc tgctgaagcc agttaccttc ggaaaaagag   5280
ttggtagctc ttgatccggc aaacaaacca ccgctggtag cggtggtttt tttgtttgca   5340
agcagcagat tacgcgcaga aaaaaggat ctcaagaaga tcctttgatc ttttctacgg   5400
ggtctgacgc tcagtggaac gaaaactcac gttaagggat tttggtcatg agattatcaa   5460
aaaggatctt cacctagatc cttttaaatt aaaaatgaag ttttaaatca atctaaagta   5520
tatatgagta aacttggtct gacagttacc aatgcttaat cagtgaggca cctatctcag   5580
cgatctgtct atttcgttca tccatagttg cctgactccc cgtcgtgtag ataactacga   5640
tacgggaggg cttaccatct ggccccagtg ctgcaatgat accgcgagac ccacgctcac   5700
cggctccaga tttatcagca ataaaccagc cagccggaag ggccgagcgc agaagtggtc   5760
ctgcaacttt atccgcctcc atccagtcta ttaattgttg ccgggaagct agagtaagta   5820
gttcgccagt taatagtttg cgcaacgttg ttgccattgc tacaggcatc gtggtgtcac   5880
gctcgtcgtt tggtatggct tcattcagct ccggttccca acgatcaagg cgagttacat   5940
gatcccccat gttgtgcaaa aaagcggtta gctccttcgg tcctccgatc gttgtcagaa   6000
gtaagttggc cgcagtgtta tcactcatgg ttatggcagc actgcataat tctcttactg   6060
tcatgccatc cgtaagatgc ttttctgtga ctggtgagta ctcaaccaag tcattctgag   6120
aatagtgtat gcggcgaccg agttgctctt gcccggcgtc aatacgggat aataccgcgc   6180
cacatagcag aactttaaaa gtgctcatca ttggaaaacg ttcttcgggg cgaaaactct   6240
caaggatctt accgctgttg agatccagtt cgatgtaacc cactcgtgca cccaactgat   6300
cttcagcatc ttttactttc accagcgttt ctgggtgagc aaaaacagga aggcaaaatg   6360
ccgcaaaaaa gggaataagg gcgacacgga aatgttgaat actcatactc ttcctttttc   6420
aatattattg aagcatttat cagggttatt gtctcatgag cggatacata tttgaatgta   6480
tttagaaaaa taaacaaata ggggttccgc gcacatttcc ccgaaaagtg ccacctgacg   6540
tctaagaaac cattattatc atgacattaa cctataaaaa taggcgtatc acgaggccct   6600
ttcgtctcgc gcgtttcggt gatgacggtg aaaacctctg acacatgcag ctcccggaga   6660
cggtcacagc ttgtctgtaa gcggatgccg ggagcagaca agcccgtcag ggcgcgtcag   6720
cgggtgttgg cgggtgtcgg ggctggctta actatgcggc atcagagcag attgtactga   6780
gagtgcacca tatgcggtgt gaaataccgc acagatgcgt aaggagaaaa taccgcatca   6840
```

```
ggcgccattc gccattcagg ctgcgcaact gttgggaagg gcgatcggtg cgggcctctt      6900
cgctattacg ccagctggcg aaaggqggat gtgctgcaag gcgattaagt tgggtaacgc      6960
cagggttttc ccagtcacga cgttgtaaaa cgacggccag tgccacgctc tcccttatgc      7020
gactcctgca ttaggaagca gcccagtagt aggttgaggc cgttgagcac cgccgccgca      7080
aggaatggtg catgcaagga gatggcgccc aacagtcccc cggccacggg gcctgccacc      7140
atacccacgc cgaaacaagc gctcatgagc ccgaagtggc gagcccgatc ttccccatcg      7200
gtgatgtcgg cgatataggc gccagcaacc gcacctgtgg cgccggtgat gccggccacg      7260
atgcgtccgg cgtagag                                                     7277

<210> SEQ ID NO 4
<211> LENGTH: 6779
<212> TYPE: DNA
<213> ORGANISM: Artificial Sequence
<220> FEATURE:
<223> OTHER INFORMATION: This represents a retroviral vector derived
      from the murine stem cell virus

<400> SEQUENCE: 4
tgaaagaccc cacctgtagg tttggcaagc tagcttaagt aacgccattt tgcaaggcat        60
ggaaaataca taactgagaa tagagaagtt cagatcaagg ttaggaacag agagacagca       120
gaatatgggc caaacaggat atctgtggta agcagttcct gccccggctc agggccaaga       180
acagatggtc cccagatgcg gtcccgccct cagcagtttc tagagaacca tcagatgttt       240
ccagggtgcc ccaaggacct gaaaatgacc ctgtgcctta tttgaactaa ccaatcagtt       300
cgcttctcgc ttctgttcgc gcgcttctgc tccccgagct caataaaaga gcccacaacc       360
cctcactcgg cgcgccagtc ctccgataga ctgcgtcgcc cgggtacccg tattcccaat       420
aaagcctctt gctgtttgca tccgaatcgt ggactgctg atccttggga gggtctcctc       480
agattgattg actgcccacc tcgggggtct ttcatttgga ggttccaccg agatttggag       540 accccctgcct agggaccacc gacccccccg ccggggaggta agctggccag cggtcgtttc       600
gtgtctgtct ctgtctttgt gcgtgtttgt gccggcatct aatgtttgcg cctgcgtctg       660
tactagttag ctaactagct ctgtatctgg cggacccgtg gtggaactga cgagttctga       720
acacccggcc gcaaccctgg gagacgtccc agggactttg ggggccgttt ttgtggcccg       780
acctgaggaa gggagtcgat gtggaatccg accccgtcag gatatgtggt tctggtagga       840
gacgagaacc taaacagtt cccgcctccg tctgaatttt tgctttcggt ttggaaccga       900
agccgcgcgt cttgtctgct gcagcgctgc agcatcgttc tgtgttgtct ctgtctgact       960
gtgtttctgt atttgtctga aaattagggc cagactgtta ccactccctt aagtttgacc      1020
ttaggtcact ggaaagatgt cgagcggatc gctcacaacc agtcggtaga tgtcaagaag      1080
agacgttggg ttaccttctg ctctgcagaa tggccaacct ttaacgtcgg atggccgcga      1140
gacggcacct ttaaccgaga cctcatcacc caggttaaga tcaaggtctt tcacctggc      1200 ccgcatggac acccagacca ggtccccta catcgtgacct gggaagcctt ggcttttgac      1260
ccccctccct gggtcaagcc ctttgtacac cctaagcctc cgcctcctct tcctccatcc      1320
gccccgtctc tccccttga acctcctcgt tcgacccgc ctcgatcctc cctttatcca      1380
gccctcactc cttctctagg cgccgagatc tctcgaggtt gttggatcca ggaatggaca      1440
agattctgac agcaacgttt ttactcctag gccttcacct agctgggtg aatggccagc      1500 agcaggagaa acgtgaccag cagcaggtga gacaaagtcc ccaatctctg acagtctggg      1560
```

-continued

```
aaggagagac cgcaattctg aactgcagtt atgaggacag cacttttaac tacttcccat    1620
ggtaccagca gttccctggg gaaggccctg cactcctgat atccatacgt tcagtgtccg    1680
ataaaaagga agatggacga ttcacaatct tcttcaataa agggagaaa aagctctcct    1740 tgcacatcac agactctcag cctggagact cagctaccta cttctgtgca gcaagggta    1800 acagaatctt ctttggtgat gggacgcagc tggtggtgaa gcccaacatc agaacccag    1860 aacctgctgt gtaccagtta aaagatcctc ggtctcagga cagcaccctc tgcctgttca    1920
ccgactttga ctcccaaatc aatgtgccga aaccatgga atctggaacg ttcatcactg    1980
acaaaactgt gctggacatg aaagctatgg attccaagag caatgggcc attgcctgga    2040 gcaaccagac aagcttcacc tgccaagata tcttcaaaga gaccaacgcc acctacccca    2100
gttcagacgt tccctgtgat gccacgttga ctgagaaaag ctttgaaaca gatatgaacc    2160
taaactttca aaacctgtca gttatgggac tccgaatcct cctgctgaaa gtagccggat    2220
ttaacctgct catgacgctg aggctgtggt ccagtcgggc taagagagca ccggtgaaac    2280
agactttgaa ttttgacctt ctcaagttgg cgggagacgt ggagtccaac ccagggccca    2340
tgtctaacac tgccttccct gaccccgcct ggaacaccac cctgctatct tgggttgctc    2400
tctttctcct gggaacaagt tcagcaaatt ctggggttgt ccagtctcca agatacataa    2460
tcaaaggaaa gggagaaagg tccattctaa aatgtattcc catctctgga catctctctg    2520
tggcctggta tcaacagact cagggcagg aactaaagtt cttcattcag cattatgata    2580
aaatggagag agataaagga aacctgccca gcagattctc agtccaacag tttgatgact    2640
atcactctga tgaacatg agtgccttgg agctagagga ctctgccgtg tacttctgtg    2700
ccagctctct cggggggggag agtcaaaaca ccttgtactt tggtgcgggc acccgactat    2760
cggtgctaga ggatctgaga aatgtgactc cacccaaggt ctccttgttt gagccatcaa    2820
aagcagagat tgcaaacaaa caaaaggcta ccctcgtgtg cttggccagg gcttcttcc    2880 ctgaccacgt ggagctgagc tggtgggtga atggcaagga ggtccacagt ggggtcagca    2940
cggaccctca ggcctacaag gagagcaatt atagctactg cctgagcagc cgcctgaggg    3000
tctctgctac cttctggcac aatcctcgaa accacttccg ctgccaagtg cagttccatg    3060
ggctttcaga ggaggacaag tggccagagg gctcacccaa acctgtcaca cagaacatca    3120
gtgcagaggc ctggggccga gcagactgtg gaatcacttc agcatcctat catcaggggg    3180
ttctgtctgc aaccatcctc tatgagatcc tactggggaa ggccacccta tatgctgtgc    3240
tggtcagtgg cctggtgctg atggccatgg tcaagaaaaa aaattcctga gtcgacctgc    3300
agccaagctt atcgataaaa taaaagattt tatttagtct ccagaaaaag gggggaatga    3360
aagaccccac ctgtaggttt ggcaagctag cttaagtaac gccattttgc aaggcatgga    3420
aaatacataa ctgagaatag agaagttcag atcaaggtta ggaacagaga gacagcagaa    3480
tatgggccaa acaggatatc tgtggtaagc agttcctgcc ccggctcagg gccaagaaca    3540
gatggtcccc agatgcggtc cgccctcag cagtttctag agaaccatca gatgtttcca    3600 gggtgccccca aggacctgaa aatgaccctg tgccttattt gaactaacca atcagttcgc    3660
ttctcgcttc tgttcgcgcg cttctgctcc ccgagctcaa taaaagagcc cacaacccct    3720
cactcggcgc gccagtcctc cgatagactg cgtcgcccgg gtaccgtgt atccaataaa    3780 ccctcttgca gttgcatccg acttgtggtc tcgctgttcc ttgggagggt ctcctctgag    3840
tgattgacta cccgtcagcg ggggtctttc agtattcgta atcatggtca tagctgtttc    3900
ctgtgtgaaa ttgttatccg ctcacaattc cacacaacat acgagccgga agcataaagt    3960
```

```
gtaaagcctg gggtgcctaa tgagtgagct aactcacatt aattgcgttg cgctcactgc    4020
ccgctttcca gtcgggaaac ctgtcgtgcc agctgcatta atgaatcggc caacgcgcgg    4080
ggagaggcgg tttgcgtatt gggcgctctt ccgcttcctc gctcactgac tcgctgcgct    4140
cggtcgttcg gctgcggcga gcggtatcag ctcactcaaa ggcggtaata cggttatcca    4200
cagaatcagg ggataacgca ggaaagaaca tgtgagcaaa aggccagcaa aaggccagga    4260
accgtaaaaa ggccgcgttg ctggcgtttt tccataggct ccgcccccct gacgagcatc    4320
acaaaaatcg acgctcaagt cagaggtggc gaaacccgac aggactataa agataccagg    4380
cgtttccccc tggaagctcc ctcgtgcgct ctcctgttcc gaccctgccg cttaccggat    4440
acctgtccgc ctttctccct tcgggaagcg tggcgctttc tcatagctca cgctgtaggt    4500
atctcagttc ggtgtaggtc gttcgctcca agctgggctg tgtgcacgaa ccccccgttc    4560
agcccgaccg ctgcgcctta tccggtaact atcgtcttga gtccaacccg gtaagacacg    4620
acttatcgcc actggcagca gccactggta acaggattag cagagcgagg tatgtaggcg    4680
gtgctacaga gttcttgaag tggtggccta actacggcta cactagaagg acagtatttg    4740
gtatctgcgc tctgctgaag ccagttacct tcggaaaaag agttggtagc tcttgatccg    4800
gcaaacaaac caccgctggt agcggtggtt tttttgtttg caagcagcag attacgcgca    4860
gaaaaaaagg atctcaagaa gatcctttga tcttttctac ggggtctgac gctcagtgga    4920
acgaaaactc acgttaaggg attttggtca tgagattatc aaaaaggatc ttcacctaga    4980
tccttttaaa ttaaaaatga agttttaaat caatctaaag tatatatgag taaacttggt    5040
ctgacagtta ccaatgctta atcagtgagg cacctatctc agcgatctgt ctatttcgtt    5100
catccatagt tgcctgactc cccgtcgtgt agataactac gatacgggag ggcttaccat    5160
ctggccccag tgctgcaatg ataccgcgag acccacgctc accggctcca gatttatcag    5220
caataaacca gccagccgga agggccgagc gcagaagtgg tcctgcaact ttatccgcct    5280
ccatccagtc tattaattgt tgccgggaag ctagagtaag tagttcgcca gttaatagtt    5340
tgcgcaacgt tgttgccatt gctacaggca tcgtggtgtc acgctcgtcg tttggtatgg    5400
cttcattcag ctccggttcc caacgatcaa ggcgagttac atgatccccc atgttgtgca    5460
aaaaagcggt tagctccttc ggtcctccga tcgttgtcag aagtaagttg gccgcagtgt    5520
tatcactcat ggttatggca gcactgcata attctcttac tgtcatgcca tccgtaagat    5580
gcttttctgt gactggtgag tactcaacca agtcattctg agaatagtgt atgcggcgac    5640
cgagttgctc ttgcccggcg tcaatacggg ataataccgc gccacatagc agaactttaa    5700
aagtgctcat cattggaaaa cgttcttcgg ggcgaaaact ctcaaggatc ttaccgctgt    5760
tgagatccag ttcgatgtaa cccactcgtg cacccaactg atcttcagca tcttttactt    5820
tcaccagcgt ttctgggtga gcaaaaacag gaaggcaaaa tgccgcaaaa aagggaataa    5880
gggcgacacg gaaatgttga atactcatac tcttcctttt tcaatattat tgaagcattt    5940
atcagggtta ttgtctcatg agcggataca tatttgaatg tatttagaaa aataaacaaa    6000
taggggttcc gcgcacattt ccccgaaaag tgccacctga cgtctaagaa accattatta    6060
tcatgacatt aacctataaa aataggcgta tcacgaggcc ctttcgtctc gcgcgtttcg    6120
gtgatgacgg tgaaaacctc tgacacatgc agctcccgga gacggtcaca gcttgtctgt    6180
aagcggatgc cgggagcaga caagcccgtc agggcgcgtc agcgggtgtt ggcgggtgtc    6240
ggggctggct taactatgcg gcatcagagc agattgtact gagagtgcac catatgcggt    6300
gtgaaatacc gcacagatgc gtaaggagaa aataccgcat caggcgccat tcgccattca    6360
```

```
ggctgcgcaa ctgttgggaa gggcgatcgg tgcgggcctc ttcgctatta cgccagctgg    6420
cgaaaggggg atgtgctgca aggcgattaa gttgggtaac gccagggttt cccagtcac    6480 gacgttgtaa aacgacggcc agtgccacgc tctcccttat gcgactcctg cattaggaag    6540
cagcccagta gtaggttgag gccgttgagc accgccgccg caaggaatgg tgcatgcaag    6600
gagatggcgc ccaacagtcc cccggccacg gggcctgcca ccatacccac gccgaaacaa    6660
gcgctcatga gcccgaagtg gcgagcccga tcttccccat cggtgatgtc ggcgatatag    6720
gcgccagcaa ccgcacctgt ggcgccggtg atgccggcca cgatgcgtcc ggcgtagag     6779
```

<210> SEQ ID NO 5
<211> LENGTH: 6785
<212> TYPE: DNA
<213> ORGANISM: Artificial Sequence
<220> FEATURE:
<223> OTHER INFORMATION: This represents a retroviral vector derived
      from the murine stem cell virus

<400> SEQUENCE: 5

```
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
cctcactcgg cgcgccagtc tccgataga ctgcgtcgcc cgggtacccg tattcccaat    420
aaagcctctt gctgtttgca tccgaatcgt ggactgctg atccttggga gggtctcctc    480
agattgattg actgcccacc tcgggggtct ttcatttgga ggttccaccg agatttggag    540 accccctgcct agggaccacc gaccccccg ccgggaggta agctggccag cggtcgtttc    600
gtgtctgtct ctgtctttgt gcgtgtttgt gccggcatct aatgtttgcg cctgcgtctg    660
tactagttag ctaactagct ctgtatctgg cggaccccgtg gtggaactga cgagttctga    720
acacccggcc gcaaccctgg gagacgtccc agggactttg ggggccgttt tgtggcccg     780 acctgaggaa gggagtcgat gtggaatccg accccgtcag gatatgtggt tctggtagga    840
gacgagaacc taaaacagtt cccgcctccg tctgaatttt tgctttcggt ttggaaccga    900
agccgcgcgt cttgtctgct gcagcgctgc agcatcgttc tgtgttgtct ctgtctgact    960
gtgtttctgt atttgtctga aaattagggc cagactgtta ccactccctt aagtttgacc   1020
ttaggtcact ggaaagatgt cgagcggatc gctcacaacc agtcggtaga tgtcaagaag   1080
agacgttggg ttaccttctg ctctgcagaa tggccaacct ttaacgtcgg atggccgcga   1140
gacggcacct ttaaccgaga cctcatcacc caggttaaga tcaaggtctt ttcacctggc   1200
ccgcatggac acccagacca ggtccctac atcgtgacct gggaagcctt ggcttttgac   1260
ccccctccct gggtcaagcc ctttgtacac cctaagcctc cgcctcctct tcctccatcc   1320
gccccgtctc tcccccttga acctcctcgt tcgacccgc ctcgatcctc cctttatcca   1380
gccctcactc cttctctagg cgccgagatc tctcgaggtt gttggatcca ggaatggaca   1440
agattctgac agcaacgttt ttactcctag gccttcacct agctggggtg aatggccagc   1500
agcaggagaa acgtgaccag cagcaggtga cacaagtcc ccaatctctg acagtctggg   1560
aaggagagac cgcaattctg aactgcagtt atgaggacag cacttttaac tacttcccat   1620
ggtaccagca gttccctggg gaaggccctg cactcctgat atccatacgt tcagtgtccg   1680
```

```
ataaaaagga agatggacga ttcacaatct tcttcaataa aagggagaaa aagctctcct    1740
tgcacatcac agactctcag cctggagact cagctaccta cttctgtgca gcaagtgaca    1800
actatcagtt gatctggggc tctgggacca agctaattat aaagccagac atccagaacc    1860
cagaacctgc tgtgtaccag ttaaaagatc ctcggtctca ggacagcacc ctctgcctgt    1920
tcaccgactt tgactcccaa atcaatgtgc cgaaaaccat ggaatctgga cgttcatca    1980 ctgacaaaac tgtgctggac atgaaagcta tggattccaa gagcaatggg gccattgcct    2040
ggagcaacca gacaagcttc acctgccaag atatcttcaa agagaccaac gcccacctacc    2100 ccagttcaga cgttccctgt gatgccacgt tgaccgagaa aagctttgaa acagatatga    2160
acctaaactt tcaaaacctg tcagttatgg gactccgaat cctcctgctg aaagtagcgg    2220
gatttaacct gctcatgacg ctgaggctgt ggtccgaagc cagacacaaa cagaaaattg    2280
tggcaccggt gaaacagact ttgaattttg accttctcaa gttggcggga gacgtggagt    2340
ccaacccagg gcccatgtct aacactgtcc tcgctgattc tgcctggggc atcaccctgc    2400
tatcttgggt tactgtctttt ctcttgggaa caagttcagc agattctggg gttgtccagt    2460
ctccaagaca cataatcaaa gaaaaggag gaaggtccgt tctgacgtgt attcccatct    2520
ctggacatag caatgtggtc tggtaccagc agactctggg gaaggaatta aagttcctta    2580
ttcagcatta tgaaaggtg gagagagaca aaggattcct acccagcaga ttctcagtcc    2640
aacagtttga tgactatcac tctgaaatga acatgagtgc cttggaactg gaggactctg    2700
ctatgtactt ctgtgccagc tctcgggcca attatgaaca gtacttcggt cccggcacca    2760
ggctcacggt tttagaggat ctgagaaatg tgactccacc caaggtctcc ttgtttgagc    2820
catcaaaagc agagattgca aacaaacaaa aggctaccct cgtgtgcttg gccaggggct    2880
tcttccctga ccacgtggag ctgagctggt gggtgaatgg caaggaggtc cacagtgggg    2940
tcagcacgga ccctcaggcc tacaaggaga gcaattatag ctactgcctg agcagccgcc    3000
tgagggtctc tgctaccttc tggcacaatc ctcgaaacca cttccgctgc caagtgcagt    3060
tccatgggct ttcagaggag gacaagtggc cagagggctc acccaaacct gtcacacaga    3120
acatcagtgc agaggcctgg ggccgagcag actgtggaat cacttcagca tcctatcatc    3180 aggggttct gtctgcaacc atcctctatg agatcctact ggggaaggcc acccctatatg    3240 ctgtgctggt cagtggccta gtgctgatgg ccatggtcaa gaaaaaaaat tcctgagtcg    3300
acctgcagcc aagcttatcg ataaaataaa agattttatt tagtctccag aaaaaggggg    3360
gaatgaaaga ccccacctgt aggtttggca agctagctta agtaacgcca ttttgcaagg    3420
catggaaaat acataactga gaatagaaa gttcagatca aggttaggaa cagagagaca    3480
gcagaatatg ggccaaacag gatatctgtg gtaagcagtt cctgccccgg ctcagggcca    3540
agaacagatg gtccccagat gcggtcccgc cctcagcagt ttctagagaa ccatcagatg    3600
tttccagggt gccccaagga cctgaaaatg accctgtgcc ttatttgaac taaccaatca    3660
gttcgcttct cgcttctgtt cgcgcgcttc tgctccccga gctcaataaa agagcccaca    3720 accccctcact cggcgcgcca gtcctccgat agactgcgtc gcccgggtac ccgtgtatcc    3780
aataaaccct cttgcagttg catccgactt gtggtctcgc tgttccttgg gagggtctcc    3840
tctgagtgat tgactacccg tcagcggggg tctttcagta ttcgtaatca tggtcatagc    3900
tgtttcctgt gtgaaattgt tatccgctca caattccaca acatacga gccggaagca    3960 taaagtgtaa agcctgggt gcctaatgag tgagctaact cacattaatt gcgttgcgct    4020
cactgcccgc tttccagtcg ggaaacctgt cgtgccagct gcattaatga atcggccaac    4080
```

```
gcgcggggag aggcggtttg cgtattgggc gctcttccgc ttcctcgctc actgactcgc   4140
tgcgctcggt cgttcggctg cggcgagcgg tatcagctca ctcaaaggcg gtaatacggt   4200
tatccacaga tcaggggat aacgcaggaa agaacatgtg agcaaaaggc cagcaaaagg    4260
ccaggaaccg taaaaaggcc gcgttgctgg cgtttttcca taggctccgc ccccctgacg   4320
agcatcacaa aaatcgacgc tcaagtcaga ggtggcgaaa cccgacagga ctataaagat   4380
accaggcgtt tcccctgga agctccctcg tgcgctctcc tgttccgacc ctgccgctta    4440
ccggatacct gtccgccttt ctcccttcgg gaagcgtggc gctttctcat agctcacgct   4500
gtaggtatct cagttcggtg taggtcgttc gctccaagct gggctgtgtg cacgaacccc   4560
ccgttcagcc cgaccgctgc gccttatccg gtaactatcg tcttgagtcc aacccggtaa   4620
gacacgactt atcgccactg gcagcagcca ctggtaacag gattagcaga gcgaggtatg   4680
taggcggtgc tacagagttc ttgaagtggt ggcctaacta cggctacact agaaggacag   4740
tatttggtat ctgcgctctg ctgaagccag ttaccttcgg aaaaagagtt ggtagctctt   4800
gatccggcaa acaaaccacc gctggtagcg gtggtttttt tgtttgcaag cagcagatta   4860
cgcgcagaaa aaaaggatct caagaagatc ctttgatctt ttctacgggg tctgacgctc   4920
agtggaacga aaactcacgt taagggattt tggtcatgag attatcaaaa aggatcttca   4980
cctagatcct tttaaattaa aatgaagtt ttaaatcaat ctaaagtata tatgagtaaa    5040
cttggtctga cagttaccaa tgcttaatca gtgaggcacc tatctcagcg atctgtctat   5100
ttcgttcatc catagttgcc tgactccccg tcgtgtagat aactacgata cgggagggct   5160
taccatctgg ccccagtgct gcaatgatac cgcgagaccc acgctcaccg gctccagatt   5220
tatcagcaat aaaccagcca gccggaaggg ccgagcgcag aagtggtcct gcaactttat   5280
ccgcctccat ccagtctatt aattgttgcc gggaagctag agtaagtagt tcgccagtta   5340
atagtttgcg caacgttgtt gccattgcta caggcatcgt ggtgtcacgc tcgtcgtttg   5400
gtatggcttc attcagctcc ggttcccaac gatcaaggcg agttacatga tcccccatgt   5460
tgtgcaaaaa agcggttagc tccttcggtc ctccgatcgt tgtcagaagt aagttggccg   5520
cagtgttatc actcatggtt atggcagcac tgcataattc tcttactgtc atgccatccg   5580
taagatgctt ttctgtgact ggtgagtact caaccaagtc attctgagaa tagtgtatgc   5640
ggcgaccgag ttgctcttgc ccggcgtcaa tacgggataa taccgcgcca catagcagaa   5700
ctttaaaagt gctcatcatt ggaaaacgtt cttcggggcg aaaactctca aggatcttac   5760
cgctgttgag atccagttcg atgtaaccca ctcgtgcacc caactgatct tcagcatctt   5820
ttactttcac cagcgtttct gggtgagcaa aaacaggaag gcaaaatgcc gcaaaaaagg   5880
gaataagggc gacacggaaa tgttgaatac tcatactctt ccttttcaa tattattgaa    5940 gcatttatca gggttattgt ctcatgagcg gatacatatt tgaatgtatt tagaaaaata   6000
aacaaatagg ggttccgcgc acatttcccc gaaaagtgcc acctgacgtc taagaaacca   6060
ttattatcat gacattaacc tataaaaata ggcgtatcac gaggcccttt cgtctcgcgc   6120
gtttcggtga tgacggtgaa aacctctgac acatgcagct cccggagacg gtcacagctt   6180
gtctgtaagc ggatgccggg agcagacaag cccgtcaggg cgcgtcagcg ggtgttggcg   6240
ggtgtcgggg ctggcttaac tatgcggcat cagagcagat tgtactgaga gtgcaccata   6300
tgcggtgtga ataccgcac agatgcgtaa ggagaaaata ccgcatcagg cgccattcgc    6360
cattcaggct gcgcaactgt tgggaagggc gatcggtgcg ggcctcttcg ctattacgcc   6420
agctggcgaa agggggatgt gctgcaaggc gattaagttg ggtaacgcca gggttttccc   6480
```

```
agtcacgacg ttgtaaaacg acggccagtg ccacgctctc ccttatgcga ctcctgcatt    6540
aggaagcagc ccagtagtag gttgaggccg ttgagcaccg ccgccgcaag gaatggtgca    6600
tgcaaggaga tggcgcccaa cagtcccccg gccacggggc ctgccaccat acccacgccg    6660
aaacaagcgc tcatgagccc gaagtggcga gcccgatctt ccccatcggt gatgtcggcg    6720
atataggcgc cagcaaccgc acctgtggcg ccggtgatgc cggccacgat gcgtccggcg    6780
tagag                                                                6785
```

<210> SEQ ID NO 6
<211> LENGTH: 22
<212> TYPE: PRT
<213> ORGANISM: Artificial Sequence
<220> FEATURE:
<223> OTHER INFORMATION: This represents a 2A sequence derived from the
      foot-and-mouth disease virus

<400> SEQUENCE: 6

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 7
<211> LENGTH: 20
<212> TYPE: PRT
<213> ORGANISM: Artificial Sequence
<220> FEATURE:
<223> OTHER INFORMATION: This represents a 2A sequence derived from the
      equine rhinitis A virus

<400> SEQUENCE: 7

Gln Cys Thr Asn Tyr Ala Leu Leu Lys Leu Ala Gly Asp Val Glu Ser
1               5                   10                  15

Asn Pro Gly Pro
            20

<210> SEQ ID NO 8
<211> LENGTH: 18
<212> TYPE: PRT
<213> ORGANISM: Artificial Sequence
<220> FEATURE:
<223> OTHER INFORMATION: This represents a 2A sequence derived from the
      Thosea asigna virus

<400> SEQUENCE: 8

Glu Gly Arg Gly Ser Leu Leu Thr Cys Gly Asp Val Glu Glu Asn Pro
1               5                   10                  15

Gly Pro

<210> SEQ ID NO 9
<211> LENGTH: 19
<212> TYPE: PRT
<213> ORGANISM: Artificial Sequence
<220> FEATURE:
<223> OTHER INFORMATION: This represents a 2A sequence derived from the
      porcine teschovirus-1

<400> SEQUENCE: 9

Ala Thr Asn Phe Ser Leu Leu Lys Gln Ala Gly Asp Val Glu Glu Asn
1               5                   10                  15

Pro Gly Pro

```
<210> SEQ ID NO 10
<211> LENGTH: 6
<212> TYPE: PRT
<213> ORGANISM: Artificial Sequence
<220> FEATURE:
<223> OTHER INFORMATION: This represents a sequence of the C-terminus
      of a T cell receptor followed by an amino acid linker

<400> SEQUENCE: 10

Leu Trp Ser Ser Gly Pro
 1               5

<210> SEQ ID NO 11
<211> LENGTH: 5
<212> TYPE: PRT
<213> ORGANISM: Artificial Sequence
<220> FEATURE:
<223> OTHER INFORMATION: This represents a sequence of the C-terminus
      of a T cell receptor followed by an amino acid linker

<400> SEQUENCE: 11

Leu Trp Ser Gly Pro
 1               5

<210> SEQ ID NO 12
<211> LENGTH: 8
<212> TYPE: PRT
<213> ORGANISM: Artificial Sequence
<220> FEATURE:
<223> OTHER INFORMATION: This represents a sequence of the C-terminus
      of a T cell receptor followed by an amino acid linker

<400> SEQUENCE: 12

Leu Trp Ser Gly Ser Gly Ala Pro
 1               5

<210> SEQ ID NO 13
<211> LENGTH: 17
<212> TYPE: PRT
<213> ORGANISM: Artificial Sequence
<220> FEATURE:
<223> OTHER INFORMATION: This represents a sequence of the C-terminus
      of a T cell receptor followed by an amino acid linker

<400> SEQUENCE: 13

Leu Trp Ser Gly Ser Gly Glu Ala Arg His Lys Gln Lys Ile Val Ala
 1               5                  10                  15

Pro

<210> SEQ ID NO 14
<211> LENGTH: 8856
<212> TYPE: DNA
<213> ORGANISM: Artificial Sequence
<220> FEATURE:
<223> OTHER INFORMATION: This represents a retroviral vector derived
      from the murine stem cell virus

<400> SEQUENCE: 14
tgaaagaccc cacctgtagg tttggcaagc tagcttaagt aacgccattt tgcaaggcat      60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaaatgacc ctgtgcctta tttgaactaa ccaatcagtt    300
cgcttctcgc ttctgttcgc gcgcttctgc tccccgagct caataaaaga gcccacaacc    360
```

```
cctcactcgg cgcgccagtc ctccgataga ctgcgtcgcc cgggtacccg tattcccaat    420
aaagcctctt gctgtttgca tccgaatcgt ggactcgctg atccttggga gggtctcctc    480
agattgattg actgcccacc tcggggtct ttcatttgga ggttccaccg agatttggag     540 accctgcct agggaccacc gaccccccg ccgggaggta agctggccag cggtcgtttc      600
gtgtctgtct ctgtctttgt gcgtgtttgt gccggcatct aatgtttgcg cctgcgtctg    660
tactagttag ctaactagct ctgtatctgg cggacccgtg gtggaactga cgagttctga    720
acacccggcc gcaaccctgg gagacgtccc agggactttg ggggccgttt tgtggcccg     780 acctgaggaa gggagtcgat gtggaatccg accccgtcag gatatgtggt tctggtagga    840
gacgagaacc taaaacagtt cccgcctccg tctgaatttt tgctttcggt ttggaaccga    900
agccgcgcgt cttgtctgct gcagcgctgc agcatcgttc tgtgttgtct ctgtctgact    960
gtgtttctgt atttgtctga aaattagggc cagactgtta ccactcccttt aagtttgacc   1020 ttaggtcact ggaaagatgt cgagcggatc gctcacaacc agtcggtaga tgtcaagaag    1080
agacgttggg ttaccttctg ctctgcagaa tggccaacct ttaacgtcgg atggccgcga    1140
gacggcacct ttaaccgaga cctcatcacc caggttaaga tcaaggtctt ttcacctggc    1200
ccgcatggac acccagacca ggtcccctac atcgtgacct gggaagcctt ggcttttgac    1260 cccctccct gggtcaagcc cttttgtacac cctaagcctc cgcctcctct tcctccatcc    1320
gccccgtctc tccccttga acctcctcgt tcgacccgc ctcgatcctc cctttatcca      1380
gccctcactc cttctctagg cgccgagatc tggcgcgccc aattgatggt gttaagtttt    1440
ttgtacctgt tgacagccct tccgggtatc ctgtcagacg tgcagcttca ggagtcagga    1500
cctagcctcg tgaaaccttc tcagactctg tccctcacct gttctgtcac tggcgactcc    1560
atcaccagtg attattggag ctggatccgg aaattcccag ggaatagact tgagtacatg    1620
gggtacgtaa gctacagtgg tagcacgtac tacaatccat ctctcaaaag tcgaatctcc    1680
atcactcgag acacatccaa gaatcagtac tatctggacc tgaattctgt gactactgag    1740
gacacagcca catattactg tgcaaactgg gacggtgatt actggggcca agggactctg    1800
gtcactgtct ctgcagagag tcagtccttc ccaaatgtct ttcccctcgt ctcctgcgag    1860
agccccctgt ctgataagaa tctggtggcc atgggctgcc tggcccggga cttcctgccc    1920
agcaccattt ccttcacctg gaactaccag aacaacactg aagtcatcca gggtatcaga    1980
accttcccaa cactgaggac agggggcaag tacctagcca cctcgcaggt gttgctgtct    2040
cccaagagca tccttgaagg ttcagatgaa tacctggtat gcaaaatcca ctacggaggc    2100
aaaaacagag atctgcatgt gcccattcca gctgtcgcag agatgaaccc caatgtaaat    2160
gtgttcgtcc caccacggga tggcttctct ggccctgcac cacgcaagtc taaactcatc    2220
tgcgaggcca cgaacttcac tccaaaaccg atcacagtat cctggctaaa ggatgggaag    2280
ctcgtggaat ctggcttcac cacagatccg gtgaccatcg agaacaaagg atccacaccc    2340
caaacctaca aggtcataag cacacttacc atctctgaaa tcgactggct gaacctgaat    2400
gtgtacacct gccgtgtgga tcacaggggt ctcaccttct tgaagaacgt gtcctccaca    2460
tgtgctgcca gtccctccac agacatccta accttcacca tccccccctc ctttgccgac    2520
atcttcctca gcaagtccgc taacctgacc tgtctggtct caaacctggc aacctatgaa    2580
accctgaata tctcctgggc ttctcaaagt ggtgaaccac tggaaccaa aattaaaatc     2640 atggaaagcc atcccaatgg caccttcagt gctaagggtg tggctagtgt ttgtgtggaa    2700
gactggaata acaggaagga atttgtgtgt actgtgactc acagggatct gccttcacca    2760
```

```
cagaagaaat tcatctcaaa acccaatgag gtgcacaaac atccacctgc tgtgtacctg   2820
ctgccaccag ctcgtgagca actgaacctg agggagtcag ccacagtcac ctgcctggtg   2880
aagggcttct ctcctgcaga catcagtgtg cagtggcttc agagagggca actcttgccc   2940
caagagaagt atgtgaccag tgccccgatg ccagagcctg ggccccagg cttctacttt    3000 acccacagca tcctgactgt gacagaggag gaatggaact ccggagagac ctatacctgt   3060
gttgtaggcc acgaggccct gccacacctg gtgaccgaga ggaccgtgga caagtccact   3120 gaggggagg tgaatgctga ggaggaaggc tttgagaacc tgtggaccac tgcctccacc    3180
ttcatcgtcc tcttcctcct gagcctcttc tacagcacca ccgtcaccct gttcaaggtg   3240
aaagaagcca gacacaaaca gaaaattgtg gcaccggtga acagactttt gaattttgac   3300
cttctcaagt tggcgggaga cgtggagtcc aacccagggc ccatggtttt cacacctcag   3360
atacttggac ttatgctttt ttggatttca gcctccagag gtgatattgt gctaactcag   3420
tctccagcca ccctgtctgt gactccagga aatagcgtca gtctttcctg cagggccagc   3480
caaagtattg gcaacaacct acactggtat caacaaaaat cacatgagtc tccaaggctt   3540
ctcatcaagt atgcttccca gtccatctct gggatcccct ccaggttcag tggcagtgga   3600
tcagggacag atttcactct cagtatcaac agtgtggaga ctgaagattt tggaatgtat   3660
ttctgtcaac agagtaacag ctggccgtac acgttcggag gggggaccaa gctggaaata   3720
aaacgggctg atgctgcacc aactgtatcc atcttcccac catccagtga gcagttaaca   3780
tctggaggtg cctcagtcgt gtgcttcttg aacaacttct accccaaaga catcaatgtc   3840
aagtggaaga ttgatggcag tgaacgacaa aatggcgtcc tgaacagttg gactgatcag   3900
gacagcaaag acagcaccta cagcatgagc agcaccctca cgttgaccaa ggacgagtat   3960
gaacgacata cagctatac ctgtgaggcc actcacaaga catcaacttc acccattgtc     4020
aagagcttca acaggaatga gtgttagacg cgtgaattcc gccctctccc ctcccccccc   4080
cctaacgtta ctggccgaag ccgcttggaa taaggccggt gtgcgtttgt ctatatgtta   4140
ttttccacca tattgccgtc ttttggcaat gtgagggccc ggaaacctgg ccctgtcttc   4200
ttgacgagca ttcctagggg tctttcccct ctcgccaaag gaatgcaagg tctgttgaat   4260
gtcgtgaagg aagcagttcc tctggaagct tcttgaagac aaacaacgtc tgtagcgacc   4320
cttttgcagg cagcggaaccc cccacctggc gacaggtgcc tctgcggcca aaagccacgt   4380
gtataagata cacctgcaaa ggcggcacaa ccccagtgcc acgttgtgag ttggatagtt   4440
gtggaaagag tcaaatggct ctcctcaagc gtattcaaca aggggctgaa ggatgcccag   4500
aaggtacccc attgtatggg atctgatctg gggcctcggt gcacatgctt tacatgtgtt   4560
tagtcgaggt taaaaaacgt ctaggccccc cgaaccacgg ggacgtggtt ttcctttgaa   4620
aaacacgatg ataatatggc cacaaccatg gtgagcaagg gcgaggagct gttcaccggg   4680
gtggtgccca tcctggtcga gctggacggc gacgtaaacg gccacaagtt cagcgtgtcc   4740
ggcgagggcg agggcgatgc cacctacggc aagctgaccc tgaagttcat ctgcaccacc   4800
ggcaagctgc ccgtgccctg gcccacccte gtgaccaccc tgacctacgg cgtgcagtgc   4860
ttcagccgct accccgacca catgaagcag cacgacttct tcaagtccgc catgcccgaa   4920
ggctacgtcc aggagcgcac catcttcttc aaggacgacg gcaactacaa gacccgcgcc   4980
gaggtgaagt tcgagggcga caccctggtg aaccgcatcg agctgaaggg catcgacttc   5040
aaggaggacg gcaacatcct ggggcacaag ctggagtaca actacaacag ccacaacgtc   5100
tatatcatgg ccgacaagca gaagaacggc atcaaggtga acttcaagat ccgccacaac   5160
```

```
atcgaggacg gcagcgtgca gctcgccgac cactaccagc agaacacccc catcggcgac    5220
ggccccgtgc tgctgcccga caaccactac ctgagcaccc agtccgccct gagcaaagac    5280
cccaacgaga agcgcgatca catggtcctg ctggagttcg tgaccgccgc cgggatcact    5340
ctcggcatgg acgagctgta caagtaagtc gacctgcagc aagcttatc gataaaataa    5400
aagattttat ttagtctcca gaaaaagggg ggaatgaaag accccacctg taggtttggc    5460
aagctagctt aagtaacgcc attttgcaag gcatggaaaa tacataactg agaatagaga    5520
agttcagatc aaggttagga acagagagac agcagaatat gggccaaaca ggatatctgt    5580
ggtaagcagt tcctgccccg gctcagggcc aagaacagat ggtccccaga tgcggtcccg    5640
ccctcagcag tttctagaga accatcagat gtttccaggg tgccccaagg acctgaaaat    5700
gaccctgtgc cttatttgaa ctaaccaatc agttcgcttc tcgcttctgt tcgcgcgctt    5760
ctgctccccg agctcaataa aagagcccac aacccctcac tcggcgcgcc agtcctccga    5820
tagactgcgt cgcccgggta cccgtgtatc caataaaccc tcttgcagtt gcatccgact    5880
tgtggtctcg ctgttccttg ggagggtctc ctctgagtga ttgactaccc gtcagcgggg    5940
gtctttcagt attcgtaatc atggtcatag ctgtttcctg tgtgaaattg ttatccgctc    6000
acaattccac acaacatacg agccggaagc ataaagtgta aagcctgggg tgcctaatga    6060
gtgagctaac tcacattaat tgcgttgcgc tcactgcccg ctttccagtc gggaaacctg    6120
tcgtgccagc tgcattaatg aatcggccaa cgcgcgggga gaggcggttt gcgtattggg    6180
cgctcttccg cttcctcgct cactgactcg ctgcgctcgg tcgttcggct gcggcgagcg    6240
gtatcagctc actcaaaggc ggtaatacgg ttatccacag aatcagggga taacgcagga    6300
aagaacatgt gagcaaaagg ccagcaaaag gccaggaacc gtaaaaaggc cgcgttgctg    6360
gcgtttttcc ataggctccg ccccctgac gagcatcaca aaaatcgacg ctcaagtcag    6420
aggtggcgaa acccgacagg actataaaga taccaggcgt ttccccctgg aagctccctc    6480
gtgcgctctc ctgttccgac cctgccgctt accggatacc tgtccgcctt tctcccttcg    6540
ggaagcgtgg cgctttctca tagctcacgc tgtaggtatc tcagttcggt gtaggtcgtt    6600
cgctccaagc tgggctgtgt gcacgaaccc cccgttcagc ccgaccgctg cgccttatcc    6660
ggtaactatc gtcttgagtc aacccggta agacacgact tatcgccact ggcagcagcc    6720
actggtaaca ggattagcag agcgaggtat gtaggcggtg ctacagagtt cttgaagtgg    6780
tggcctaact acggctacac tagaaggaca gtatttggta tctgcgctct gctgaagcca    6840
gttaccttcg gaaaaagagt tggtagctct tgatccggca acaaaccac cgctggtagc    6900
ggtggttttt tgtttgcaa gcagcagatt acgcgcagaa aaaaggatc tcaagaagat    6960
cctttgatct tttctacggg gtctgacgct cagtggaacg aaaactcacg ttaagggatt    7020
ttggtcatga gattatcaaa aaggatcttc acctagatcc ttttaaatta aaatgaagt    7080
tttaaatcaa tctaaagtat atatgagtaa acttggtctg acagttacca atgcttaatc    7140
agtgaggcac ctatctcagc gatctgtcta tttcgttcat ccatagttgc ctgactcccc    7200
gtcgtgtaga taactacgat acgggagggc ttaccatctg gccccagtgc tgcaatgata    7260
ccgcgagacc cacgctcacc ggctccagat ttatcagcaa taaaccagcc agccggaagg    7320
gccgagcgca gaagtggtcc tgcaacttta tccgcctcca tccagtctat taattgttgc    7380
cgggaagcta gagtaagtag ttcgccagtt aatagtttgc gcaacgttgt tgccattgct    7440
acaggcatcg tggtgtcacg ctcgtcgttt ggtatggctt cattcagctc cggttcccaa    7500
cgatcaaggc gagttacatg atccccatg ttgtgcaaaa aagcggttag ctccttcggt    7560
```

```
cctccgatcg ttgtcagaag taagttggcc gcagtgttat cactcatggt tatggcagca    7620
ctgcataatt ctcttactgt catgccatcc gtaagatgct tttctgtgac tggtgagtac    7680
tcaaccaagt cattctgaga atagtgtatg cggcgaccga gttgctcttg cccggcgtca    7740
atacgggata ataccgcgcc acatagcaga actttaaaag tgctcatcat tggaaaacgt    7800
tcttcggggc gaaaactctc aaggatctta ccgctgttga gatccagttc gatgtaaccc    7860
actcgtgcac ccaactgatc ttcagcatct tttactttca ccagcgtttc tgggtgagca    7920
aaaacaggaa ggcaaaatgc cgcaaaaaag gaataaggg cgacacggaa atgttgaata     7980
ctcatactct cctttttca atattattga agcatttatc agggttattg tctcatgagc     8040
ggatacatat ttgaatgtat ttagaaaaat aaacaaatag gggttccgcg cacatttccc    8100
cgaaaagtgc cacctgacgt ctaagaaacc attattatca tgacattaac ctataaaaat    8160
aggcgtatca cgaggccctt tcgtctcgcg cgtttcggtg atgacggtga aaacctctga    8220
cacatgcagc tcccggagac ggtcacagct tgtctgtaag cggatgccgg gagcagacaa    8280
gcccgtcagg gcgcgtcagc gggtgttggc gggtgtcggg gctggcttaa ctatgcggca    8340
tcagagcaga ttgtactgag agtgcaccat atgcggtgtg aaataccgca cagatgcgta    8400
aggagaaaat accgcatcag gcgccattcg ccattcaggc tgcgcaactg ttgggaaggg    8460
cgatcggtgc gggcctcttc gctattacgc cagctggcga aggggggatg tgctgcaagg    8520
cgattaagtt gggtaacgcc agggttttcc cagtcacgac gttgtaaaac gacggccagt    8580
gccacgctct cccttatgcg actcctgcat taggaagcag cccagtagta ggttgaggcc    8640
gttgagcacc gccgccgcaa ggaatggtgc atgcaaggag atggcgccca acagtccccc    8700
ggccacgggg cctgccacca tacccacgcc gaaacaagcg ctcatgagcc cgaagtggcg    8760
agcccgatct tccccatcgg tgatgtcggc gatataggcg ccagcaaccg cacctgtggc    8820
gccggtgatg ccggccacga tgcgtccggc gtagag                              8856
```

METHOD FOR THE GENERATION OF ANTIGEN-SPECIFIC LYMPHOCYTES

RELATED APPLICATIONS

This is a continuation-in-part application that claims the benefit of U.S. patent application Ser. No. 10/789,938, filed Feb. 27, 2004, now abandoned which is a continuation-in-part application and claims the benefit of U.S. patent application Ser. No. 10/317,078, filed Dec. 10, 2002, now abandoned. U.S. patent application Ser. No. 10/317,078 in turn claims the benefit under 35 U.S.C. §119(e) of U.S. Provisional Application No. 60/339,375, filed Dec. 10, 2001 and U.S. Provisional Application No. 60/394,803, filed Jul. 8, 2002. Each of the priority applications is hereby incorporated by reference in their entirety.

STATEMENT OF GOVERNMENT SUPPORT

This invention was made with government support under R01 GM39458 awarded by the National Institutes of Health. The government has certain rights in the invention.

BACKGROUND OF THE INVENTION

1. Field of the Invention

The invention relates generally to the fields of gene delivery and immunology, and more particularly to the delivery of genetic material to cells of the immune system.

2. Description of the Related Art

The adaptive immune system of vertebrates defends the host against infection. T cells play the role of central organizer of the immune response by recognizing antigens through T cell receptors (TCR). The specificity of a T cell depends on the sequence of its T cell receptor. The genetic template for this receptor is created during T cell development in the thymus by the V(D)J DNA rearrangement process, which imparts a unique antigen specificity upon each TCR. The TCR plays an essential role in T cell function, development and survival. Genetic lesions that interfere with the generation of antigen receptors block T cell development and result in immunodeficiencies. Because of the importance of T cells in organizing the immune response, it is desirable to be able to generate T cells having a particular antigen specificity.

B cells are also very important to the host immune response. B cells produce antibodies that bind to specific antigens on immune cell targets that can facilitate, for example, phagocytosis or complement-mediated lysis of the immune cell target.

Currently, the only available method for the generation of an animal having a T cell with a defined antigen specificity is to introduce the gene encoding the desired T cell receptor into an embryo by pronuclear injection. This technique requires handling a large fragment of genomic DNA encoding the rearranged α and β chains of the TCR, a significant amount of time, and can only be practiced in limited genetic backgrounds. Moreover, such a technique is not suitable for therapeutic applications.

The introduction of a TCR into peripheral blood cells has been reported recently (P. A. Moss (2001) Nature Immunology 2, 900-901; Kessels et al. (2001) Nature Immunology 2, 957-961 and Stanislawski et al. (2001) Nature Immunology 2, 962-970). In these studies, TCRα and TCRβ genes were introduced and stably expressed in mature T cells that had been activated with a mitogen and then infected with a retroviral vector. Using this approach, T cells derived from non-specific, heterogeneous populations were converted into T cells capable of responding to protein antigens and tumor tissues. However, these methods do not produce lymphocytes having a well-defined antigen-specificity. Importantly, the T cells that are engineered to express the TCRs are activated mature cells that already express an endogenous TCR of unknown specificity. Thus the introduction of transgenic TCRα and β chains will lead to the heterologous combinations with the endogenous chains. These heterologous TCRs will have unpredictable specificity and may produce autoimmune damage. Furthermore, the effector function of the engineered cells is defined by the conditions under which these cells are activated in vitro, which will limit the type of immune responses they can induce. In addition, only a fraction of activated T cells have the capacity to persist in vivo for an extended period of time.

Berg et al., 1988 reported production of a TCRβ transgenic mouse and Bluthman et al., 1988 reported a whole TCR transgenic mouse. The generation of TCR transgenic animals has also been reported by Uematsu et al. (1988), Pircher et al. (1989), Mamalaki et al. (1993), Kouskoff et al. (1995), and Barnden et al. (1998).

A number of reports also address the need in the art for methods that can be used to generate T cells having a defined specificity, including: Dembic et al., 1986; Clay et al., 1999; Fujio et al., Immunol 2000 Jul. 1; Kessels et al., Immunol 2001 Oct.; Stanislawski et al., Immunol 2001 Oct.; Cooper et al., Virol., 2000; and Moss, Immunol 2001 Oct.

Recently, adoptive T cell therapy using antigen-specific T cell clones has been used successfully for the treatment of cancer (Dudley et al. Science 298:850-854 (2002); Yee et al. Proc. Natl. Acad. Sci. USA, Early Edition 10.1073/pnas.242600099 (2002)).

Because of the importance of antigen specific T cells and B cells to the immune response and their usefulness in treating disease, there is a great need for techniques that enable the production of transgenic cells that have a defined antigen specificity. There is also a great need to deliver multiple genes using a multicistronic polynucleotide delivery system. This invention addresses this and other needs in the art.

SUMMARY OF THE INVENTION

The invention provides methods for the generation of lymphocytes having unique antigen specificity. Lymphocytes generated according to the methods of the invention have a number of utilities, including therapeutic applications, such as priming an organism's immune response against a pathogen, and providing an immune response against a particular disease or disorder, such as diseased tissue, for example, cancerous tissue.

According to the preferred embodiment of the invention, an antigen-specific polynucleotide is introduced into a target cell by contacting the target cell with a polynucleotide delivery system comprising the antigen-specific polynucleotide. A polynucleotide delivery system is any system capable of introducing a polynucleotide into a target cell. Polynucleotide delivery systems include both viral and non-viral delivery systems. In one embodiment, the polynucleotide delivery system comprises a retroviral vector, for example, a vector based on the murine stem cell virus ("MSCV"). A target cell is preferably a mammalian stem cell or stem cell line, including, without limitation, heterogeneous populations of cells that comprise stem cells. The stem cells can be, for example, hematopoietic stem cells. In one embodiment, the target cells are primary bone marrow cells.

According to the methods of the invention, the polynucleotide delivery system can be used to contact the target cells either in vivo or in vitro (i.e., ex vivo). The methods of the invention can be used with target cells from any mammal, including, without limitation, humans. A target cell can be removed from a host organism and contacted with the antigen-specific polynucleotide and the polynucleotide delivery system. It is also possible to introduce the antigen-specific polynucleotide and polynucleotide delivery system directly into a host organism, and more preferably into the bone marrow of a host organism.

In one aspect, the present invention provides a method of generating a lymphocyte with a unique antigen specificity in a mammal by contacting a mammalian stem cell with a polynucleotide delivery system comprising an antigen-specific polynucleotide, preferably a cDNA. The stem cell is then transferred into the mammal. The antigen-specific polynucleotide preferably encodes an antigen-specific polypeptide.

According to one embodiment the mammalian stem cell is contacted with the polynucleotide delivery system in vitro.

In one embodiment the antigen-specific polypeptide is a T cell receptor, preferably comprising an α subunit and a β subunit. In another embodiment the T cell receptor is a hybrid T cell receptor.

In other embodiments, the antigen-specific polypeptide is an antibody, preferably comprising light chains and heavy chains.

In another embodiment the polynucleotide delivery system is preferably a modified retrovirus, more preferably a modified lentivirus.

The polynucleotide delivery system preferably comprises a third gene that enhances immune cell function. In one aspect, the third gene preferably enhances T cell function. In another aspect, the third gene preferably enhances B cell function. Expression of the third gene can be preferably linked to expression of the T cell receptor α and β subunits. Expression of the third gene can be preferably linked to expression of heavy and light chains of an antibody in other embodiments. The third gene may enhance immune cell function by making the immune cells more reactive to antigen. In other embodiments the third gene may provide a way to detect cells expressing an element of interest, such as a T cell receptor or an antibody. In still other embodiments the third gene may be a safety gene that allows for the targeting and destruction of cells expressing the antigen specific polypeptide. In further embodiments the third gene may aid in treating or preventing a disease or disorder. Additional genes that enhance immune cell function may also be present.

The mammalian stem cell is preferably a hematopoietic stem cell, more preferably a primary bone marrow cell. The stem cell may be obtained from the mammal in which the lymphocyte is to be generated.

In one embodiment the mammalian stem cells are transferred into the mammal by injection into the peripheral blood.

The invention also provides a lymphocyte having a defined antigen specificity generated according to the methods of the invention.

In another aspect, the invention provides methods of stimulating an immune response to an antigen in a mammal by harvesting primary bone marrow cells from the mammal, contacting the primary bone marrow cells with a polynucleotide delivery system comprising an antigen-specific polynucleotide and transferring the cells back into the mammal.

The antigen-specific polypeptide preferably encodes a T cell receptor that specifically binds to an antigen to which an immune response is desired. The T cell receptor comprises an α subunit and a β subunit. The T cell receptor may be a hybrid T cell receptor.

In one embodiment the immune response is enhanced by stimulating the T cells with antigen in vivo. For example, purified antigen may be injected into the mammal.

In another embodiment the polynucleotide delivery system preferably comprises a modified retrovirus, more preferably a modified lentivirus.

In another embodiment, the polynucleotide delivery system is a tricistronic system that comprises an antigen specific polynucleotide and an IRES or a 2A element.

In a further aspect the invention provides methods of treating cancer in a patient by identifying an antigen associated with the cancer, obtaining a polynucleotide that encodes a T cell receptor that specifically binds the antigen, contacting mammalian stem cells with a polynucleotide delivery system comprising the polynucleotide and transferring the stem cells into the patient. In one embodiment the stem cells are hematopoietic stem cells, preferably primary bone marrow cells from a mammal. The T cell receptor may comprise an α subunit and a β subunit.

In another embodiment a T cell that expresses the T cell receptor on its surface is cloned from the patient and expanded in vitro. The expanded cells are then transferred back into the patient.

In another embodiment T cells that express the desired T cell receptor on their surface are expanded in vivo by challenge with antigen that the T cell receptor specifically recognizes.

In another aspect the invention provides methods of preventing infection in a mammal that has been or is expected to be exposed to an infectious agent. Primary bone marrow cells are harvested from the mammal and contacted with a polynucleotide delivery system comprising an antigen-specific polynucleotide. The primary bone marrow cells are then transferred back to the mammal. Preferably the antigen specific polynucleotide encodes a T cell receptor that specifically binds to an antigen that is associated with the infectious agent. The infectious agent may be, for example, HIV.

The invention also provides transgenic animals having lymphocytes with defined antigen-specificity. In one embodiment, a transgenic, non-human mammal is produced by contacting a mammalian stem cell with a polynucleotide delivery system comprising an antigen-specific polypeptide in vitro and transferring the hematopoietic stem cell into the mammal. The antigen specific polynucleotide encodes an antigen-specific polypeptide, such as a T cell receptor, with the desired antigen specificity.

Figure 2:
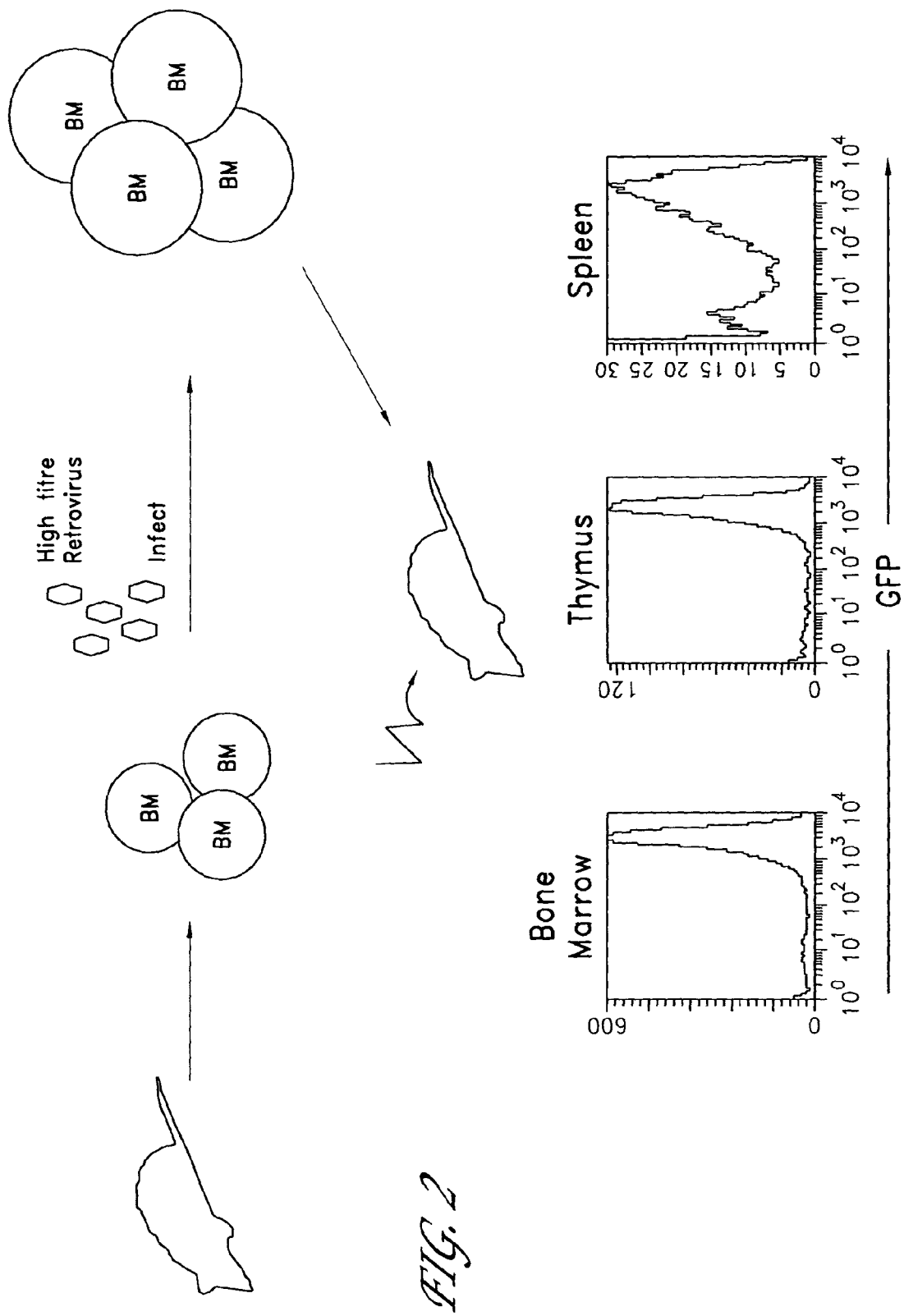

FIG. 2 shows a diagram of the strategy to generate TCR transgenic T cells using retrovirus-based gene delivery into bone marrow ("BM") stem cells. Hematopoietic precursor cells were obtained from wild type and IL-2 deficient RAG knockout mice that had been treated with 5-fluorouracil. These cells were then cultured in the presence of cytokines and co-infected with MIG retroviruses expressing the cDNA for the OTII TCRα or β chain. The infected hematopoietic precursor cells were then transferred into a lethally irradiated host mouse and allowed to reconstitute the immune system. Cells expressing the retrovirally-encoded genes were identified by their expression of the green fluorescent protein.

Figure 3A:
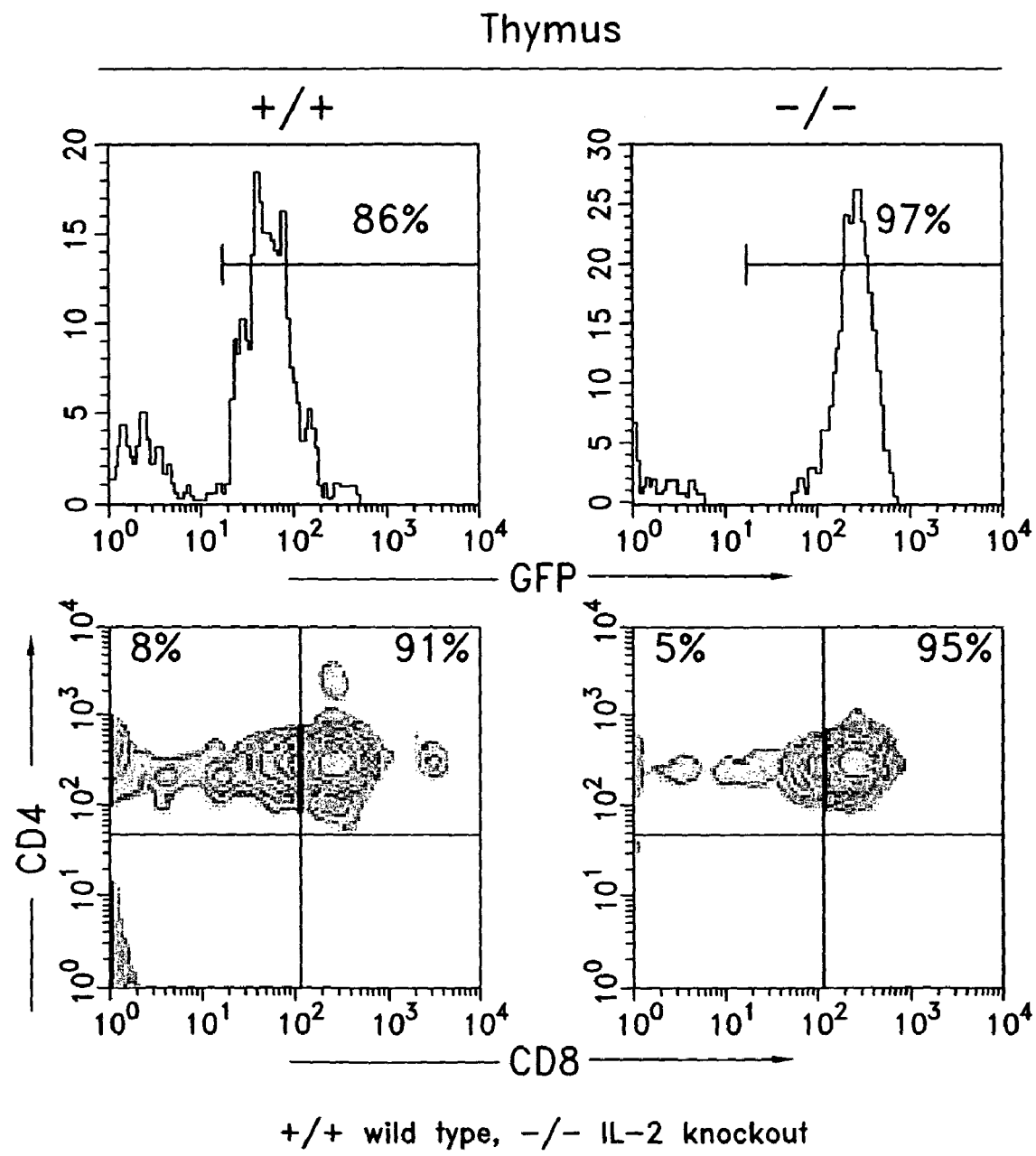

FIG. 3A shows the normal development of OTII TCR transgenic CD4+ T cells in the thymus of mice receiving retrovirally-transduced bone marrow stem cells. Thymocytes obtained from lethally-irradiated host mice 11 weeks after injection of retrovirally-transduced hematopoietic precursor cell were stained with anti-CD4-Cyc and anti-CD8-PE antibodies and analyzed by flow cytometry. The distribution of CD4 and CD8 expression on GFP+ thymocytes is shown.

Figure 3B:
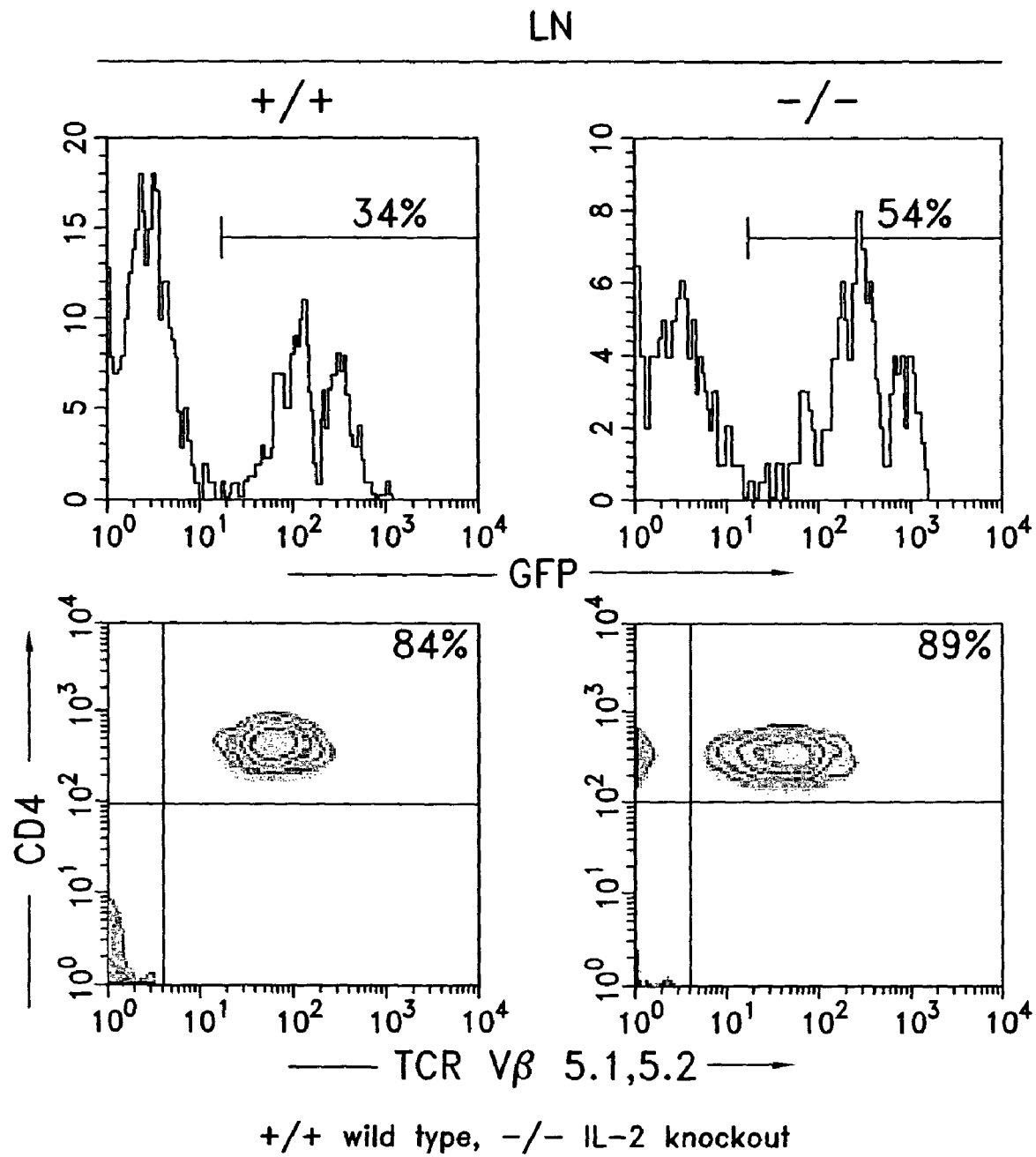

FIG. 3B shows the presence of mature OTII TCR transgenic CD4+ T cells in the peripheral lymphoid organs of mice receiving retrovirally-transduced bone marrow stem cells. Lymph node and spleen (not shown) cells obtained from lethally irradiated host mice 11 weeks after injection of retrovirally-transduced hematopoietic precursor cells were stained with anti-CD4-Cyc and anti-TCR Vβ 5.1,5.2-PE antibodies and analyzed by flow cytometry. The distribution of CD4 and Vβ5.1,5.2 expression on GFP+ lymph node cells is shown.

Figure 3C:
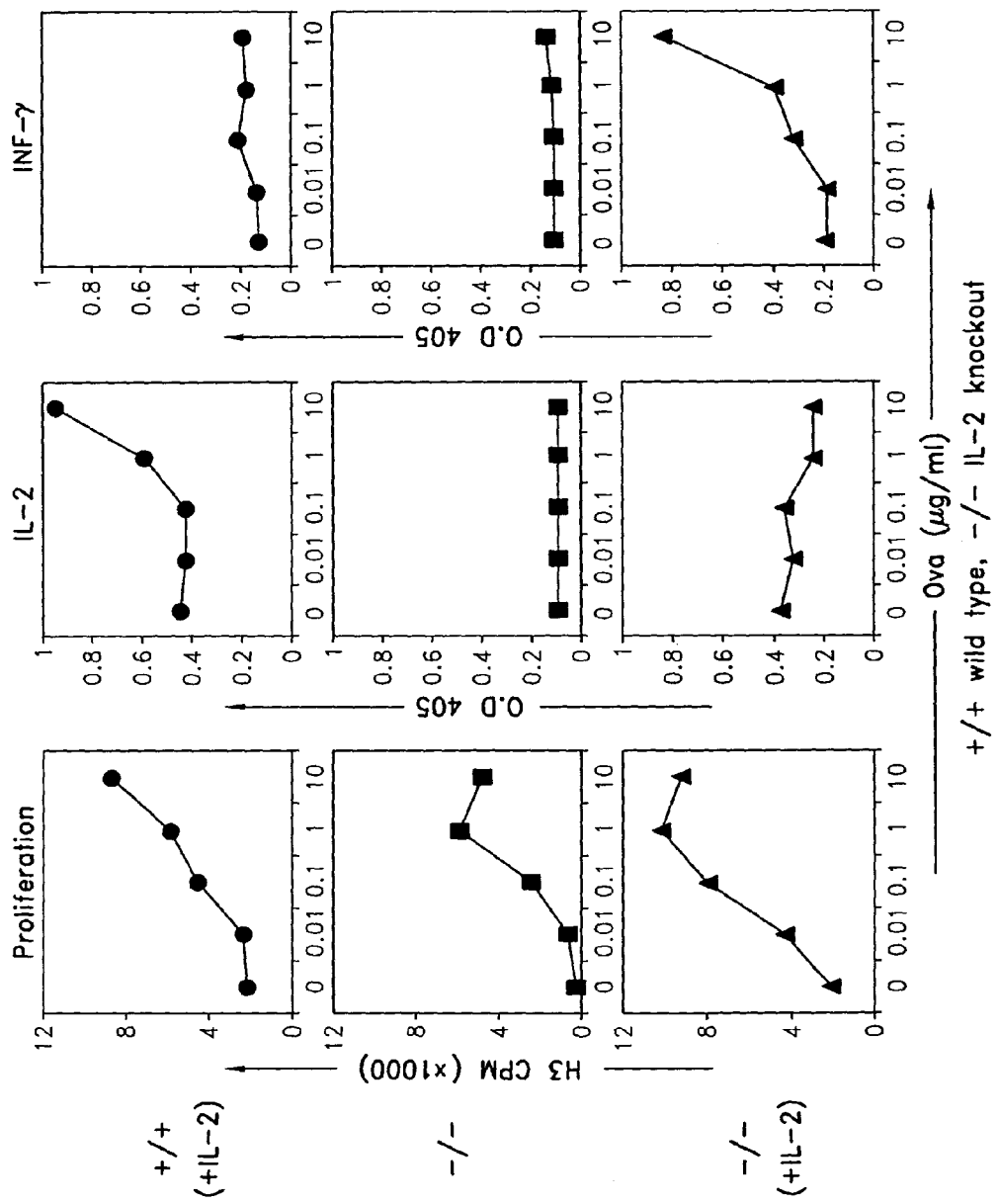

FIG. 3C shows normal functional responses of OTII TCR transgenic CD4+ T cells obtained from the peripheral lymphoid organs of mice receiving retrovirally-transduced bone marrow stem cells. Spleen cells obtained from lethally irradiated host mice 11 weeks after injection of retrovirally-transduced hematopoietic precursor cells derived from IL-2 deficient mice were supplemented with B6 spleen cells as APCs and stimulated in vitro with OVAp in the presence or absence of exogenous IL-2. Proliferation was assayed after 72 hours by $^3$H-thymidine incorporation and cytokine production by ELISA. Data was normalized for the number of GFP+CD4+TCR Vβ5.1,5.2+ cells present in the starting spleen cell populations. Proliferation and cytokine production was seen with wild type OTII T cells both in the presence and absence of IL-2 (data not shown).

Figure 4A:
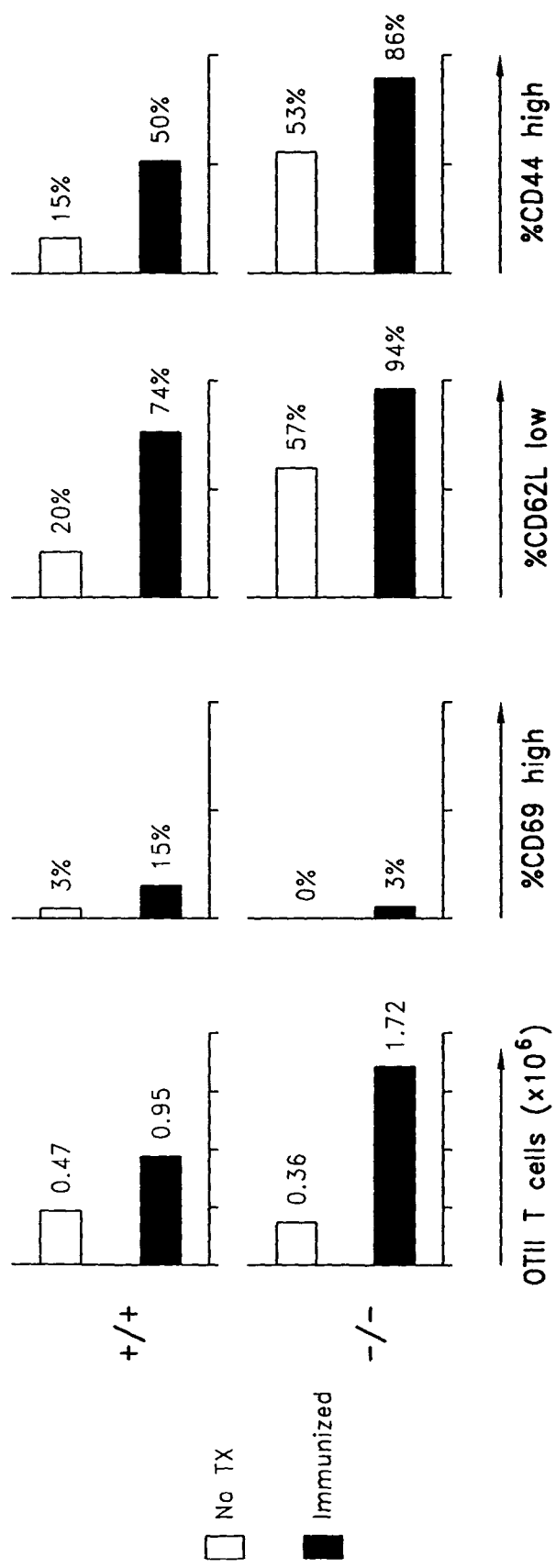

FIG. 4A shows the normal cell expansion and expression of activation following in vivo antigen stimulation of OTII TCR transgenic CD4+ T cells in the peripheral lymphoid organs of mice receiving retrovirally-transduced bone marrow stem cells. Lethally-irradiated host mice were immunized via an intra peritoneal injection of 200 μg OVAp or left untreated (No TX) 10 weeks after receiving retrovirally-transduced hematopoietic precursor cells. Spleen and lymph node cells were harvested and counted 6 days later. An aliquot of these cells was stained with anti-CD4-Cyc and anti-TCR Vβ 5.1, 5.2-PE, anti-CD62L-PE or anti-CD44-PE antibodies and analyzed by flow cytometry. The number of OTII TCR transgenic T cells present in the spleen and lymph nodes of immunized and control mice was determined by multiplying the percentage of GFP+CD4+TCR Vβ5.1,5.2+ cells by the total number of cells present in these organs. The frequency of activated T cells was determined by gating on GFP+CD4+ TCR Vβ 5.1,5.2_ and CD62L low or CD44 high cells.

Figure 4B:
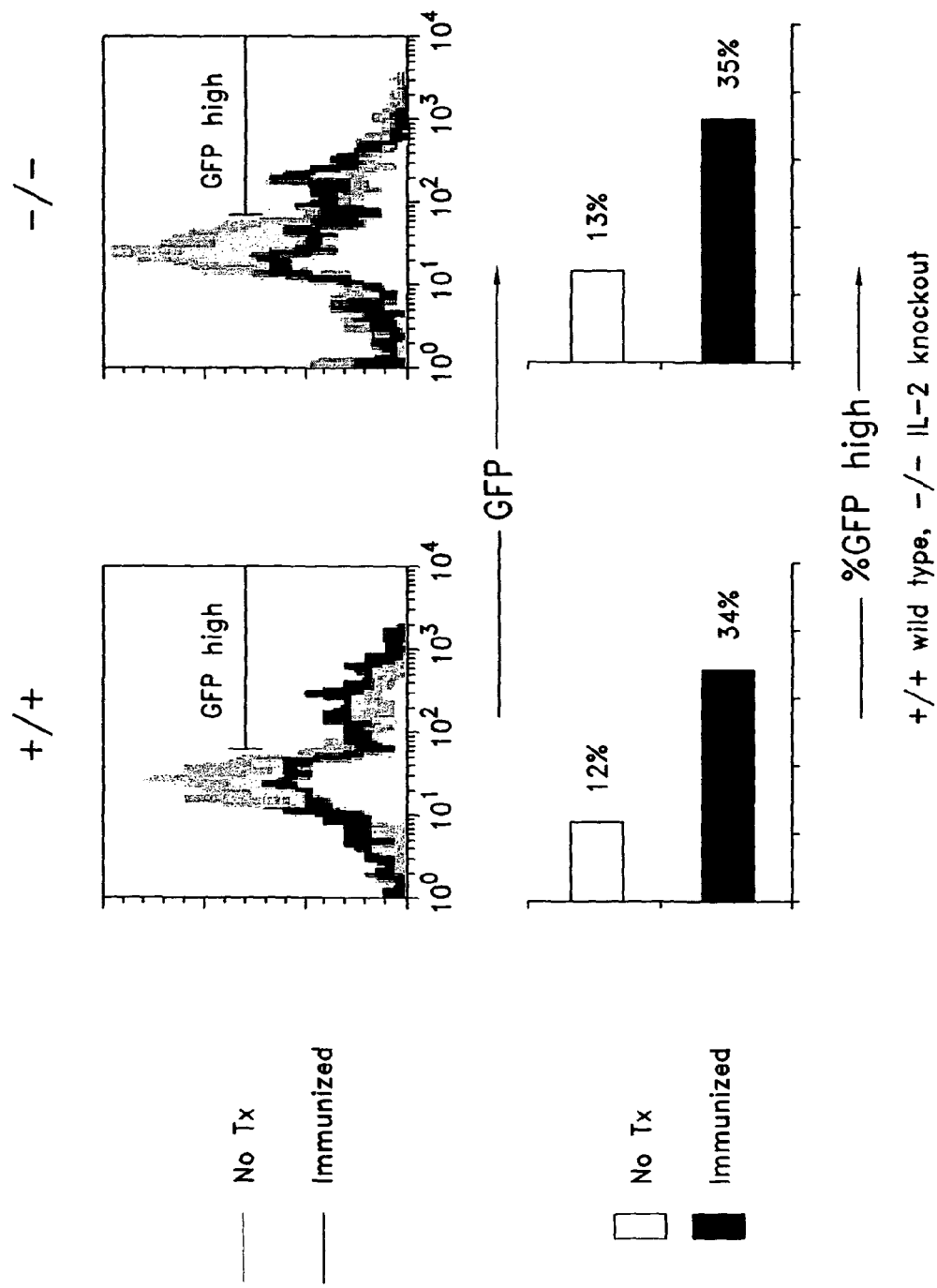

FIG. 4B shows the preferential expansion of GFP$^{high}$ OTII TCR transgenic CD4+ T cells following stimulation with antigen in vivo. Mice receiving retrovirally-transduced hematopoietic precursor cells were immunized as in (A). Spleen and lymph node cells were collected and stained with anti-CD4-Cyc and anti-TCR Vβ 5.1,5.2-PE antibody and analyzed by flow cytometry. The expression of GFP in Vβ5.1, 5.2_ CD4+ OTII T cells, and the frequency of GFP$^{high}$ OTII T cells is shown.

Figure 4C:
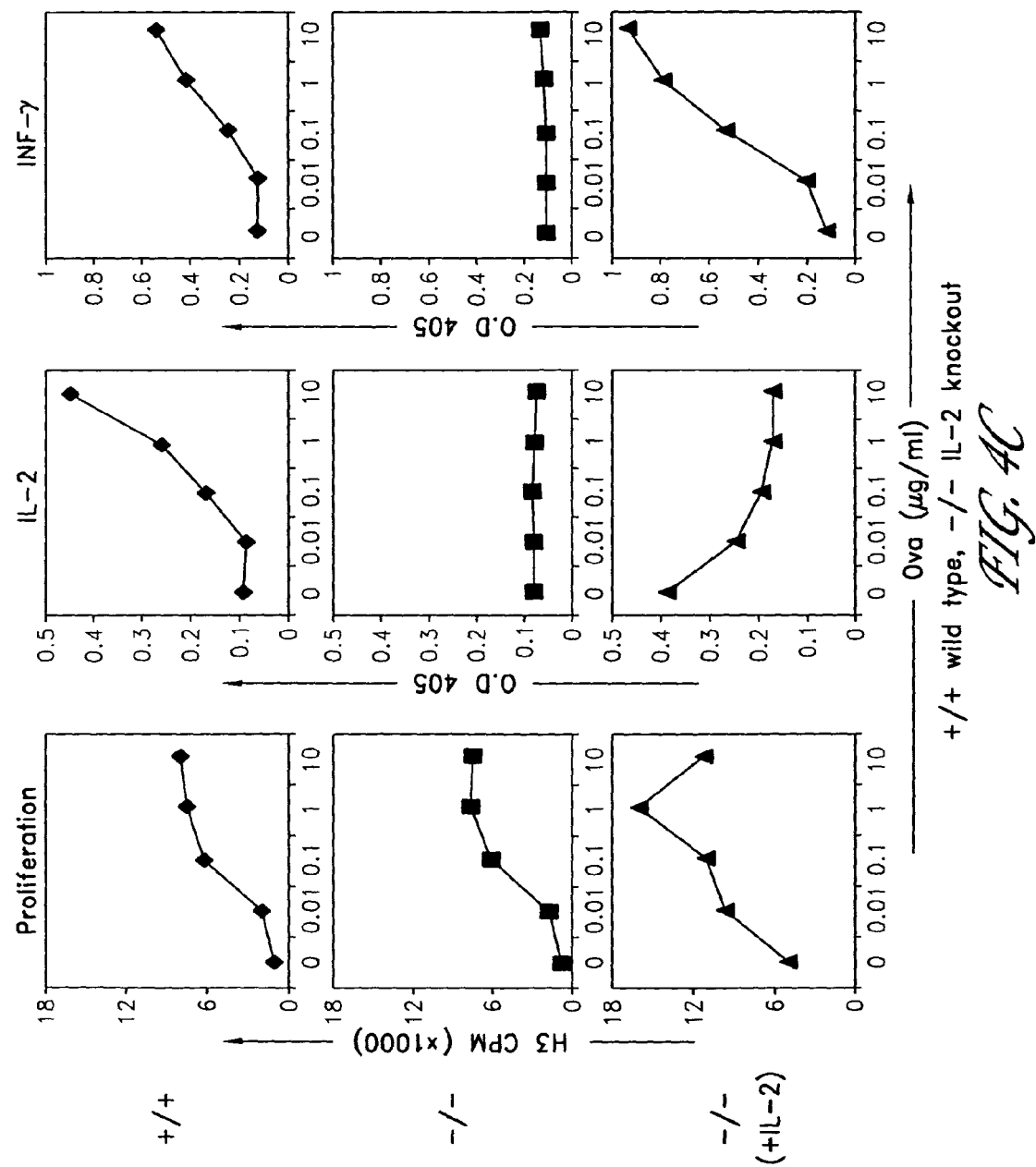

FIG. 4C shows normal functional responses of OTII TCR transgenic CD4+ T cells following in vivo stimulation with antigen. Mice receiving retrovirally-transduced hematopoietic precursor cells were immunized as in (A). Spleen/LN cells were harvested and stimulated in vitro with OVAp in the presence of B6 spleen cells as APCs. Proliferation was assayed by $^3$H-thymidine incorporation, cytokines by ELISA. Data was normalized for the number of GFP+ CD4+ TCR Vβ5.1,5.2+ cells present in the starting spleen cell populations.

FIGS. 5A and B provide the sequence of a MIG retroviral construct (SEQ ID NO: 1).

Figure 6A:
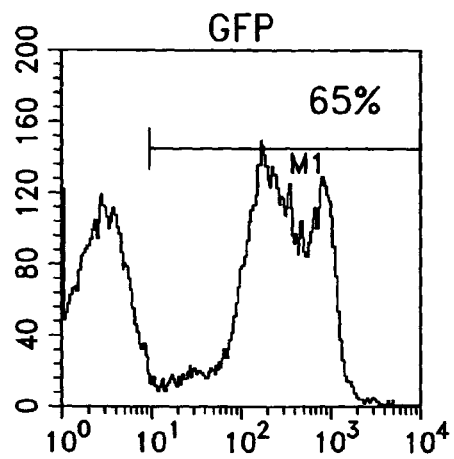
Figure 6B:
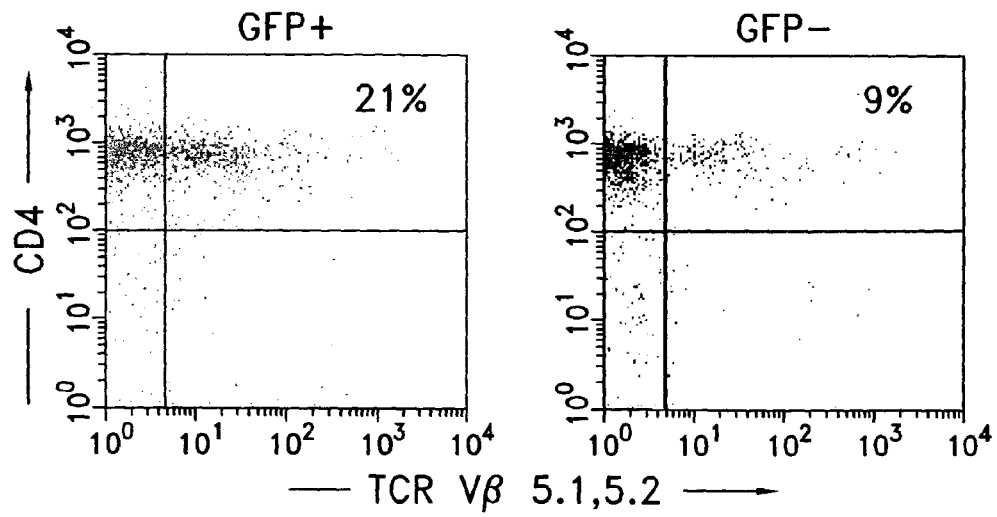
Figure 6C:
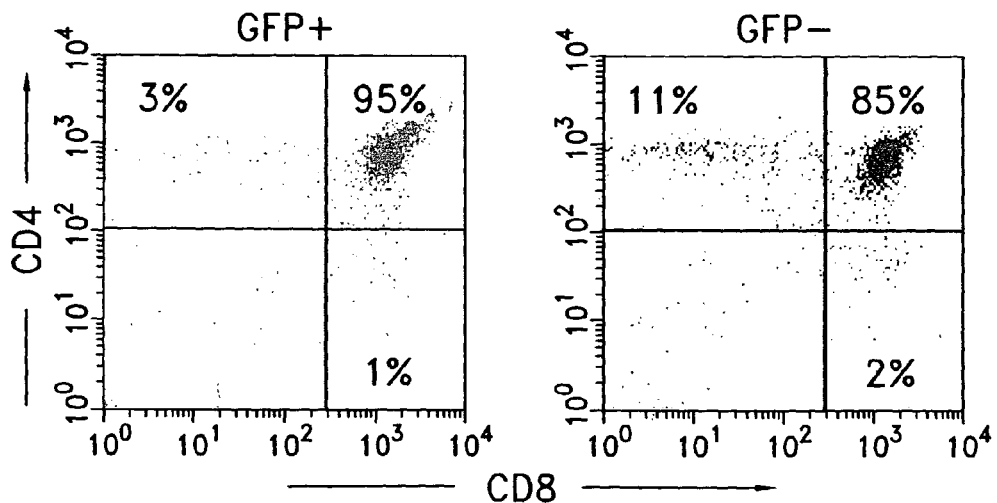

FIGS. 6A, 6B, and 6C show that retrovirus mediated transfer into bone marrow from wild type mice generates thymocytes expressing transgenic OTII TCR. Cells were obtained from the thymus of mice that received wild type bone marrow infected with recombinant retrovirus. Cells were analyzed for expression of GFP, TCR β, CD4 and CD8.

Figure 7A:
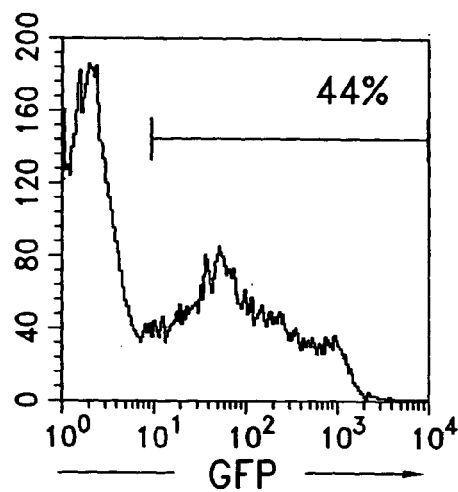
Figure 7B:
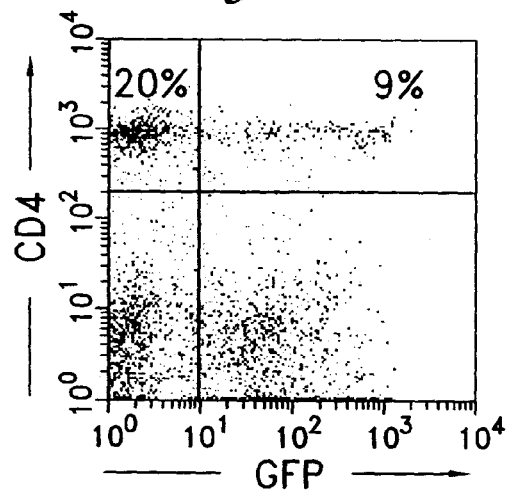
Figure 7C:
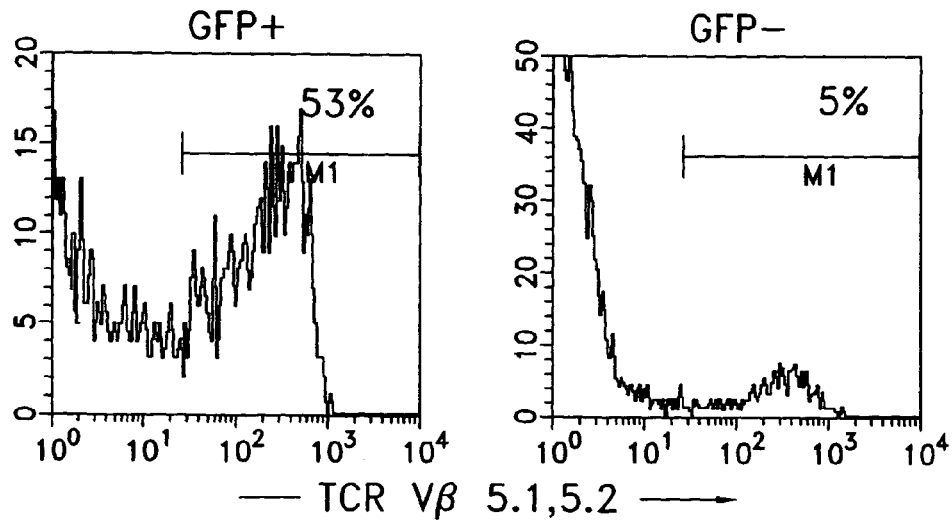

FIGS. 7A, 7B, and 7C show that retrovirus mediated transfer into bone marrow from wild type mice generates mature CD4+ T cells that express transgenic TCR in the periphery. Cells were obtained from the peripheral lymph nodes of mice receiving wild type bone marrow that had been infected with recombinant retrovirus. Cells were analyzed for GFP, CD4 and TCRβ expression.

Figure 8:
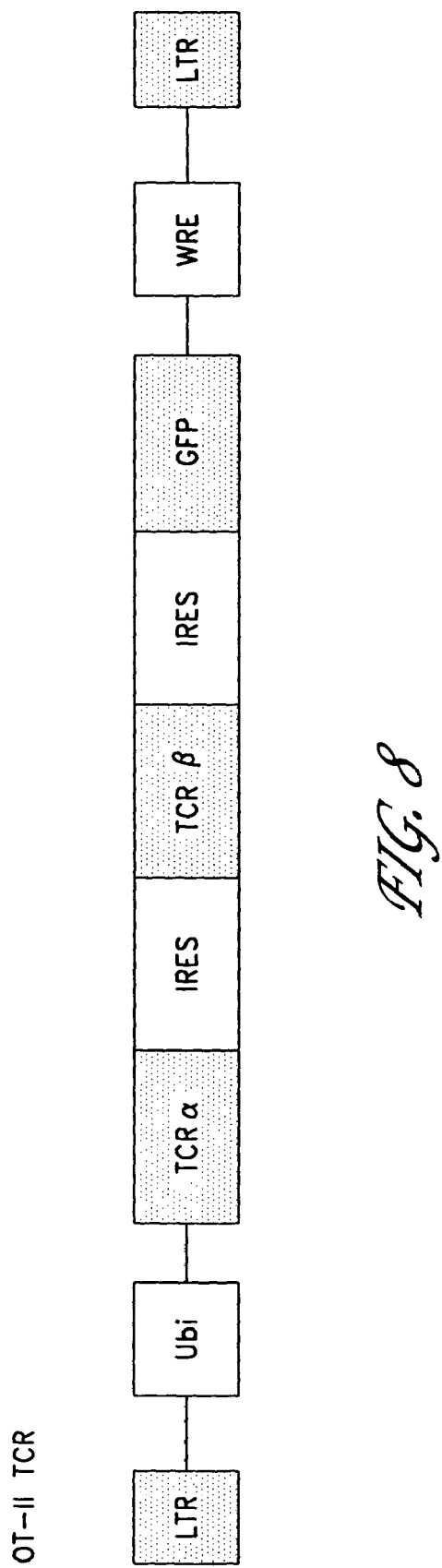

FIG. 8 is a diagram of a lentiviral construct that is used to produce recombinant lentivirus. The tri-cistronic construct comprises sequence encoding the OTII TCR α and β chains, as well as a GFP marker gene. The genes are separated by an internal ribosome entry site (IRES) sequence. Recombinant virus is produced in a packaging cell line and used to infect cells in which T cell receptor expression is desired.

Figure 9A:
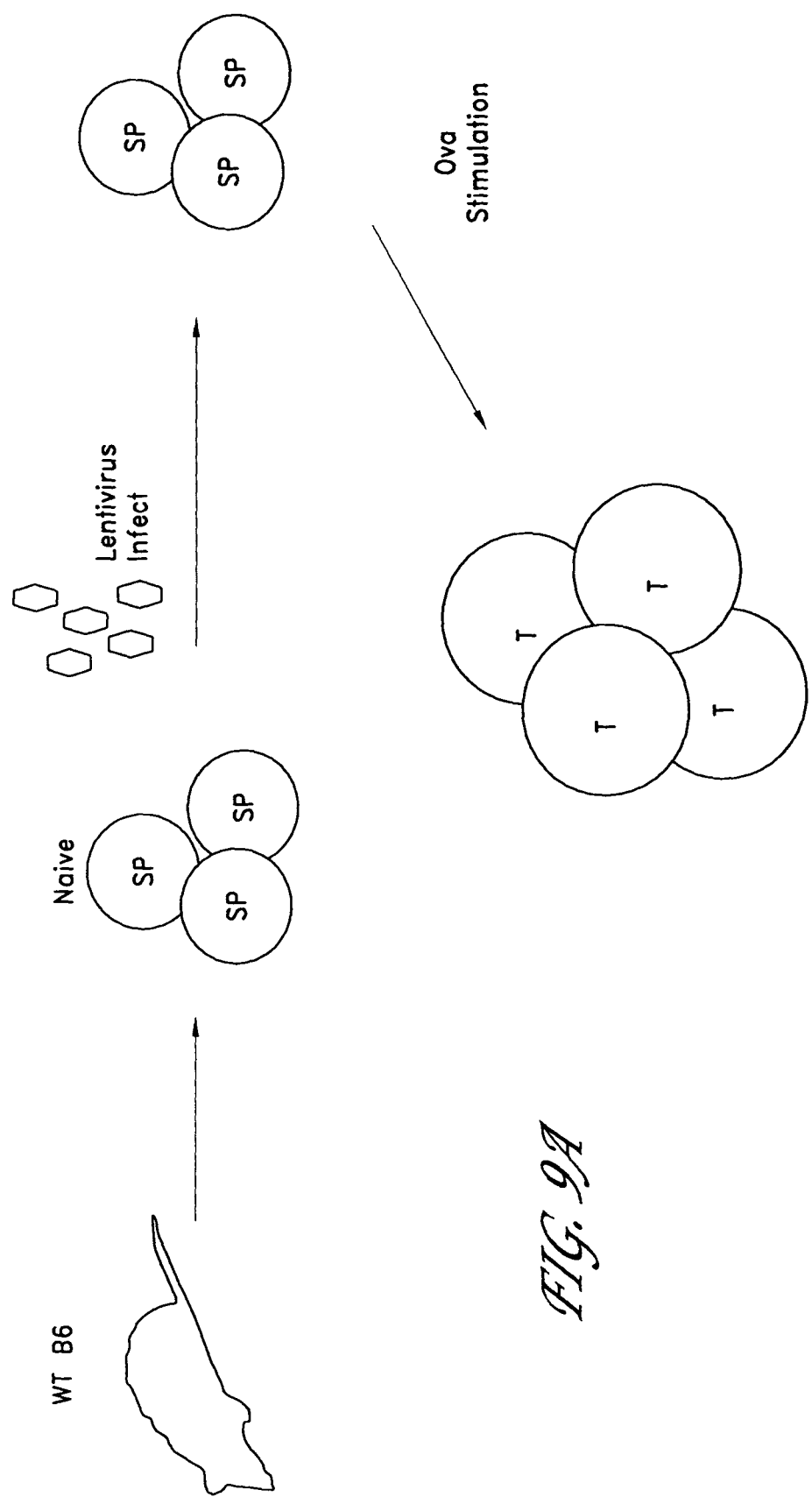
Figure 9B:
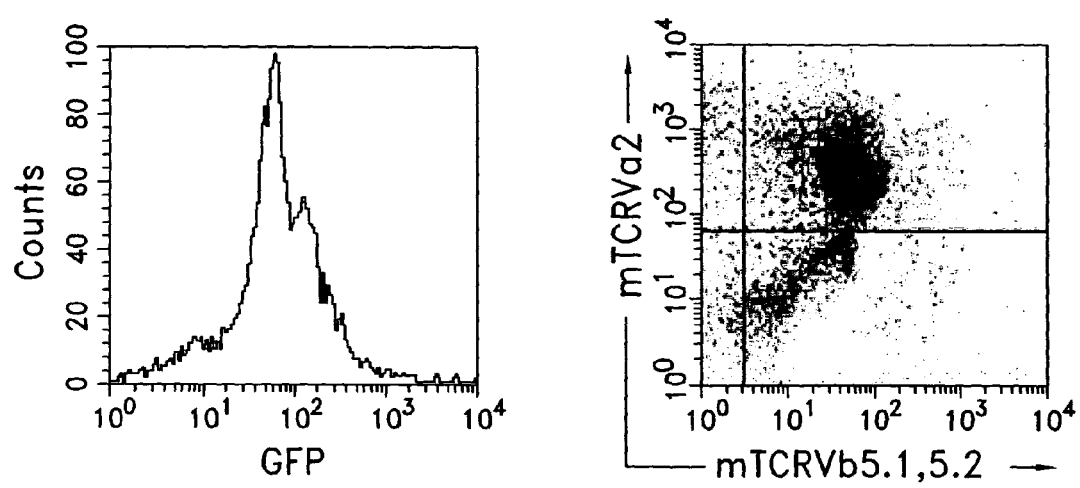

FIG. 9A diagrams the method of infection of naive T cells with the tri-cistronic lentivirus comprising OTII TCR α, β and GFP. Naive spleen cells are obtained from wild type B6 mice and infected with recombinant lentivirus. The cells are then stimulated with ova and their response is measured. As shown in FIG. 9B, nearly all cells are GFP positive and greater than 90% express OTII TCR α and β and respond to antigen stimulation.

Figure 10:
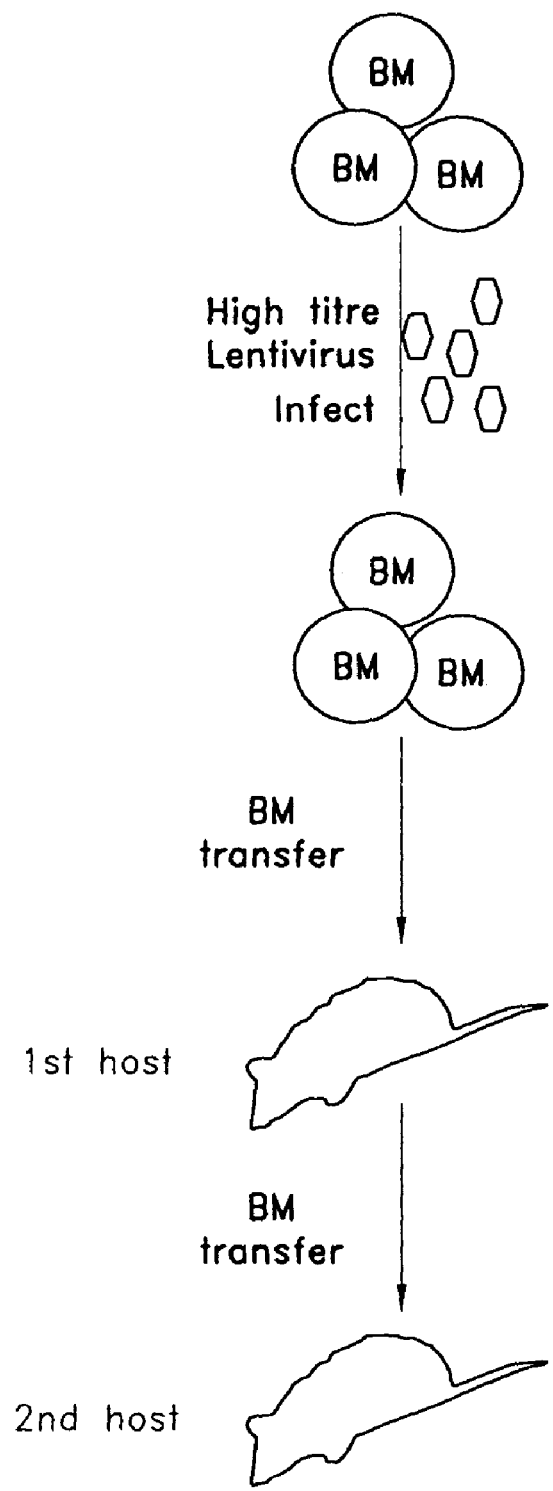

FIG. 10 diagrams the method of producing modified T cells in wild type animals. Wild type bone marrow cells are infected with lentivirus comprising the OTII TCR α and β chain and the GFP marker. The bone marrow is transferred into a wild type, non-irradiated mouse, the first host. Bone marrow from the first mouse is transferred into a second wild type mouse, the second host. Cells from the first and second host are analyzed for expression of the GFP marker gene.

Figure 11A:
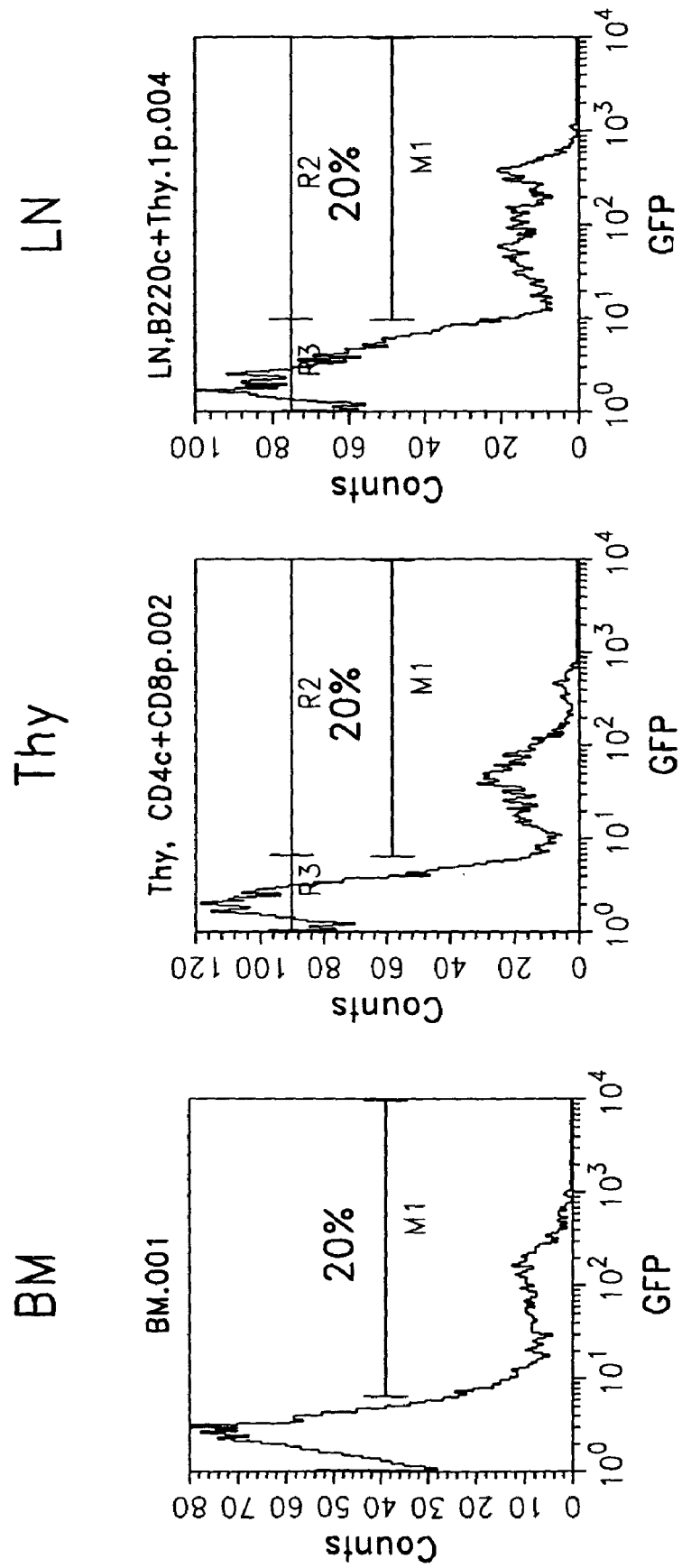
Figure 11B:
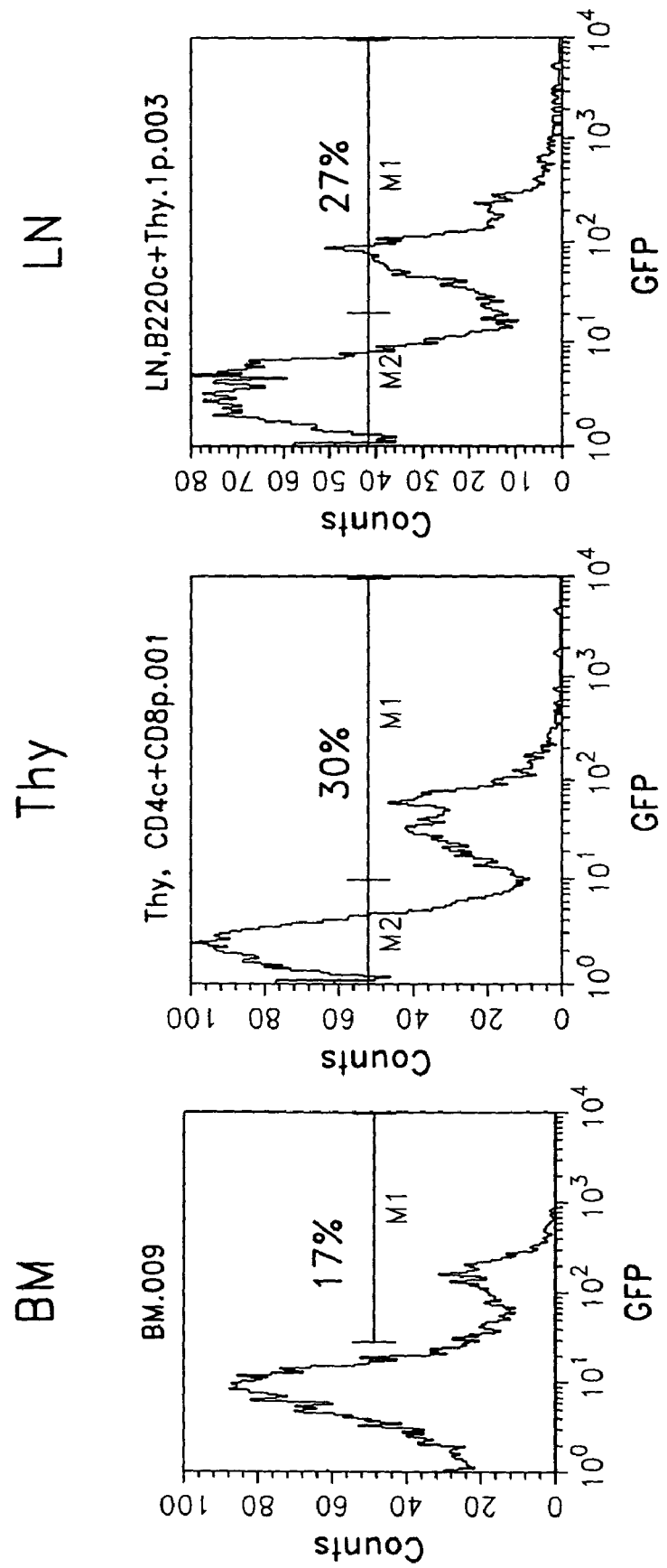

FIGS. 11A and 11B show that cells from the bone marrow (BM), thymus (Thy) and peripheral lymph nodes (LN) of both the first and second host treated as in FIG. 10, express the GFP transgene, indicating that the gene is stably integrated in the hematopoietic stem cells.

FIGS. 12A and 12B show that lentiviral infection of fresh bone marrow (BM) mediated stable gene transfer into hematopoietic stem cells. Approximately 30% of B cells from the first host and 10% of T cells express GFP, while approximately 31% of B cells and 26% of T cells from the second host express GFP.

Figure 13A:
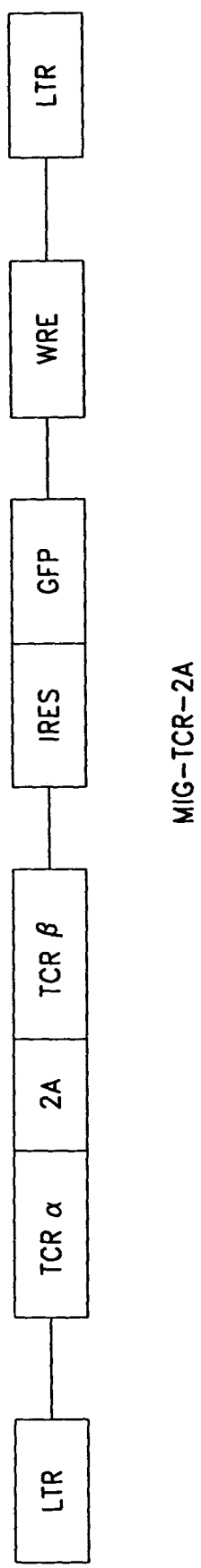

FIG. 13A is a schematic diagram of a MIG-TCR-2A retrovirus construct.

FIG. 13B illustrates non-limiting examples of various 2A sequences. Shown are examples of exemplary 2A sequences from the foot-and-mouth disease virus (F2A) (SEQ ID NO: 6), equine rhinitis A virus (E2A) (SEQ ID NO: 7), *Thosea asigna* virus (T2A) (SEQ ID NO: 8), and porcine teschovirus-1 (P2A) (SEQ ID NO: 9). As illustrated, the 2A peptide is separated ("cleaved") at its own C-terminus co-translationally between the glycine and proline amino acids.

Figure 13C:
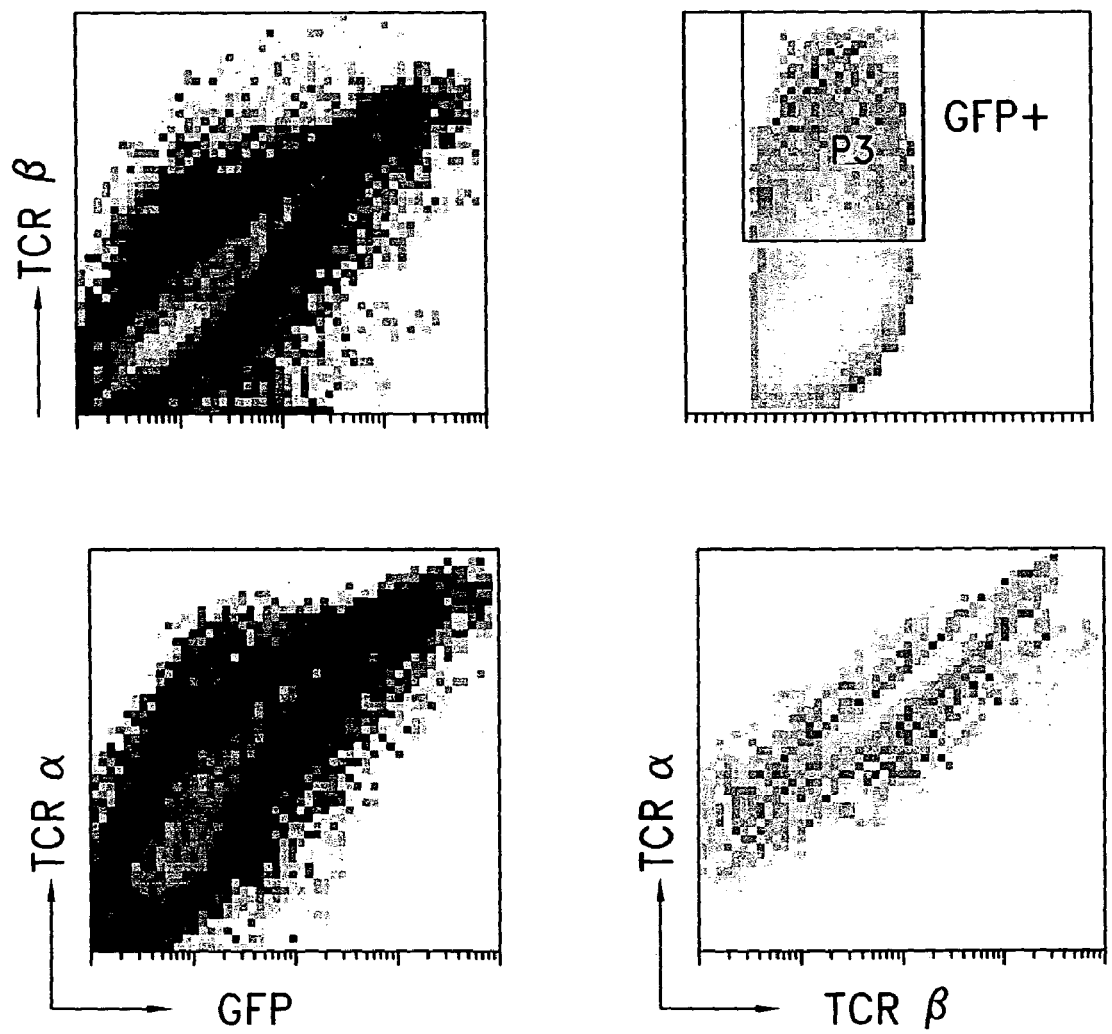

FIG. 13C illustrates the MIG-TCR-2A vector-mediated co-expression of three genes: TCRα, TCRβ, and GFP, using 2A (11aa). The panels of FIG. 13C shows that infected THZ cells (identified by expression of the GFP marker gene) expressed OTII TCRα and TCRβ, on the surface, as well as GFP.

Figure 14A:
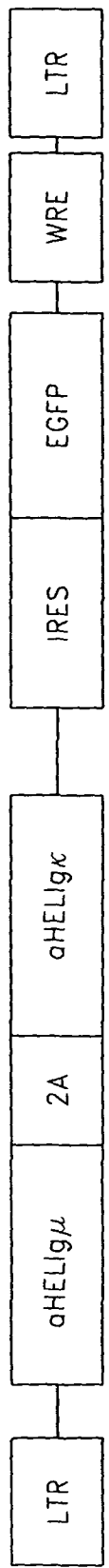

FIG. 14A is a schematic representation of the tricistronic MIG-aHEL-2A viral vector comprising the cDNAs for the anti-HEL (hen egg lysozyme) antibody heavy and light chains, as well as an IRES element adjacent to EGFP, and a woodchuck responsive element (WRE), all in between two long terminal repeats (LTRs).

Figure 14B:
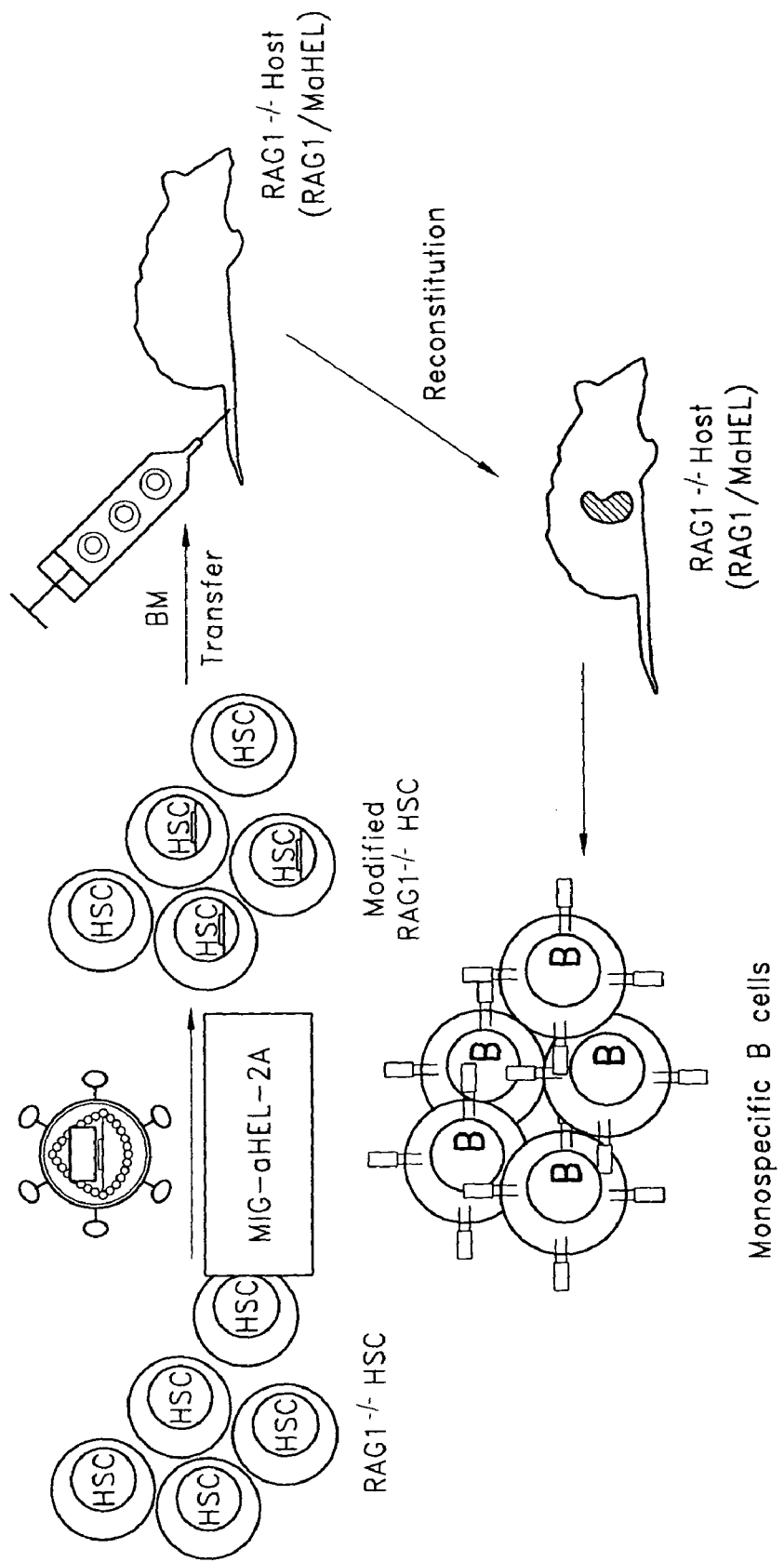

FIG. 14B is a schematic diagram of an in vivo experiment for generating antigen-specific B lymphocytes by genetic programming of hematopoietic stem cells (HSCs). HSCs are obtained from RAG1−/− mice and transduced with MIG-aHEL retroviruses. The transduced cells are then transferred into RAG1−/− hosts and are allowed to reconstitute the immune system. Monospecific B cells were generated using this method.

Figure 14C:
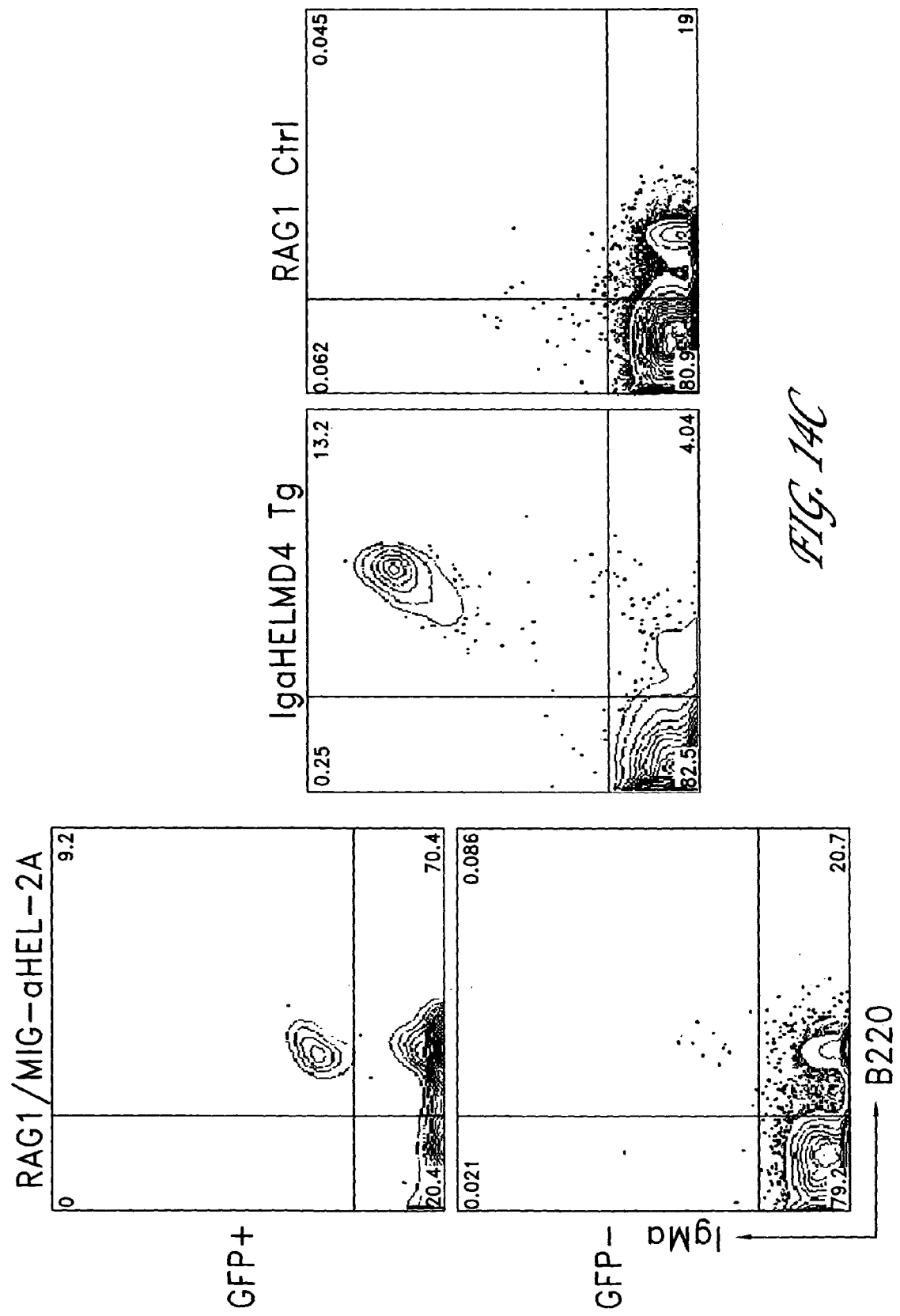

FIG. 14C illustrates development of transgenic B cells in the bone marrow of RAG1−/− mice receiving RAG1−/− HSCs transduced with MIG-aHEL-2A viruses. Eight weeks after bone marrow transplantation, bone marrow cells were collected and analyzed for B cell development. The distribution of B220 and IgMa on GFP+ and GFP− cells are shown. Bone marrow cells of anti-HEL transgenic mice and RAG1−/− mice are shown as controls.

Figure 14D:
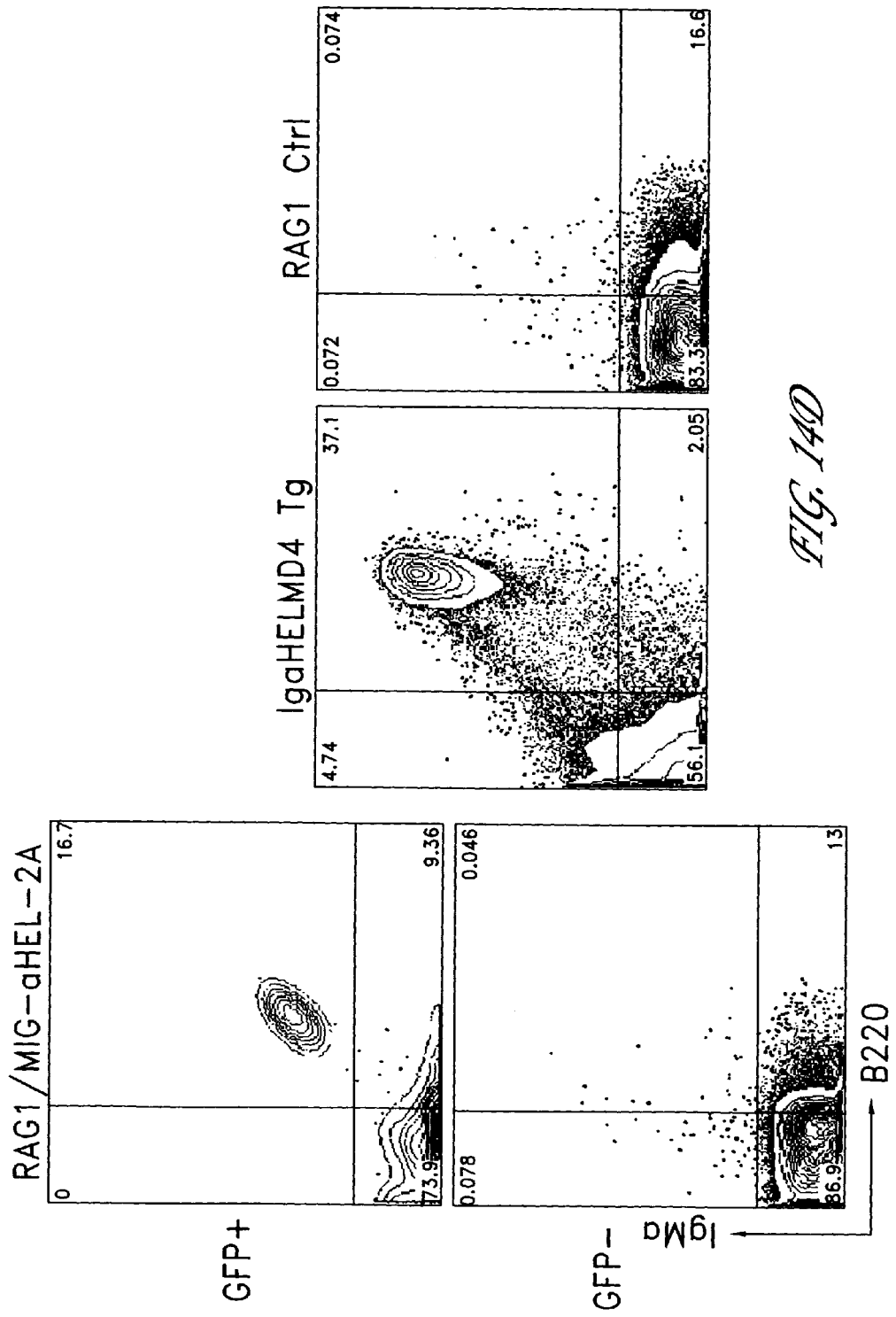

FIG. 14D shows results detecting transgenic B cells in the periphery of RAG1−/− mice receiving RAG1−/− HSCs transduced with MIG-aHEL-2A viruses. Eight weeks after bone marrow transplantation, spleen and lymph node cells were collected and analyzed for the presence of mature B cells. The distribution of B220 and IgMa on GFP+ and GFP− cells are shown. Spleen and lymph node cells of anti-HEL transgenic mice and RAG1−/− mice are shown as controls.

DETAILED DESCRIPTION OF THE PREFERRED EMBODIMENT

Embodiments of the invention are related to the experimental finding that it is possible to obtain functional immune cells with a desired antigen specificity by expression of the appropriate cDNAs in hematopoietic stem cells. For example, functional T cells with a desired antigen specificity can be obtained by expression of TCR α and β cDNAs in hematopoietic stem cells.

Methods are provided for generating immune cells with desired antigen specificity. According to one aspect of the invention, immune cells with antigen specificity are generated by transfecting an appropriate target cell with an antigen-specific polynucleotide. The target cell is then transferred into a host organism where it develops into functional immune cells. One or more genes that enhance immune cell function may be specifically expressed in the immune cell generated by these methods.

In a preferred embodiment, functional antigen-specific T cells are generated by transfecting target cells with an antigen-specific polynucleotide encoding a functional T cell receptor. More preferably, TCR α and β cDNAs are expressed in hematopoietic stem cells by transfecting the cells with one or more retrovirus based vectors.

In another preferred embodiment, functional antigen-specific B cells are generated by transfecting target cells with an antigen-specific polynucleotide encoding an antibody. More preferably, heavy and light chains are expressed in hematopoietic stem cells by transfecting the cells with one or more retrovirus based vectors.

After generation of the antigen-specific immune cell, the cells may then be transferred into a host mammal where they mature into normal, functional immune cells that can be expanded and activated by exposure to antigen. The methods may be used therapeutically to generate a desired immune response in a patient in need of treatment. Preferably the patient is suffering from a disease or disorder in which a specific antigen can be identified, such as cancer or HIV infection.

In another aspect of the current invention the polynucleotide delivery system is used to control the differentiation or cell fate of target cells, such as hematopoietic stem cells. This allows for the expression of one or more desired genes in a specific sub-population of cells. For example, genes that enhance immune cell function may be expressed exclusively in a sub-population of immune cells that are specific for a desired antigen.

In preferred embodiments, the target cells are transfected by contacting them with a polynucleotide delivery system that comprises an antigen specific polynucleotide. The antigen-specific polynucleotide encodes an antigen-specific polypeptide with a desired specificity, such as a T cell receptor or a B cell receptor. Expression of the antigen-specific polypeptide causes the cell to differentiate into a desired cell type, such as a T cell or B cell.

In one embodiment, the antigen specific polynucleotide encodes a T cell receptor that is specific for a desired antigen. Target cells, preferably hematopoietic stem cells such as bone marrow stem cells, are transfected with the antigen specific polynucleotide and transferred to a host mammal where they mature into T cells. In another embodiment, the polynucleotide delivery system encodes a B cell receptor, the expression of which results in the target cell maturing into a B cell.

In other embodiments non-native antigen specific polypeptides are encoded by the antigen specific polynucleotide. For example, fractions or subparts of T cell or B cell receptors or mutated receptors may be encoded by the antigen specific polynucleotide. Thus, a population of B or T cells may be created as desired, but need not express a native antigen specific polypeptide.

In some embodiments the polynucleotide delivery system also comprises one or more additional genes, preferably genes that enhance immune cell function. Because they are contained within the same polynucleotide delivery system, expression of the additional genes is limited to the population of cells with the desired antigen specificity. This may be useful therapeutically, for example to enhance the efficacy of a T cell population that is specific for a disease antigen, prevent the development of tolerance in a specific T cell population, or enhance the efficacy of a B cell population that is specific for an antibody to a particular disease antigen. Importantly, the ability to enhance function in a specific therapeutic immune cell population limits the problems associated with enhancing the immune function of all T or B cells, such as problems with autoimmunity.

Further, as will be recognized by one of skill in the art, populations of immune cells with the desired antigen specificity generated by the disclosed methods may be expanded in vivo or in vitro by contacting the cells with antigen to which the receptors bind. For example, a population of T cells can be produced in a patient that are targeted to a specific antigen associated with a disease from which the patient is suffering. The specific population of T cells can be expanded in vivo by injection of purified antigen. Alternatively, the desired T cells can be isolated, expanded in vitro and returned to that patient or to another patient suffering from the same disease or disorder. As discussed above, a gene that enhances T cell activity may also be specifically expressed in the therapeutic T cell population. Populations of B cells can similarly be expanded.

A. DEFINITIONS

Unless defined otherwise, technical and scientific terms used herein have the same meaning as commonly understood by one of ordinary skill in the art to which this invention belongs. See, e.g. Singleton et al., *Dictionary of Microbiology and Molecular Biology* 2nd ed., J. Wiley & Sons (New York, N.Y. 1994); Sambrook et al., *Molecular Cloning, A Laboratory Manual*, Cold Springs Harbor Press (Cold Springs Harbor, N.Y. 1989). Any methods, devices and materials similar or equivalent to those described herein can be used in the practice of this invention.

As used herein, the terms nucleic acid, polynucleotide and nucleotide are interchangeable and refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages.

The terms nucleic acid, polynucleotide and nucleotide also specifically include nucleic acids composed of bases other than the five biologically occurring bases (adenine, guanine, thymine, cytosine and uracil).

As used herein, a nucleic acid molecule is said to be "isolated" when the nucleic acid molecule is substantially separated from contaminant nucleic acid molecules encoding other polypeptides.

An "antigen" is any molecule that is capable of binding to an antigen specific polypeptide. Preferred antigens are capable of initiating an immune response upon binding to an antigen specific polypeptide that is expressed in an immune cell. An "immune response" is any biological activity that is attributable to the binding of an antigen to an antigen specific polypeptide.

The term "epitope" is used to refer to a site on an antigen that is recognized by an antigen specific polypeptide.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules that lack antigen specificity. Polypeptides of the latter kind are, for example, produced at low levels by the lymph system and at increased levels by myelomas.

"Native antibodies" and "native immunoglobulins" are usually heterotetrameric glycoproteins, composed of two identical light (L) chains and two identical heavy (H) chains. Each light chain is linked to a heavy chain by a disulfide bond. The number of disulfide linkages varies among the heavy chains of different immunoglobulin isotypes. Each heavy chain comprises a variable domain ($V_H$) followed by a number of constant domains. Each light chain comprises a variable domain at one end ($V_L$) and a constant domain at its other end. The constant domain of the light chain is aligned with the first constant domain of the heavy chain, and the light-chain variable domain is aligned with the variable domain of the heavy chain.

The term "antibody" herein is used in the broadest sense and specifically covers human, non-human (e.g. murine) and humanized monoclonal antibodies (including full length monoclonal antibodies), polyclonal antibodies, multi-specific antibodies (e.g., bispecific antibodies), and antibody fragments so long as they exhibit the desired biological activity.

T cell receptors ("TCRs") are complexes of several polypeptides that are able to bind antigen when expressed on the surface of a cell, such as a T lymphocyte. The $\alpha$ and $\beta$ chains, or subunits, form a dimer that is independently capable of antigen binding. The $\alpha$ and $\beta$ subunits typically comprise a constant domain and a variable domain.

As used herein, the term "T cell receptor" includes a complex of polypeptides comprising a T cell receptor $\alpha$ subunit and a T cell receptor $\beta$ subunit. The $\alpha$ and $\beta$ subunits may be native, full-length polypeptides, or may be modified in some way, provided that the T cell receptor retains the ability to bind antigen. For example, the $\alpha$ and $\beta$ subunits may be amino acid sequence variants, including substitution, addition and deletion mutants. They may also be chimeric subunits that comprise, for example, the variable regions from one organism and the constant regions from a different organism.

"Target cells" are any cells that are capable of expressing an antigen-specific polypeptide on their surface. Preferably, target cells are capable of maturing into immune cells, such as lymphocytes. Target cells include stem cells, particularly hematopoietic stem cells.

As used herein, a cell exhibits a "unique antigen specificity" if it is primarily responsive to a single type of antigen.

The term "mammal" is defined as an individual belonging to the class Mammalia and includes, without limitation, humans, domestic and farm animals, and zoo, sports, or pet animals, such as sheep, dogs, horses, cats or cows. Preferably, the mammal herein is human.

A "subject" is any mammal that is in need of treatment.

As used herein, "treatment" is a clinical intervention made in response to a disease, disorder or physiological condition manifested by a patient or to be prevented in a patient. The aim of treatment includes the alleviation and/or prevention of symptoms, as well as slowing, stopping or reversing the progression of a disease, disorder, or condition. "Treatment" refers to both therapeutic treatment and prophylactic or preventative measures. Those in need of treatment include those already affected by a disease or disorder or undesired physiological condition as well as those in which the disease or disorder or undesired physiological condition is to be prevented.

"Tumor," as used herein, refers to all neoplastic cell growth and proliferation, whether malignant or benign, and all precancerous and cancerous cells and tissues.

The term "cancer" refers to a disease or disorder that is characterized by unregulated cell growth. Examples of cancer include, but are not limited to, carcinoma, lymphoma, blastoma and sarcoma. Examples of specific cancers include, but are not limited to, lung cancer, colon cancer, breast cancer, testicular cancer, stomach cancer, pancreatic cancer, ovarian cancer, liver cancer, bladder cancer, colorectal cancer, and prostate cancer. Additional cancers are well known to those of skill in the art.

A "vector" is a nucleic acid molecule that is capable of transporting another nucleic acid. Vectors may be, for example, plasmids, cosmids or phage. An "expression vector" is a vector that is capable of directing the expression of a protein encoded by one or more genes carried by the vector when it is present in the appropriate environment. Vectors are preferably capable of autonomous replication.

The term "regulatory element" and "expression control element" are used interchangeably and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells may include, without limitation, promoters, enhancers, splicing signals and polyadenylation signals.

The term "transfection" refers to the introduction of a nucleic acid into a host cell by nucleic acid-mediated gene transfer, such as by contacting the cell with a polynucleotide delivery system as described below. "Transformation" refers to a process in which a cell's genetic make up is changed by the incorporation of exogenous nucleic acid.

By "transgene" is meant any nucleotide or DNA sequence that is integrated into one or more chromosomes of a target cell by human intervention. In one embodiment the transgene comprises an antigen-specific polynucleotide that encodes an antigen-specific polypeptide whose expression in a target cell is desired. The antigen-specific polynucleotide is generally operatively linked to other sequences that are useful for obtaining the desired expression of the gene of interest, such as transcriptional regulatory sequences. In another embodiment the transgene can additionally comprise a DNA sequence that is used to mark the chromosome where it has integrated.

The term "transgenic" is used herein to describe the property of harboring a transgene. For instance, a "transgenic organism" is any animal, including mammals, fish, birds and amphibians, in which one or more of the cells of the animal contain nucleic acid introduced by way of human intervention. In the typical transgenic animal, the transgene causes the cell to express or overexpress a recombinant protein.

"Retroviruses" are enveloped RNA viruses that are capable of infecting animal cells. "Lentivirus" refers to a genus of retroviruses that are capable of infecting dividing and non-dividing cells. Several examples of lentiviruses include HIV (human immunodeficiency virus; including HIV type 1, and HIV type 2), visna-maedi, the caprine arthritis-encephalitis virus, equine infectious anemia virus, feline immunodeficiency virus (FIV), bovine immune deficiency virus (BIV), and simian immunodeficiency virus (SIV).

"Transformation," as defined herein, describes a process by which exogenous DNA enters a target cell. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. "Transformed" cells include stably transformed cells in which the inserted DNA is capable of replication either as an autonomously replicating plasmid or as part of the host chromosome. Also included are cells that transiently express the antigen specific polypeptide.

One or more genes that "enhance immune cell function" are utilized in some embodiments. A gene that "enhances immune cell function" is one that causes the immune cell to have a desired activity or property, and/or that enhances or otherwise facilitates a desired property of the immune cell. Examples include, but are not limited to, enhancing immune cell response to antigen, enhancement of immune cell survival, augmenting immune cell expansion, generation of memory lymphocytes, offsetting immune suppression, providing safety controls, allowing for imaging of immune cells, delivery of active molecules to a target, such as immunomodulatory agents to the site of inflammation or compounds that target infectious disease.

"2A sequences" or elements are small peptides introduced as a linker between two proteins, allowing autonomous intrariboromal self-processing of polyproteins (See, for example, de Felipe. Genetic Vaccines and Ther. 2:13 (2004) and deFelipe et al. Traffic 5:616-626 (2004)). These short peptides allow co-expression of multiple proteins from a single vector. Several 2A elements that can be used are illustrated in FIG. 13B. Other 2A elements that are known in the art can also be used.

Antigens

The methods and compositions of the invention can be used to develop an immune response within an organism that is directed against a particular antigen of interest, such as an antigen that is associated with a disease or disorder. Thus, an antigen is preferably identified that is associated with a disease or disorder of interest, such as a disease or disorder that is to be treated in a patient. Once an antigen has been identified, an antigen-specific polynucleotide is identified such that expression of the antigen-specific binding protein encoded by the antigen-specific polynucleotide will cause a cell to be targeted to the desired antigen.

The antigen is not limited in any way and is preferably chosen based on the desired immune response. Antigens may be, for example, polypeptides, carbohydrates, lipids or nucleic acids. Examples of antigens to which an immune response can be developed include, without limitation, tumor antigens, viral antigens, microbial antigens, allergens, and autoantigens. In one embodiment, the antigen is a viral antigen, such as an HIV antigen. In another embodiment the antigen is a tumor associated antigen (TAA).

In a preferred embodiment an immune response is to be generated against a tumor associated antigen, such as in a mammal that has a tumor or other cancer or disease that is associated with a tumor associated antigen. Tumor associated antigens are known for a variety of diseases including, for example, melanoma, prostate cancer and breast cancer. In some breast cancers, for example, the Her-2 receptor is over-expressed on the surface of cancerous cells. A number of tumor associated antigens have been reviewed (see, for example, "Tumor-Antigens Recognized By T-Lymphocytes," Boon T, Cerottini J C, Vandeneynde B, Vanderbruggen P, Vanpel A, Annual Review Of Immunology 12: 337-365, 1994; "A listing of human tumor antigens recognized by T cells," Renkvist N, Castelli C, Robbins P F, Parmiani G. Cancer Immunology Immunotherapy 50: (1) 3-15 Mar. 2001).

Antigen-Specific Polypeptides and Polynucleotides

Once an antigen of interest has been selected, an antigen-specific polypeptide that is capable of interacting with the antigen is preferably identified, along with the antigen-specific polynucleotide that encodes it. An "antigen-specific polypeptide" or "antigen-specific binding protein" is a polypeptide that is capable of selectively binding to a particular antigen. That is, it binds to one antigen but does not substantially bind to other antigens. The term "antigen-specific polypeptide" encompasses both single polypeptides and a number of independent polypeptides that interact, as in a multi-subunit receptor. A preferred "antigen specific polypeptide" is a T cell receptor, particularly a T cell receptor that comprises an α subunit and a β subunit. Another preferred "antigen specific polypeptide" is an antibody, particularly an antibody that comprises heavy and light chains. When expressed on the surface of a cell the antigen-specific polypeptide is capable of causing the cell to selectively interact with a desired antigen. If the cell is of the appropriate type, such as an immune cell, particularly a lymphocyte, the selective interaction may generate an immune response.

An "antigen-specific polynucleotide" is a polynucleotide that encodes an antigen-specific polypeptide. The antigen specific polynucleotide may encode more than one polypeptide. For example, the antigen specific polynucleotide may encode all of the subunits of a multi-subunit receptor.

An antigen-specific polynucleotide may comprise a single polynucleotide molecule. However, an "antigen-specific polynucleotide" may comprise more than one independent polynucleotide molecule, particularly when it encodes an antigen-specific polypeptide that comprises more that one subunit. In this case, each subunit may be encoded by a separate polynucleotide. All of the subunits may alternatively be encoded by a single polynucleotide.

An antigen-specific polynucleotide can be derived from any source, but is preferably derived from a genomic DNA sequence or a cDNA sequence of a gene. In addition, the antigen-specific polynucleotide can be produced synthetically or isolated from a natural source. Antigen-specific polynucleotides may comprise, without limitation, DNA, cDNA and/or RNA sequences that encode antigen-specific polypeptides. Preferably, the antigen-specific polynucleotides used in the methods of the present invention comprise cDNA sequences.

It is understood that all polynucleotides encoding a desired antigen-specific polypeptide are included herein. Such polynucleotides include, for example, naturally occurring, synthetic, and intentionally manipulated polynucleotides. For example, the antigen-specific polynucleotide may be a naturally occurring polynucleotide that has been subjected to site-directed mutagenesis. Also included are naturally occurring antigen-specific polynucleotides that comprise deletions, insertions or substitutions, so long as they encode antigen-specific polypeptides that retain the ability to interact with the antigen.

The antigen-specific polynucleotides of the invention also include sequences that are degenerate as a result of the genetic code. There are 20 natural amino acids, most of which are specified by more than one codon. Therefore, all degenerate nucleotide sequences are included in the invention as long as the encoded polypeptide has the desired specificity.

In one embodiment, the polynucleotide sequence is a cDNA sequence. In another embodiment, the polynucleotide sequence is a cDNA sequence that has been intentionally manipulated, such as a cDNA that has been mutated to remove potential splice sites or to match codon usage to a particular host organism. Such manipulations are within the ordinary skill in the art.

In one embodiment of the invention, the antigen-specific polynucleotide encodes an antigen specific polypeptide that is a cell surface receptor. In a preferred embodiment, the antigen specific polynucleotide encodes one or more antigen-specific polypeptides selected from the group consisting of T cell receptors and immunoglobulins, including, without limitation, B cell receptors (BCR), single chain antibodies, and combinations thereof.

The polynucleotide sequence of an antigen specific polypeptide, such as a receptor that is specific for a given antigen, can be determined or generated by any technique known in the art. In a preferred embodiment the antigen specific polypeptide is a T cell receptor (TCR). One technique available for obtaining the polynucleotide sequence of a T cell receptor is to isolate immune cells that bind to a specific antigen and to determine the sequence of the T cell receptor (TCR) encoded by that isolated clone. This method is well known in the art.

When a TCR sequence is determined in an organism other than that from which the target cells in which it is to be expressed are derived, it is possible to clone out the whole TCR. However, a preferred method is to clone out the sequence of the variable regions of the TCR subunits. Then the variable sequences are linked to the sequence of the TCR gene constant regions from the organism from which the target cells are derived to obtain an antigen-specific polynucleotide. The hybrid TCR expressed from this antigen-specific polynucleotide has the desired antigen specificity, but originates from the same organism as the target cells.

In one embodiment a TCR that recognizes an antigen of interest is identified. An antigen of interest, such as a protein or peptide, is identified, for example a tumor specific antigen (for one type of tumor or several types of tumor). The antigen is used to immunize a humanized mouse that express certain human HLA allele(s). T cell clones are generated that respond to the tumor antigen, which are restricted by the expressed human HLA allele(s). TCRs are then cloned from these T cell clones. A single antigen-specific polynucleotide encoding a TCR that recognizes the antigen of interest may be identified and transferred into target cells using a polynucleotide delivery system as described below. The target cells may then be transferred into a mammal in which an immune response to the antigen is desired.

Alternatively, a TCR library of polynucleotides encoding TCRs with desired properties (e.g. high antigen responsiveness and/or the ability to collaborate with each other) may be established from the T cell clones. The TCRs may be whole cloned TCRs or hybrid TCRs as described above. The TCR library may then be delivered into target cells, one TCR per fraction, to generate antigen-specific T cells. This can be accomplished, for example, using the techniques described for a single gene (not a library) by Stanislawski, 2001, "Circumventing tolerance to a human MDM2-derived tumor antigen by TCR gene transfer." *Nature Immunol.* 2, 962-70.

When the antigen-specific polypeptide is not a TCR, other techniques can be used to identify an antigen-specific polynucleotide sequence. For example, when the antigen-specific polypeptide is an immunoglobulin, the antigen-specific polynucleotide sequence can be derived from the sequence of a monoclonal antibody that specifically binds the antigen. The antigen-specific antibody can comprise the entire antibody. However, if the antigen-specific polypeptide is to be used to generate an immune response in a mammal, the antibody sequence will preferably be fused to a membrane-spanning domain and appropriate signaling peptides. Alternatively, an antigen-specific polypeptide comprising an antibody fragment can be used, such as by grafting the antibody fragment to a membrane spanning region and appropriate signaling sequences.

In another embodiment, the antigen-specific polypeptide comprises the variable region responsible for the interaction of an antibody with an antigen. For example, the variable region may be grafted into the sequence of a B cell receptor sequence.

In these and similar ways, a monoclonal antibody from an organism other than that from which the target cells are derived can be used to generate an antigen-specific polypeptide that is specific to the target cell organism. Other techniques known in the art for generating diversity in a receptor can also be used.

Antigen-specific polynucleotides can also be generated by a variety of molecular evolution and screening techniques, including, for example, exon shuffling and phage display. For example, when the antigen-specific polypeptide is an immunoglobulin, including both single chain and dual chain antibodies, a polynucleotide encoding the immunoglobulin specific for a given antigen can be selected using phage display techniques. Phage display can be performed in a variety of formats; for their review see, e.g., Johnson, Kevin S. and Chiswell, David J., *Current Opinion in Structural Biology* 3:564-571 (1993).

Polynucleotide Delivery System

A polynucleotide delivery system is any system capable of introducing a polynucleotide, particularly an antigen-specific polynucleotide into a target cell. Polynucleotide delivery systems include both viral and non-viral delivery systems. One of skill in the art will be able to determine the type of polynucleotide delivery system that can be used to effectively deliver a particular antigen-specific polynucleotide into a target cell.

When the antigen-specific polypeptide is a single polypeptide chain, the antigen-specific polynucleotide encoding it is preferably introduced into the target cell in a single polynucleotide delivery system. However, when the antigen-specific polypeptide is a multimeric receptor, for example a dimeric receptor, antigen-specific polynucleotides encoding each of the subunits can be introduced into the target cell, either as a single polynucleotide in a single polynucleotide delivery system, or as separate polynucleotides in one or more polynucleotide delivery systems. Preferably, a single polynucleotide delivery system is utilized, comprising polynucleotides encoding each subunit of the receptor.

For example, when an antigen-specific polynucleotide encoding a TCR α subunit is to be delivered, it is advantageous to also introduce an antigen-specific polynucleotide encoding a TCR β subunit. If the polynucleotide delivery system has sufficient capacity, the α and β subunits can be introduced together, for example as a single antigen-specific polynucleotide. Thus, in one embodiment the polynucleotide delivery system comprises a polynucleotide encoding a TCR α subunit and a polynucleotide encoding a TCR β subunit. Preferably, one of the subunits is preceded by an IRES or 2A element, as discussed below, in order to facilitate equivalent expression of each subunit. Alternatively, polynucleotides encoding the α and β subunits can be introduced separately into the target cell, each in an appropriate polynucleotide delivery system, for example each as a separate retroviral particle.

In other embodiments the polynucleotide delivery system comprises one or more polynucleotides in addition to the antigen specific polynucleotides. Preferably one or more additional genes are included in the same vector as the antigen specific polynucleotide. In this case, all genes are preferably under the control of the same promoter. As discussed in more detail below, the additional gene or genes may be operably linked to an internal ribosomal entry sequence (IRES) elements as described, for example, in U.S. Pat. No. 4,937,190, or another element, such as a 2A sequence, that facilitates co-expression. Preferably, an IRES element or 2A sequence precedes each additional gene in the vector. The additional genes or genes are then co-expressed with the antigen-specific polynucleotide.

In some embodiments, the additional gene or genes may be operably linked to one or more 2A sequences. 2A sequences are small peptides introduced as a linker between two proteins, allowing autonomous intraribosomal self-processing of polyproteins (see, for example, de Felipe. Genetic Vaccines and Ther. 2:13 (2004) and deFelipe et al. Traffic 5:616-626 (2004)). These short peptides allow co-expression of multiple proteins from a single vector. FIG. 13B illustrates non-limiting examples of various 2A sequences. Shown are exemplary 2A sequences from the foot-and-mouth disease virus (F2A) (SEQ ID NO: 6), equine rhinitis A virus (E2A) (SEQ ID NO: 7), *Thosea asigna* virus (T2A) (SEQ ID NO: 8), and porcine teschovirus-1 (P2A) (SEQ ID NO: 9). As illustrated, the 2A peptide is separated ("cleaved") at its own C-terminus co-translationally between the glycine and proline amino acids. Separation is mediated by a novel translational effect (a putative ribosomal "skip"), in contrast to other separation mechanisms (e.g., proteinases) that require a proteolytic reaction. Post-translation, the 2A sequence remains as a C-terminal extension of the upstream product (not shown).

Sequences adjacent to the N-terminus of the 2A peptide may affect separation of the 2A sequence at the C-terminus. For example, sequences adjacent to the N-terminus that favor the formation of a helical conformation of the 2A peptide may improve 2A activity, and thus promote separation. Some non-limiting examples of various sequences that may be included adjacent to the N-terminus of the 2A peptide to promote separation. These sequences are noted in SEQ ID NOS: 10-13. SEQ ID NO: 10 is a sequence of the C-terminus of the native TCRα chain followed by a two amino acid linker sequence GP. SEQ ID NO: 11 is a sequence of the C-terminus of a modified TCRα chain in which one serine residue has been deleted, followed by the two amino acid linker sequence GP. In some embodiments, the modified TCRα chain can advantageously improve 2A activity and increase expression of the T cell receptor without affecting the function of the T cell receptor.

SEQ ID NO: 12 illustrates the sequence of the C-terminus of the modified TCRα chain as described above followed by a 5 amino acid linker sequence GSGAP. SEQ ID NO: 13 illustrates the sequence of the C-terminus of the modified TCRα chain as described above followed by a 14 amino acid linker sequence GSGEARHKQKIVAP.

One or more of the additional genes may encode a marker that can be used to identify cells that have been successfully transfected. For example, the polynucleotide delivery system may comprise a polynucleotide that encodes a marker, such as green fluorescent protein (GFP) or an enzyme like beta lactamase, luciferase or herpes simplex virus type 1 thymidine kinase (hsvTK). Substrates for the enzymes can be subsequently provided and cells expressing the antigen specific polypeptide can be identified. For example, the radiotracers 131iodine-FIAU and 124Iiodine-FIAU, which are substrates for hsvTK, can be used to non-invasively identify cells co-expressing hsvTK and the antigen specific polypeptide. (Ponomarev et al. *Neoplasia* 3:480-488 (2001), incorporated herein by reference). In addition, since the marker is typically under the control of the same promoter as the antigen-specific polynucleotide, the expression of an antigen specific polypeptide can be monitored indirectly by observing the marker. For example, in a therapeutic context, T cells or B cells created by the disclosed methods can be identified and their longevity monitored by examining a patient's cells, such as cells in the blood or lymphatic system, for the presence of the marker protein. The marker may also be used to isolate immune cells created by the disclosed methods, for example for subsequent in vitro expansion.

The polynucleotide delivery system may also comprise a polynucleotide that encodes a polypeptide that may be used as a "switch" to disable or destroy cells transfected with the antigen specific polynucleotide in a heterogeneous population, for example for safety reasons. Such systems are well known in the art (see, for example, Springer et al. J. Clin. Invest. 105:1161-67 (2000); Fillat et al. Curr. Gene Ther. 3:13-26 (2003); and Denny et al. J. Biomed. Biotech. 2003: 48-70 (2003), herein incorporated by reference in their entirety. In one such embodiment, the gene of interest is a thymidine kinase gene (TK) the expression of which renders a target cell susceptible to the action of the drug gancyclovir.

In preferred embodiments, particularly in the therapeutic context, one or more genes that enhance immune cell function are co-transfected and preferably co-expressed with the antigen-specific polypeptide. For example, and without limitation, expression of a gene may enhance immune cell function by sensitizing immune cells to antigen stimulation. By linking expression of a gene that enhances immune cell function with expression of the antigen-specific polypeptide, the gene is expressed only in the mono-specific sub-population of immune cells that results from expression of the antigen specific polypeptide.

As discussed in more detail below, the activity of the gene that enhances immune cell function is not limited in any way. For example, and without limitation, the gene may encode a receptor or other signaling molecules that mediate immune cell sensitivity, or the gene may encode a molecule that down-regulates negative regulators of immune cell sensitivity. By enhancing the immune response of a mono-specific population of T cells that has been generated for therapeutic purposes, tolerance or loss of reactivity to antigen, as has been observed in native T cells, is minimized or avoided. If desired, a mono-specific population of immune cells with reduced reactivity or function can be produced by including a gene that reduces the immune response rather than a gene that enhances the immune response.

Preferably, the gene that enhances the immune cell function is under the control of the same promoter as the antigen-specific polypeptide. It is also preferably linked to an IRES or 2A element to facilitate co-expression. In this way, expression in the mono-specific sub-population of immune cells with the predetermined antigen-specificity is achieved. Expression of the immune response enhancing gene only in the specific sub-population of cells that has the desired antigen specificity avoids problems that may arise from general enhancement of the immune response in all immune cells, such as the development of autoimmunity.

A wide variety of genes can be included to enhance the function of the mono-specific immune cells that are generated. See, for example, Sadelain M. et al. *Nature Reviews Cancer* 3:35-45 (2003); Kowalczyk et al. *Acta Biochimica Polonica* 50:613-624 (2003); Tong et al. *Cancer Gene Therapy* 10:1-13 (2003); Fanning et al. *The Journal of Gene Medicine* 5:645-653 (2003); Tarner et al. *Ann. NY Acad. Sci.* 998:512-519 (2003); Robbins et al. *Gene Therapy* 10:902-911 (2003); Rondon et al. *Ann. Rev. Microbiol.* 51:257-283 (1997); Jacques et al. *Nature* 418:435-438 (2000); Qin et al. *Proc. Natl. Acad. Sci. USA* 100:183-188 (2003), each of which is incorporated herein by reference in its entirety.

In some embodiments, genes that encode an immunomodulatory protein that enhances the immune response are used. For example, genes that encode cytokines produced by T cells may be included to enhance the immune response. These include, for example, IL-2, IL-4, IL-7, IL-12, IFN-a, IFN-b, IFN-r, GM-CSF, and multi-cytokines. Genes that encode cytokine receptors that are expressed on T cell surfaces and sensitize them to stimulation may also be used, such as IL-2R, CD25, IL-4R, IL-7R, IL-15R. Members of the TNF/TNFR family may be included to enhance the immune response, such as TNF. Sadelain M. et al. *Nature Reviews Cancer* 3:35-45 (2003) and Kowalczyk et al. *Acta Biochimica Polonica* 50:613-624 (2003), incorporated herein by reference. Chimeric molecules that provide co-stimulation may also be included, such as chimeric CD28 receptors. Examples include scFv-CD28 chimeras, scFv-CD28-CD3 chimeras, or scFv-CD28-CD3-LCK fusion receptors (Geiger et al. *Blood* 98:2364-2371 (2001), incorporated herein by reference). Another gene that may be included to enhance the immune response is the gene encoding CD40L (CD154) (Tong et al. *Cancer Gene Therapy* 10:1-13 (2003), incorporated herein by reference).

In addition, the immune response may be enhanced by including genes that encode the signaling molecules that activate T cells, enhance T cell survival or enhance T cell memory. These include molecules in the JAK-STAT pathway, RAS-Raf-MAPk, and the Calmodulin-Calcium pathways.

Alternatively, as mentioned above the gene can express a protein or RNA molecule that leads to lower expression or activity of a negative regulator of the immune response. For example, RNAi may be used to target surface suppressors, such as CTLA-4 (Santulli-Muratto et al. *Cancer Research* 63:7483-7489 (2003), incorporated herein by reference). In another example, RNAi may be used to target negative regulators involved in signaling, such as members of the SOCS family. In a further example, a dominant negative receptor of a suppressor of T cell activity may be included, such as a dominant negative TGF-β receptor (Gorelik, L. and Flavell, R. A. *Nat. Med.* 7, 1118-1122 (2001); Muraoka et al. *J. Clin. Invest.* 109:1551-1559 (2002), incorporated herein by reference).

In other embodiments genes are included that encode molecules that are desirable to help treat or control a disease. For example, immune cells that preferentially migrate to sites of inflammation may be used to deliver immunomodulatory proteins the inflamed area and thereby provide therapy. Examples of genes that may be utilized in this context include, without limitation, IL-4, IL-10, IL-12p40 and anti-TNF scFv (Tarner, *Ann. NY Acad. Sci.* 998:512-519 (2003), incorporated herein by reference). Other molecules that may be expressed in immune cells to provide therapy for inflammatory disease such as arthritis include, for example, sCD40-Ig, IL-12, IL-1Ra, type I soluble IL-1 receptor, type I and II soluble TNF receptors and TGF-β (Robbins. *Gene Therapy* 10:902-911 (2003), incorporated herein by reference).

In addition to genes that encode molecules that can be used to treat inflammation, genes that encode molecules that prevent or treat other diseases or disorders, such as infectious diseases can be utilized. For example, genes may be incorporated that treat or prevent HIV infection. Such genes include, without limitation, genes encoding chimeric antigen receptors such as chimeric CD4/CD3 receptor; genetic markers that allow for the targeting and/or killing of infected cells, such as hygromycin thymadine kinase or neomycin phosphotransferase genes; dominant negative mutants, such as RevM10; ribozymes such as hairpin ribozymes directed to the U5 region of HIV RNA or hammerhead ribozymes directed to conserved regions of HIV, such as Rz2; antisense molecules, such as antisense tat sequences; molecular decoys, such as RRE decoys; aptamers; intracellular antibodies such as anti-Tat sFv, anti-Rev sFv, anti-RT sFv, anti-IN sFv, anti-MA Fab, SFv-Nc, anti-CCR5, anti-Grb3-3 and anti-ICE; and small inhibitory RNA's (siRNA). See, Fanning et al. *The Journal of Gene Medicine* 5:645-653 (2003); Rondon, et al. *Annu. Rev. Microbiol.* 51:257-283 (1997); Jacque *Nature* 418:435-438 (2002); Qin *Proc. Natl. Acad. Sci. USA* 100:183-188 (2003), each of which is incorporated herein by reference in its entirety.

Safety

While it is preferred to include any additional genes in the same polynucleotide delivery system, in other embodiments, the additional gene or genes of interest are separately transfected into the population of target cells.

In a preferred embodiment, the polynucleotide deliver system comprises one or more vectors. The vectors in turn comprise the antigen-specific polynucleotide sequences and/or their complements, optionally associated with one or more regulatory elements that direct the expression of the coding sequences. Eukaryotic cell expression vectors are well known in the art and are available from a number of commercial sources. The choice of vector and/or expression control sequences to which the antigen-specific polynucleotide sequence is operably linked depends directly, as is well known in the art, on the functional properties desired, e.g., protein expression, and the target cell to be transformed. A preferred vector contemplated by the present invention is capable of directing the insertion of the antigen-specific polynucleotide into the host chromosome and the expression of the antigen-specific polypeptide encoded by the antigen-specific polynucleotide.

Expression control elements that may be used for regulating the expression of an operably linked antigen-specific polypeptide encoding sequence are known in the art and include, but are not limited to, inducible promoters, constitutive promoters, secretion signals, enhancers and other regulatory elements.

In one embodiment, a vector comprising an antigen-specific polynucleotide will include a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

The vectors used in the polynucleotide delivery system may include a gene for a selectable marker that is effective in a eukaryotic cell, such as a drug resistance selection marker. This gene encodes a factor necessary for the survival or growth of transformed host cells grown in a selective culture medium. Host cells not transformed with the vector containing the selection gene will not survive in the culture medium. Typical selection genes encode proteins that confer resistance to antibiotics or other toxins, e.g., ampicillin, neomycin, methotrexate, or tetracycline, complement auxotrophic deficiencies, or supply critical nutrients withheld from the media. The selectable marker can optionally be present on a separate plasmid and introduced by co-transfection.

Vectors used in the polynucleotide delivery system will usually contain a promoter that is recognized by the target cell and that is operably linked to the antigen-specific polynucleotide. A promoter is an expression control element formed by a DNA sequence that permits binding of RNA polymerase and transcription to occur. Promoters are untranslated sequences that are located upstream (5') to the start codon of a structural gene (generally within about 100 to 1000 bp) and control the transcription and translation of the antigen-specific polynucleotide sequence to which they are operably linked. Promoters may be inducible or constitutive. Inducible promoters initiate increased levels of transcription from DNA under their control in response to some change in culture conditions, such as a change in temperature.

One of skill in the art will be able to select an appropriate promoter based on the specific circumstances. Many different promoters are well known in the art, as are methods for operably linking the promoter to the antigen-specific polynucleotide. Both native promoter sequences and many heterologous promoters may be used to direct expression of the antigen-specific polypeptide. However, heterologous promoters are preferred, as they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus and Simian Virus 40 (SV40). The promoter may also be, for example, a heterologous mammalian promoter, e.g., the actin promoter or an immunoglobulin promoter, a heat-shock promoter, or the promoter normally associated with the native sequence, provided such promoters are compatible with the target cell.

When the vector comprises two or more sequences from which expression is desired, each additional sequence beyond the first is preferably linked to an element that facilitates co-expression, such as an internal ribosomal entry sequence (IRES) element (U.S. Pat. No. 4,937,190), or a 2A element. For example, IRES or 2A elements are preferably used when a single vector comprises sequences encoding each chain of a multi-subunit receptor. In the case of a receptor comprising an $\alpha$ and $\beta$ chain, for example, the first coding region (encoding either the or $\beta$ chain) is located downstream from the promoter. The second coding region (encoding the remaining chain) is located downstream from the first coding region and an IRES or 2A element is disposed between the coding regions, preferably immediately preceding the second coding region. A similar arrangement can be used to co-express the heavy and light chains of an immunoglobulin with a desired specificity. In other embodiments, an IRES or 2A element is used to co-express an antigen specific polynucleotide sequence with an unrelated gene, such as a reporter gene or a gene that enhances immune cell function as described above.

In some embodiments, the vector construct comprises sequences encoding each component of a multimeric protein, for example, the alpha and beta chains of a T cell receptor, or heavy and light chains of an immunoglobulin, under a single promoter. The incorporation of an IRES or 2A element between the sequences of a first and second gene (encoding the alpha and beta chains, respectively) allows for both chains to be expressed from the same promoter at about the same level in the target cell. Approximately equivalent expression promotes differentiation of the target cell into a functional T cell (or other immune cell type, depending on the antigen-specific polypeptide).

Examples of IRES sequences that can be used include, without limitation, the IRES elements of encephalomyelitis virus (EMCV), foot-and-mouth disease virus (FMDV), Theiler's murine encephalomyelitis virus (TMEV), human rhinovirus (HRV), coxsackievirus (CSV), poliovirus (POLIO), Hepatitis A virus (HAV), Hepatitis C virus (HCV), and Pestiviruses (such as hog cholera virus (HoCV) and bovine viral diarrhea virus (BVDV)) (Le et al. *Virus Genes* 12(2): 135-147 (1996); and Le et al. *Nuc. Acids Res.* 25: 362-369 (1997), incorporated herein by reference in their entirety). In a preferred embodiment the EMCV IRES element is used.

Examples of 2A sequences that can be used include, without limitation, the 2A elements shown in SEQ ID NOS. 6-9, and illustrated in FIG. 13B.

Transcription may be increased by inserting an enhancer sequence into the vector. Enhancers are cis-acting elements of DNA, usually about 10 to 300 bp in length, that act on a promoter to increase its transcription. Many enhancer sequences are now known from mammalian genes (globin, elastase, albumin, α-fetoprotein, and insulin). Preferably an enhancer from a eukaryotic cell virus will be used. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors used in target cells will also contain sequences necessary for the termination of transcription and for stabilizing the mRNA. These sequences are often found in the 5' and, occasionally 3', untranslated regions of eukaryotic or viral DNAs or cDNAs and are well known in the art.

Plasmid vectors containing one or more of the components described above are readily constructed using standard techniques well known in the art.

For analysis to confirm correct sequences in plasmids constructed, the plasmid may be replicated in *E. coli*, purified, and analyzed by restriction endonuclease digestion, and/or sequenced by conventional methods.

Vectors that provide for transient expression in mammalian cells of an antigen-specific polynucleotide may also be used. Transient expression involves the use of an expression vector that is able to replicate efficiently in a host cell, such that the host cell accumulates many copies of the expression vector and, in turn, synthesizes high levels of a the polypeptide encoded by the antigen-specific polynucleotide in the expression vector. Sambrook et al., supra, pp. 16.17-16.22.

Other vectors and methods suitable for adaptation to the expression of antigen-specific polypeptides are well known in the art and are readily adapted to the specific circumstances.

Using the teachings provided herein, one of skill in the art will recognize that the efficacy of a particular delivery system can be tested by transforming primary bone marrow cells with a vector comprising a gene encoding a reporter protein and measuring the expression using a suitable technique, for example, measuring fluorescence from a green fluorescent protein conjugate. Suitable reporter genes are well known in the art.

Transformation of appropriate cells with vectors of the present invention is accomplished by well-known methods, and the method to be used is not limited in any way. A number of non-viral delivery systems are known in the art, including for example, electroporation, lipid-based delivery systems including liposomes, delivery of "naked" DNA, and delivery using polycyclodextrin compounds, such as those described in Schatzlein AG. 2001. Non-Viral Vectors in Cancer Gene Therapy: Principles and Progresses. *Anticancer Drugs*. Cationic lipid or salt treatment methods are typically employed, see, for example, Graham et al. *Virol.* 52:456, (1973); Wigler et al. *Proc. Natl. Acad. Sci. USA* 76:1373-76, (1979). The calcium phosphate precipitation method is preferred. However, other methods for introducing the vector into cells may also be used, including nuclear microinjection and bacterial protoplast fusion.

The polynucleotide delivery system may be viral. In one embodiment, the polynucleotide delivery system comprises a viral vector, for example, a vector derived from the MSCV virus. In a preferred embodiment the polynucleotide delivery system comprises a retroviral vector, more preferably a lentiviral vector.

Preferred vectors for use in the methods of the present invention are viral vectors. There are a large number of available viral vectors that are suitable for use with the invention, including those identified for human gene therapy applications, such as those described in Pfeifer A, Verma I M. 2001. Gene Therapy: promises and problems. *Annu. Rev. Genomics Hum. Genet.* 2:177-211. Suitable viral vectors include vectors based on RNA viruses, such as retrovirus-derived vectors, e.g., Moloney murine leukemia virus (MLV)-derived vectors, and include more complex retrovirus-derived vectors, e.g., Lentivirus-derived vectors. Human Immunodeficiency virus (HIV-1)-derived vectors belong to this category. Other examples include lentivirus vectors derived from HIV-2, feline immunodeficiency virus (FIV), equine infectious anemia virus, simian immunodeficiency virus (SIV) and maedi/visna virus.

In one embodiment, a modified retrovirus is used to deliver the antigen-specific polynucleotide to the target cell. The antigen-specific polynucleotide and any associated genetic elements are thus integrated into the genome of the host cell as a provirus.

The modified retrovirus is preferably produced in a packaging cell from a viral vector that comprises the sequences necessary for production of the virus as well as the antigen-specific polynucleotide. The viral vector may also comprise genetic elements that facilitate expression of the antigen-specific polypeptide, such as promoter and enhancer sequences as discussed above. In order to prevent replication in the target cell, endogenous viral genes required for replication may be removed.

Generation of the viral vector can be accomplished using any suitable genetic engineering techniques well known in the art, including, without limitation, the standard techniques of restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

The viral vector may incorporate sequences from the genome of any known organism. The sequences may be incorporated in their native form or may be modified in any way. For example, the sequences may comprise insertions, deletions or substitutions. In a preferred embodiment the viral vector comprises an intact retroviral 5' LTR and a self-inactivating 3' LTR.

Any method known in the art may be used to produce infectious retroviral particles whose genome comprises an RNA copy of the viral vector. To this end, the viral vector is preferably introduced into a packaging cell line that packages viral genomic RNA based on the viral vector into viral particles with a desired target cell specificity. The packaging cell line provides the viral proteins that are required in trans for the packaging of the viral genomic RNA into viral particles. The packaging cell line may be any cell line that is capable of expressing retroviral proteins. Preferred packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430).

The packaging cell line may stably express the necessary viral proteins. Such a packaging cell line is described, for example, in U.S. Pat. No. 6,218,181. Alternatively a packaging cell line may be transiently transfected with plasmids comprising nucleic acid that encodes the necessary viral proteins.

Viral particles are collected and allowed to infect the target cell. Target cell specificity may be improved by pseudotyping the virus. Methods for pseudotyping are well known in the art.

In one embodiment, the recombinant retrovirus used to deliver the antigen-specific polypeptide is a modified lentivirus. As lentiviruses are able to infect both dividing and non-dividing cells, in this embodiment it is not necessary to stimulate the target cells to divide.

In another embodiment the vector is based on the murine stem cell virus (MSCV). The MSCV vector provides long-term stable expression in target cells, particularly hematopoietic precursor cells and their differentiated progeny.

The polynucleotide delivery system may also be a DNA viral vector, including, for example adenovirus-based vectors and adeno-associated virus (AAV)-based vectors. Likewise, retroviral-adenoviral vectors also can be used with the methods of the invention.

Other vectors also can be used for polynucleotide delivery including vectors derived from herpes simplex viruses (HSVs), including amplicon vectors, replication-defective HSV and attenuated HSV. [Krisky D M, Marconi P C, Oligino T J, Rouse R J, Fink D J, et al. 1998. Development of herpes simplex virus replication-defective multigene vectors for combination gene therapy applications. *Gene Ther.* 5: 1517-30]

Polynucleotide delivery systems that have recently been developed for gene therapy uses also can be used with the methods of the invention. Such vectors include those derived from baculoviruses and alpha-viruses. [Jolly D J. 1999. Emerging viral vectors. pp 209-40 in Friedmann T, ed. 1999. The development of human gene therapy. New York: Cold Spring Harbor Lab].

These and other vectors can also be used in combination to introduce one or more polynucleotides according to the invention.

Recombinant virus produced from the viral vector may be delivered to the target cells in any way that allows the virus to infect the cells. Preferably the virus is allowed to contact the cell membrane, such as by incubating the cells in medium that comprises the virus.

Target Cells

Target cells include both germline cells and cell lines and somatic cells and cell lines. Target cells can be stem cells derived from either origin. When the target cells are germline cells, the target cells are preferably selected from the group consisting of single-cell embryos and embryonic stem cells (ES). When the target cells are somatic cells, the cells include, for example, mature lymphocytes as well as hematopoietic stem cells.

A target cell may be a stem cell or stem cell line, including without limitation heterogeneous populations of cells that contain stem cells.

Preferably, the target cells are hematopoietic stem cells. In one embodiment, the target cells are primary bone marrow cells.

Target cells can be derived from any mammalian organism including without limitation, humans, pigs, cows, horses, sheep, goats, rats, mice, rabbits, dogs, cats and guinea pigs. Target cells may be obtained by any method known in the art.

Target cells may be contacted with the polynucleotide delivery system either in vivo or in vitro. Preferably, target cells are maintained in culture and are contacted with the polynucleotide delivery system in vitro. Methods for culturing cells are well known in the art.

Depending on the polynucleotide delivery system that is to be used, target cell division may be required for transformation. Target cells can be stimulated to divide in vitro by any method known in the art. For example, hematopoietic stem cells can be cultured in the presence of one or more growth factors, such as IL-3, IL-6 and/or stem cell factor (SCF).

Transgenic Animals

Transgenic animals comprising cells that express a particular antigen-specific polypeptide are also included in the invention. An antigen-specific polynucleotide encoding the antigen-specific polypeptide of interest may be integrated either at a locus of a genome where that particular nucleic acid sequence is not otherwise normally found or at the normal locus for the transgene. The transgene may comprise nucleic acid sequences derived from the genome of the same species or of a different species than the species of the target animal.

The antigen-specific polypeptide may be foreign to the species of animal to which the recipient belongs, foreign only to the particular individual recipient, or may comprise genetic information already possessed by the recipient. In the last case, the altered or introduced gene may be expressed differently than the native gene.

While mice and rats remain the animals of choice for most transgenic experimentation, in some instances it is preferable or even necessary to use alternative animal species. Transgenic procedures have been successfully utilized in a variety of non-murine mammals, including sheep, goats, pigs, dogs, cats, monkeys, chimpanzees, hamsters, rabbits, cows and guinea pigs (see, e.g., Kim et al. *Mol. Reprod. Dev.* 46 (4): 515-526 (1997); Houdebine *Reprod. Nutr. Dev.* 35 (6):609-617 (1995); Petters *Reprod. Fertil. Dev.* 6 (5):643-645 (1994); Schnieke et al. *Science* 278 (5346):2130-2133 (1997); and Amoah J. Animal *Science* 75 (2):578-585 (1997)).

Transgenic animals can be produced by a variety of different methods including transfection, electroporation, microinjection, gene targeting in embryonic stem cells and recombinant viral and retroviral infection (see, e.g., U.S. Pat. No. 4,736,866; U.S. Pat. No. 5,602,307; Mullins et al. *Hypertension* 22 (4):630-633 (1993); Brenin et al. *Surg. Oncol.* 6 (2) 99-110 (1997); Tuan (ed.), *Recombinant Gene Expression Protocols, Methods in Molecular Biology No. 62*, Humana Press (1997)). Detailed procedures for producing transgenic animals are readily available to one skilled in the art, including the disclosures in U.S. Pat. No. 5,489,743, U.S. Pat. No. 5,602,307 and Lois et al. *Science* 295(5556):868-872 (2002)).

In one embodiment, a transgenic mammal is produced comprising cells that express a desired antigen-specific polypeptide. The transgenic mammal preferably comprises lymphocytes that express a desired antigen-specific polypeptide, such as a T cell receptor, B cell receptor, or antibody. The mammal may be produced in such a way that substantially all of the lymphocytes express the desired antigen-specific polypeptide. Thus, in one embodiment the transgenic mammal is produced by a method comprising contacting an embryonic stem cell with a polynucleotide delivery system that comprises an antigen-specific polynucleotide encoding the desired antigen-specific polypeptide. Preferably the polynucleotide delivery system comprises a retroviral vector, more preferably a lentiviral vector.

Alternatively, the transgenic mammal may be produced in such a way that only a sub-population of lymphocytes expresses the desired antigen-specific polypeptide, for example a T cell receptor. Preferably this sub-population of cells has a unique antigen specificity, and does not express any other antigen-specific polypeptides that are capable of inducing an immune response. In particular, the lymphocytes preferably do not express any other T cell receptors. In one embodiment, such mammals are produced by contacting hematopoietic stem cells with a polynucleotide delivery system comprising an antigen-specific polynucleotide encoding the desired antigen-specific polypeptide. The hematopoietic stem cells are then transferred into a mammal where they mature into lymphocytes with a unique antigen specificity.

Therapy

The methods of the present invention can be used to prevent or treat a disease or disorder for which an associated antigen can be identified. Diseases or disorders that are amenable to treatment or prevention by the methods of the present invention include, without limitation, cancers, autoimmune diseases, and infections, including viral, bacterial, fungal and parasitic infections.

In one embodiment a mammal is already suffering from a disease or disorder that is to be treated. An antigen that is associated with the disease or disorder is identified. The antigen may be previously known to be associated with the disease or disorder, or may be identified by any method known in the art. An antigen-specific polypeptide that recognizes the antigen is then identified. If an antigen-specific polypeptide for the identified antigen is not already known, it may be identified by any method known in the art, as discussed above. Preferably the antigen-specific polypeptide is a T cell receptor.

Target cells are contacted with a polynucleotide delivery system comprising an antigen-specific polynucleotide that encodes the desired antigen-specific polypeptide. Preferably the antigen-specific polynucleotide is a cDNA that encodes the antigen-specific polypeptide. The polynucleotide delivery system preferably comprises a modified lentivirus that is able to infect non-dividing cells, thus avoiding the need for in vitro propagation of the target cells. In a preferred embodiment the antigen-specific polynucleotide also comprises a gene that will enhance the therapeutic activity of the resulting population of immune cells.

The target cells preferably comprise hematopoietic stem cells, more preferably bone marrow stem cells. The target cells are preferably obtained from the mammal to be treated, although they may also be obtained from a donor. Methods for obtaining bone marrow stem cells are well known in the art.

Following transfection of the target cells with the antigen-specific polynucleotide, the target cells are reconstituted in the mammal according to any method known in the art. In the mammal, the target cells produce offspring that mature into functional antigen-specific immune cells. Because the gene encoding the antigen-specific polypeptide is incorporated into the genome of a stem cell, the patient will continue to produce the desired antigen-specific immune cells. The resulting mono-specific population of immune cells are stimulated to expand by contact with antigen. While expansion will follow from contact with the antigen associated with the disease or disorder, expansion may be facilitated or enhanced, such as by injecting the mammal with purified antigen.

In another embodiment, a disease or disorder is prevented from developing in a mammal. An antigen is identified that is associated with the disease or disorder that is expected to develop. For example, if the disease or disorder is an infection, an antigen is identified that is associated with the infectious agent. Antigens for many diseases and disorders are well known in the art. A population of immune cells that are specific for the antigen are then produced in the patient as described above. Again, because the gene encoding the polynucleotide delivery system is incorporated into the genome of the mammal, immune cells that are targeted to the infectious agent are constantly being produced, providing lifelong protection against the infectious agent.

In one embodiment, a mammal has been or is expected to be exposed to an infectious agent, such as an infectious bacteria or virus, for example HIV. An antigen present on the infectious agent is identified. A polynucleotide that encodes an antigen-specific polypeptide, preferably a T cell receptor that is specific for that antigen, is cloned. Hematopoietic stem cells, preferably bone marrow stem cells, are contacted with a modified retrovirus that comprises the antigen-specific polynucleotide and preferably comprises a gene that enhances the therapeutic activity of the resultant immune cells. Preferably the stem cells are obtained from the individual that is expected to be exposed to the infectious agent. Alternatively, they are obtained from another mammal, preferably an immunologically compatible donor. The transfected cells are then transferred into the individual where they develop into mature T cells that are capable of generating an immune response when presented with the antigen from the infectious agent. In a preferred embodiment the modified retrovirus also comprises a gene that enhances immune cell function. As a result, the gene is expressed in the mature antigen-specific T cells where it enhances their therapeutic efficacy.

In another embodiment the methods of the present invention are used to treat a patient suffering from cancer. An antigen associated with the cancer is identified and an antigen-specific polypeptide that recognizes the antigen is obtained. Preferably the antigen-specific polypeptide is a T cell receptor. In other embodiments, the antigen-specific polypeptide is a B cell receptor or an antibody. An antigen-specific polynucleotide that encodes the antigen-specific polypeptide is cloned. Target cells, preferably hematopoietic stem cells, more preferably primary bone marrow cells, are obtained and contacted with a polynucleotide delivery system that comprises the antigen-specific polynucleotide. The target cells are preferably obtained from the patient, but may be obtained from another source, such as an immunologically compatible donor. The polynucleotide delivery system is preferably a modified retrovirus, more preferably a modified lentivirus. When the antigen specific polypeptide is a T cell receptor, the polynucleotide deliver system preferably comprises nucleotide sequences encoding both the a and P chains of the T cell receptor. Preferably an IRES or 2A element is disposed between the two sequences to provide approximately equivalent expression of the two chains.

The target cells are then transferred back to the patient, where they develop into cells that are capable of generating an immune response when contacted with the identified antigen. In a preferred embodiment the polynucleotide delivery system also comprises a gene that enhances immune cell function. As a result, the gene is expressed in the mature antigen-specific cells where it enhances their therapeutic efficacy.

Expansion of the mono-specific population of immune cells may be achieved in vivo by contacting the cells with antigen, such as by injecting the patient with purified antigen.

In a further embodiment the methods of the invention are used to treat a patient suffering from melanoma. Hematopoietic stem cells are isolated from a patient and treated with a vector of the invention encoding a T cell receptor or a B cell receptor having specificity for a melanoma-specific antigen. Such antigens are known in the art. See, for example, Rosenberg, S A., Nature 411:380-384 (2001), incorporated in its entirety by reference. Two exemplary vector sequences encoding melanoma specific CD8+ TCRs are provided in SEQ ID NO: 2 which encodes a T cell receptor that recognizes an epitope of gp-100 and SEQ ID NO: 3 which encodes a T cell receptor that recognizes an epitope of Mart-1. Preferred vectors also comprise a sequence encoding one or more genes whose expression enhances immune cell function. After transfection, cells are transferred back into the patient. Lymphocytes may be expanded in vivo by injecting the patient with purified antigen. Alternatively, lymphocytes may subsequently be harvested from the patient and utilized in adoptive immunotherapy as described below.

In another embodiment, the methods of the present invention are used for adoptive immunotherapy in a patient. An antigen against which an immune response is desired is identified. A T cell receptor that is specific for the antigen is then identified and a polynucleotide encoding the T cell receptor is obtained. Hematopoietic stem cells, preferably primary bone marrow cells are obtained from the patient and contacted with a polynucleotide delivery system comprising the polynucleotide that encodes the T cell receptor. The target cells are then transferred back into the patient.

After sufficient time to allow the target cells to develop into mature T cells, T lymphocytes are harvested from the patient. This may be done by any method known in the art. Preferably, lymphocytes are isolated from a heterogeneous population of cells obtained from peripheral blood. They may be isolated, for example, by gradient centrifugation, fluorescence activated cell sorting (FACS), panning on monoclonal antibody coated plates or magnetic separation techniques. Antigen specific clones are then isolated by stimulating cells, for example with antigen presenting cells or anti-CD3 monoclonal antibody, and subsequent cloning by limited dilution or other technique known in the art. Clones that are specific for the antigen of interest are identified, expanded and transferred into the patient, such as by infusion into the peripheral blood.

The therapeutic efficacy of an immune response directed against a particular antigen may be assessed in an animal model of a disease state. In one embodiment the immune response is directed against a previously identified antigen that is known to be associated with the disease state. Alternatively, a previously unknown antigen can be identified. An immune response is provided by generating lymphocytes with a unique specificity for the desired antigen.

For example, the effectiveness of developing an immune response against a known tumor-associated antigen can be tested in a mouse tumor model. In one embodiment hematopoietic stem cells are harvested from a mouse and contacted with a polynucleotide delivery system that comprises a polynucleotide that encodes a T cell receptor that is specific for the tumor associated antigen. The stem cells are then reconstituted in a mouse that has developed or will develop a tumor, where they develop into mature lymphocytes with a unique specificity for the tumor associated antigen. The progression of the tumor in the mouse can be evaluated.

In another embodiment, the effectiveness of a specific immune response in preventing the development of a disease or disorder is determined. A transgenic animal is produced that comprises immune cells that express a desired antigen-specific polypeptide. Isolated antigen is then provided to the transgenic animal, leading to the development of an immune response. The effectiveness of the immune response in preventing the development of the disease or disorder with which the antigen is associated is then measured.

There may be situations where the use of several different antigen-specific populations of T cells or B cells is more therapeutically effective than a population of immune cells with a single antigen specificity. Thus, in other embodiments the method of therapy involves the use of a number of different antigen-specific polynucleotides to produce a number of populations of T cells and/or B cells with a variety of specificities. For example, two populations of T cells could be produced, each of which is specific for a different antigen associated with the same tumor.

In the preferred embodiment, individual populations of target cells are separately transfected, each with a vector encoding an antigen-specific polypeptide with a different specificity. The separate populations of target cells can then be combined and introduced into the patient together. Alternatively, each population can be introduced into the patient separately, in which case the introduction of each population can be separated temporally if so desired.

In another embodiment a mixture of vectors encoding different antigen-specific polypeptides with distinct specificities is used to infect a single population of target cells, such as hematopoietic stem cells from a patient. The infected population of cells is subsequently administered to the patient, as described above, where they mature into functional immune cells. Although a single target cell may be infected with multiple vectors encoding different antigen-specific polypeptides, mono-specific populations of immune cells will nevertheless be produced.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, the present invention is not intended to be limited by the recitation of the preferred embodiments, but is instead to be defined by reference to the appended claims.

EXAMPLES

Experimental Methods

The following experimental methods were used for Examples 1 and 2 described below.

Mice

C57BL/6 mice were purchased from Charles River, RAG1 and IL-2 knockout mice from Jackson Laboratories. Double IL-2/RAG1 knockout mice were generated by breeding IL-2 knockout mice with RAG1 mice. All mice were housed in Caltech animal facility.

MIG-TCR Retroviruses Construction

The MIG retroviral expression vector (SEQ. ID NO: 1) was created by Dr. Luk Van Parijs (Van Parijs L. et. al, 1999, Immunity, Vol. 11, 281-288). OTII TCRα cDNA and OTII TCRβ cDNA (a gift from Drs Francis Carbone and William Heath, Melbourne, Australia) were cloned separately into the MIG vector using the unique EcoRI restriction site. Retroviruses were generated by culturing 293.T cells in a 6 cm dish till 70-80% confluence and transfecting with the following plasmids using an established calcium phosphate precipitation technique: retroviral plasmid DNA—MIG/OTII α or MIG/TCR β (10 μg) and packaging plasmid—pCLEco, (4 μg). The DNAs were mixed with 100 ul 1.25M$CaCl_2$, to which we added dd$H_2O$ to 0.5 ml, and then 0.5 ml 2×BBS (20 ml 0.5 M BES, 22.4 ml 2.5 M NaCl, 600 μl 0.5 M $NaHPO_4$ and 157 ml H$_2$O, pH 6.96) dropwise while bubbling. This mixture was placed on the 293.T cells for 8 hrs, after which the cells were cultured in growth medium. Retrovirus-containing 293.T cell supernatant was collected 48 hr and 72 hr after transfection and used for infection of bone marrow stem cells.

THZ Hybridoma Cell Line Establishment and Infection with Retroviruses

Activated mouse CD4+ T cells were fused with the BWZ hybridoma line, which contains a reporter gene (LacZ) that is expressed under the control of the nuclear factor of activated T cells (NFAT) element of the human interleukin-2 promoter (Sanderson S. et. al, 1994, Int. Immunol, 6:369-76), to generate T-cell hybridomas by standard methodology. The hybrids were cloned by limiting dilution. One specific clone was observed to lose TCR expression, while still maintaining CD3 and CD4 expression. This clone was sorted by flow cytometry three times to stabilize the TCR-CD3+CD4+ phenotype. The resulting T cell hybridoma line, THZ, contains endogenous CD3 and CD4, but does not express an endogenous TCR, so it can be used to express sMHC class II-restricted TCRs on its surface. The function of the TCRs expressed was analyzed by lacZ assay.

THZ cells were cultured at $2 \times 10^6$ cells/ml in RPMI Medium 1640 containing 10% FCS. The cells were then spin-infected with a mixture of MIG/OTII α and MIG/OTII β retroviruses in the presence of 10 μg/ml polybrene, for 1 hr 30 mins at 2,500 rpm, 30° C. After spin infections, the retroviral supernatant was removed and replaced with growth media. 72 hrs later, infected cells were stimulated with residues 323-339 of chicken ovalbumin (OVAp) in the presence of B6 spleen cells as antigen presenting cells (APC) overnight. The next day, OTII TCR response was analyzed by bulk LacZ assay (see below).

Bulk LacZ Assay

Individual cultures of THZ cells in round-bottom 96-well plates were washed once with 100 μl PBS, then lysed and exposed to the colorogenic β-galactosidase substrate Chlorophenol red β-galactoside (0.15 mM, CPRG, Calbiochem, La Jolla, Calif.) in the presence of 100 μl Z buffer (100 mM 2-mercaptoethanol, 9 mM MgCl$_2$, 0.125% NP-40 in PBS, stored at room temperature) and incubated at 37° C. overnight. The development of the colored lacZ product was assayed using a plate reader with a 570 nm filter, and a 630 nm filter for reference.

Bone Marrow (BM) Stem Cell Isolation, Infection and Transfer

RAG1 ko mice, in a wild type or IL-2 knockout background, were treated with 5-FU (5-flurouracil) by intraperitoneal injection of 250 μg 5-FU/gram mouse body weight in PBS. Bone marrow (BM) cells were harvested 5 days later from the tibia and femur of the mice and cultured for 5 days at a density of $2 \times 10^6$ cells/ml with 20 ng/ml rmIL-3, 50 ng/ml rmIL-6, and 50 ng/ml rmSCF (all from Biosource, Camarillo, Calif.) in DMEM containing 10% FCS. After 48 and 72 hr, the BM cells were spin-infected with mixture of MIG/OTII α and MIG/TCR β retroviruses and 8 μg/ml polybrene, for 1 hr 30 mins at 2,500 rpm, at 30° C. After spin infections, the retroviral supernatant was removed and replaced with growth media containing cytokines. Recipient mice of the desired genetic background (RAG mice in wt or IL-2 ko background) received a total 480 rads whole body radiation and then received $1-2 \times 10^6$ infected BM cells by tail vein injection. BM recipient mice were maintained in a sterile environment and were maintained on the mixed antibiotic TMS (Sulfamethoxazole and Trimethoprim oral suspension) (Hi-Tech Pharmacal Co., Amityville, N.Y.) for 11 weeks until analysis.

BM Transferred Mice Immunization

Ten weeks after receiving bone marrow, individual mice were immunized by intraperitoneal injection of 200 μg OVAp in 200 μl PBS, then left for 6 days till analysis.

In Vitro T Cell Stimulation and Proliferation Assay

Spleen cells were harvested and cultured at $2 \times 10^5$ cells/well in flat-bottom 96-well plates with $2 \times 10^5$ cells/well B6 spleen cells as antigen presenting cells (APC) in standard T cell medium containing OVAp at 0, 0.01, 0.1, 1, or 10 μg/ml. Three days later, culture supernatant were collected and used for IL-2 and INF-γ ELISA. $^3$H thymidine was added to the wells at a final concentration of 0.01 mCi/ml. These cells were incubated for another 24 hours, sealed and kept at –20° C. until $^3$H counting. Data was collected with a Wallac $^3$H counter.

IL-2 and INF-γ ELISA 96-well ELISA plates were coated with purified anti-mIL-2 or anti-INF γ antibody (Pharmingen, San Diego, Calif.) diluted in carbonate buffer (0.1 M sodium bicarbonate, 0.1 M sodium carbonate, pH 9.4, stored at RT) to 1 μg/ml, by adding 50 μl/well and incubating for 2 hrs at 37° C. or 4 hr at room temperature (RT) or overnight (O/N) at 4° C. The plates were then washed twice with PBS, blocked by adding 100 μl/well of dilution buffer BBS/2% BSA/0.002% azide, incubated for 30 min at 37° C. or 1 hr at RT or O/N at 4° C. Then after being washed 4 times with PBS, sample supernatants were added to the plates at final volume of 50 μl/well, incubated for 3 hrs at 37° C. or 6 hrs at RT or O/N at 4° C. The plates were then washed 4 times followed by addition of 50 μl/well of the detecting biotinylated antibody (Pharmingen, San Diego, Calif.) diluted in the dilution buffer BBS/2% BSA/0.002% azide and incubated for 45 min at RT. Next the plates were washed 6 times with PBS, 50 μl/well of the Avidin-Alkaline Phosphotase (Pharmingen, San Diego, Calif.) diluted 1:400 in the dilution buffer BBS/2% BSA/0.002% azide was added and they were incubated for 30 min at RT. Then the plates were washed 6 times with PBS. Developing solution Sigma 104 Phosphatase Substrate (Sigma, ST. Louis, Mo.) was made at 1 mg/ml in DEA buffer (24.5 mg MgCl$_2$.6H$_2$O, 48 ml diethanolamine in 400 ml dH$_2$O, pH to 9.8 with HCl, made up to 500 ml and stored in a foil wrapped bottle at RT) right before use and then added at 50 μl/well (light sensitive therefore kept foil wrapped). Data was collected with a plate reader at 405 nm.

Experimental Methods

The following experimental methods were used in Example 9 below.

Mice

C57BL/6J(B6) female mice were purchased from Charles River Breeding Laboratories, and RAG1 deficient female mice in the B6 background were purchased from The Jackson Laboratory. OT2 T cell receptor transgenic mice in B6 background were also purchased from The Jackson Laboratory and then bred into RAG1 deficient background to generate OT2/RAG1 T cell receptor transgenic mice. All mice were housed in the California Institute of Technology animal facility in accordance with institute regulations.

MOT1 and MOT 2 Retrovirus

The MOT1 and MOT2 construct was generated from the MIG retrovirus by replacing GFP with the OT1 or OT2 T cell receptor beta chain cDNA and inserting the OT1 or OT2 T cell receptor a chain cDNA in the vector upstream of the IRES (Yang L. et al. 2002. Proc. Natl. Acad. Sci. USA 99:6204-6209. The MIG retroviral expression vector is described in Van Parijs L. et. al, 1999, Immunity, 11:281-288. Retroviruses were made in HEK293.T cells and harvested 36-48 hours after transfection.

Peptides

OVA$_{257-264}$ peptide (designated as OVAp1) recognized by the OT1 T cell receptor and OVA$_{323-339}$ peptide (designated as OVAp2) recognized by the OT2 T cell receptor were all synthesized at the Cal Tech Biopolymer Synthesis Center.

Primary T Cell Infection and Stimulation

Spleen cells were harvested from B6 female mice of six to eight weeks age and activated in vitro with 0.5 µg/ml anti-CD3 and 0.5 µg/ml anti-CD28 Abs (both from Pharmingen). On day 2 of culture, cells were spin-infected with MOT1 or MOT2 retroviruses in the presence of 10 µg/ml polybrene for 90 min at 2,500 rpm at 30° C. On day 3, cells were collected for analysis. Some aliquots of the collected cell were used to assay for the expression of OT1 or OT2 T cell receptors by flow cytometry. The remaining aliquots were allowed to rest overnight with 10 ng/ml RMIL-2 (Biosource International, Camarillo, Calif.). The next day, the rested cells were tested for responsiveness to antigen stimulation. The cells infected with MOT1 retrovirus were stimulated with OVAp1 at 0 to 1 µg/ml in the presence of APCs (spleen cells of B6 female mice). The cells infected with MOT2 retrovirus were stimulated with OVAp2 at 0 to 10 µg/ml in the presence of APCs (spleen cells of B6 female mice). On day 3 of stimulation, cell cultures supernatants were collected and analyzed for IFN-γ production using ELISA.

Hematopoietic Stem Cells (HSCs) Isolation, Infection and Transfer

B6 female mice or RAG1$^{-/-}$ female mice (6-8 weeks old) were treated with 250 µg/g of body weight of 5-fluorouracil (Sigma). Five days later, bone marrow (BM) cells enriched with HSCs were harvested and cultured for 4 days in RPMI containing 10% FBS with 20 ng/ml rmIL-3, 50 ng/ml rmIL-6 and 50 ng/ml rmSCF (all from Biosource International, Camarillo, Calif.). On day 2 and 3, the cells were spin infected with MOT1 or MOT2 retroviruses supplemented with 8 µg/ml polybrene for 90 min at 2,500 rpm, 30° C. On day 4 of culture, BM cells were collected and transferred by tail vein injection into B6 female hosts or RAG1$^{-/-}$ female hosts that had received 1200 rads or 360 rads whole-body radiation. Each host received 2-3×10$^6$ infected BM cells. BM recipient mice were maintained on a mixed antibiotic sulfmethoxazole and trimethoprim oral suspension (Hi-Tech Pharmacal, Amityville, N.Y.) in a sterile environment for 6-8 weeks until analysis or usage for further experiments.

In Vitro T Cell Stimulation and Functional Assays

For antigen dose-response experiments, spleen cells from BM recipient mice were harvested and cultured at 2×10$^5$ cells/well in T cell culture medium containing OVAp1 at 0-1 µg/ml or OVAp2 at 0-10 µg/ml. Three days later, culture supernatants were collected and assayed for IL-2, IL-4 or IFN-γ production by ELISA, and proliferation was assessed by [$^3$H]thymidine incorporation.

For time course response, cells were stimulated with 0.1 µg/ml OVAp1 or 1 µg/ml OVAp2, and the culture supernatants were collected and assayed for IL-2, IL-4 or IFN-γ production by ELISA on day 1.5, day 2.5 and day 3.5. In cytokine proliferation response, cells were cultured with 10 ng/ml rmIL-2, 10 ng/ml IL-4, or 10 ng/ml rmIL-15 (BioSource International, Camarillo, Calif.) for 4 days in the absence of antigen and proliferation was assessed by [$^3$H]thymidine incorporation.

Antibodies and FACS Analysis

Fluorochrome-conjugated antibodies specific for mouse CD4, CD8, CD25, CD69, CD62L, CD44, T cell receptorVα2, and T cell receptorVβ5.1,5.2 were purchased from BD Pharmingen (San Diego, Calif.). Surface staining was performed by blocking with anti-CD16/CD32 (mouse Fc receptor, BD Pharmingen, San Diego, Calif.) followed by staining with fluorochrome-conjugated antibodies. Intracellular staining of T cell receptor was done using the Cytofix/Cytoperm™ Kit from BD Pharmingen (San Diego, Calif.). Analyses were performed on a FACScan flow cytometer.

T Cell Memory Study

Spleen and lymph node cells from BM recipient mice (B6/MOT1) were harvested and stimulated with 0.1 µg/ml OVAp1 or 1 µg/ml OVAp2 for 3 days in vitro, respectively. The cells were then collected and transferred into RAG1$^{-/-}$ hosts by tail vein injection. Each host received 20-30×10$^6$ cells (>10% were activated OT1 or OT2 T cells). Sixteen weeks later, spleen cells were harvested from the hosts and analyzed for the presence of long-lived OT1 or OT2 T cells. Memory phenotype of the OT1 or OT2 T cells was studied by FACS. Memory function was studied by antigen dosage response, antigen time-course response and cytokine proliferation response of the OT1 or OT2 T cells. For antigen dosage response, cells were stimulated with 0-1 µg/ml OVAp1 or 0-10 µg/ml OVAp2 for 3 days, and the culture supernatants were collected and assayed for IL-2, IL-4 or IFN-γ production by ELISA. Proliferation was assessed by [$^3$H]thymidine incorporation. For an antigen time-course response, cells were stimulated with 0.1 µg/ml OVAp1 or 1 µg/ml OVAp2, and the culture supernatants were collected and assayed for IL-2, IL-4 or IFN-γ production by ELISA on day 1.5, day 2.5 and day 3.5. In cytokine proliferation response, cells were cultured with 10 ng/ml rmIL-2, 10 ng/ml rmIL-4 or 10 ng/ml rmIL-15 (all from BioSource International, Camarillo, Calif.) for 4 days in the absence of antigen, and proliferation was assessed by [$^3$H]thymidine incorporation.

Tumor Challenge of Mice

The tumor cell lines EL.4 (C57BL/6, H-2b, thymoma) and E.G7 (EL.4 cells transfected with the chicken OVA cDNA) (Moore et al., 1988) were used for tumor challenge. 5×10$^6$ EL.4 or E.G7 cells were injected subcutaneously into the left flank of the mice. Tumor size was measured every other day using fine calipers (Manostat Corporation, Switzerland), and is shown as the product of the two largest perpendicular diameters a×b (mm$^2$). Mice were euthanized when the tumors reached 400 mm$^2$.

Dendritic Cell Generation, Antigen Pulsing and Mouse Immunization

Dendritic cells (DC) were generated from bone marrow cultures as described by Lutz M B et al. (Lutz et al., 1999. J. Immunol. Methods 223:77-92), with some minor modifications. Briefly, bone marrow cells were harvested from B6 female mice (6-8 weeks old) and cultured in 10 cm diameter petri dishes at 2×10$^6$ cells/dish in 10 ml R10 medium (RPMI-1640 supplemented with 100 U/ml Penicillin, 100 µg/ml Streptomycin, 2 mM L-glutamin, 50 µM 2-mercaptoethanol and 10% FBS) containing 1:30 J558L culture supernatant. J558L is a cell line transfected with the murine GM-CSF gene (Zal et al., 1994) and its culture supernatant was used as the source of GM-CSF. On day 3 another 10 ml R10 medium containing 1:30 J558L culture supernatant was added to each dish. On day 6 and day 8, half of the culture supernatant was collected and centrifuged, and the cell pellet was resuspended in 10 ml fresh R10 medium containing 1:30 J558L culture supernatant and added back into the original culture dishes. On day 9, non-adherent cells were collected and plated into new 10 cm diameter petri dishes at 4-6×10$^6$ cells/dish in 10 ml R10 medium containing 1:60 J558L culture supernatant and LPS (1 µg/ml; Sigma) to mature DCs. On day 10, non-adherent cells (usually >80% are mature DCs) were collected and washed once with IMDM/50 mM 2-mercaptoethanol and resuspended in 0.8 ml of the same medium containing 100 μg OVAp1 (or 100 μg OVAp1 plus 100 μg OVAp2). The cells were then incubated at 37° C. for 3 hours with gentle shaking every 30 min. Three hours later, the OVAp1 or OVAp1 plus 2 loaded DCs were washed twice with PBS and used to immunize mice by tail vein injection. Each mouse received about $0.5 \times 10^6$ OVAp loaded DCs.

Example 1

Figure 1A:
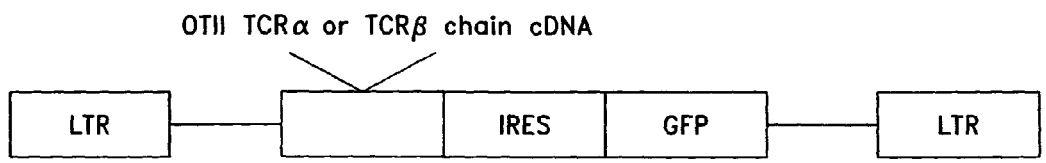
FIG. 1A schematically illustrates a retroviral vector, MIG (MSCV IRES GFP), used as a polynucleotide delivery system. The illustrated vector expresses the cDNA for the OTII TCRα or TCRβ chain. The long terminal repeat (LTR), internal ribosomal entry site (IRES) and green fluorescent protein (GFP) regions of the vector are indicated.

In Vitro Demonstration of Functional Expression of Antigen-Specific Tcrs Using Retroviral Vector This example demonstrates the successful expression of a functional TCR in a hybridoma cell line. The bicistronic MIG retroviral expression vector was created by placing GFP downstream of the pCITE1 IRES (Novagen) and cloning it into MSCV 2.2 vector (Van Parijs et al. 1999, Immunity, Vol. 11, 281-288). This retroviral vector (shown in FIG. 1A) expresses both GFP, to mark infected cells, and a heterologous gene of interest. OTII T Cell Receptor (TCR) α or β chain cDNAs were cloned into this vector. The OTII TCR is a well-defined TCR derived from a CD4+ class II-restricted T cell clone that responds to a known antigen, residues 323-339 of chicken ovalbumin (OVAp). The OTII TCR was used as a model system in our experiments. A MIG-OTI-2A vector, having the same sequence as the MIG-OTII-2A vector except for the substitution of the OTI TCR seqeuence, may be used in other embodiments. The OT I TCR is a well-defined TCR derived from a CD8+ class-I restricted T cell clone that responds to a known antigen, residues 257-264 of chicken ovalbumin.

Figure 1B:
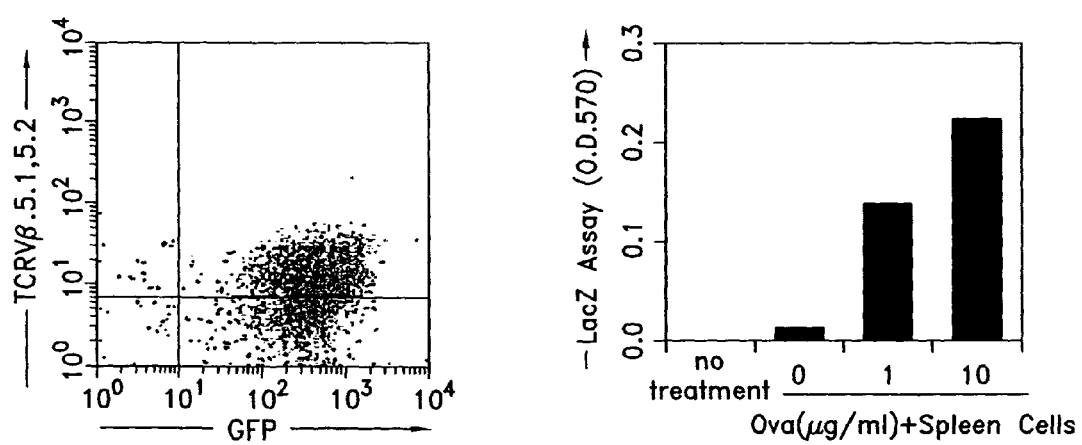
FIG. 1B illustrates surface expression of the OTII TCRβ chain in infected (GFP+) THZ cells and primary CD4+ cells. Cells were co-infected with MIG retroviruses expressing the cDNA for the OTII TCR α or β chain and then stained with a PE-conjugated antibody against TCR Vβ 5.1,5.2, which is the Vβ element used by the OTII TCRβ chain. Functional expression of the OTII TCR in THZ cells and primary CD4+ cells is also shown (right panel). Cells were co-infected with MIG retroviruses expressing OTII TCRα chain or OTII TCRβ chain and restimulated for 48 hours with OVAp in the presence of B6 spleen cells as APCs. Antigen response of THZ cells was assessed by assaying for the induction of β-galactosidase expression and by $^3$H-thymidine incorporation for primary CD4+ cells.

OTII TCRα/MIG and OTII TCRβ/MIG retroviruses were used to double-infect the THZ hybridoma cell line. This cell line has expresses endogenous CD3, so it can express TCRs on its surface. The cell line also contains a reporter gene (LacZ) that is expressed under the control of the nuclear factor of activated T cells (NFAT) element of the human interleukin-2 promoter, and can be used to assay TCR signaling. The left panel of FIG. 1B shows that infected THZ cells (identified by expression of the GFP marker gene) expressed OTII TCR on surface. The right panel of FIG. 1B shows that these cells signaled through the TCR in response to OVAp, proving that functional expression of OTII TCR was obtained using MIG retroviruses.

It was also demonstrated that a functional TCR could be expressed in primary T cells using retroviruses. Purified CD4+ T cells from wild type C57BL/6 mice were activated with an antibody to CD3ε and infected with MIG OTIIα and MIG OTIIβ viruses. The infected T cells (marked by GFP fluorescence) expressed the β chain of the OTII TCR at the cell surface and proliferated when cultured with OVAp presented by APCs (FIG. 1C).

Example 2

Generation of Functional Antigen-Specific T Cells in Mice of Defined Genetic Background FIG. 2 shows schematically the methods of the invention applied to the generation of a transgenic mouse. Bone marrow cells were obtained from mice of the desired genetic background (in these experiments, wild type or IL-2 knockout RAG1-deficient mice) and infected them with retrovirus expressing the TCR gene, as described above. The infected BM cells were then transferred into a lethally irradiated RAG1 deficient host mouse and allowed to reconstitute functionally normal T cells.

In both wild type (wt) and IL-2 knock-out (IL-2 ko) RAG1-deficient genetic backgrounds, expression of the OTII TCRα and β cDNAs in stem cells by the MIG retrovirus led to the development of phenotypically normal OT.II CD4+ T cells in the thymi of host mice. The cellularity of the thymi derived from mice expressing OTIIα and β chains was greatly increased compared to those from control mice that received bone marrow precursor cells infected with the empty MIG vector.

The upper panels of FIG. 3A show the presence of GFP+ cells in the thymus of host mice, indicating that they were derived from retrovirally-transduced RAG1 deficient wild type or IL-2 knockout stem cells. In fact, the majority (>80%) of cells in the thymi of mice receiving OTII-expressing cells were GFP positive. These thymocytes showed the expected distribution of CD4 and CD8 markers for developing class II-restricted T cells. The lower panels of FIG. 3B show that the GFP+ cells developed into mature CD4 single positive T cells.

In both wild type and IL-2 knockout RAG-1 deficient genetic backgrounds, expression of the OTII TCRα and β cDNAs in stem cells by the MIG retrovirus led to the accumulation of phenotypically normal OT.II CD4+ T cells in the peripheral lymphoid organs such as lymph nodes and the spleen. The upper panels of FIG. 3B show the presence of lymph node cells expressing GFP (GFP+) indicating that they were derived from retrovirally-transduced BM stem cells. From 30 to 60% of the cells in the lymph nodes and spleens of the mice were GFP positive. The lower panels of FIG. 3B shows that the GFP+ cells were CD4+ T cells expressing the OTII TCR. More than 80% of these cells were mature CD4+ T cells that expressed the OTII Vβ element, Vβ5. These results demonstrated that retrovirus-mediated expression of TCR cDNAs in bone marrow precursor cells could drive normal T cell development.

FIG. 3C illustrates the normal functional responses of OTII TCR transgenic CD4+ T cells obtained from the peripheral lymphoid organs of mice receiving retrovirally-transduced bone marrow stem cells.

OTII TCR transgenic CD4+ T cells in both wt and IL-2 ko genetic backgrounds showed the expected response to antigen. OT.II TCR transgenic CD4+ T cells were obtained from the spleens of BM transfer host mice and were stimulated with increasing concentrations of OVAp in vitro. The upper panels of FIG. 3C show that OTII TCR transgenic CD4+ T cells in a wt genetic background responded as expected of normal naive T cells to OVAp; they proliferated and secreted IL-2 when stimulated. The middle and lower panels of FIG. 3C show the response of OTII TCR transgenic CD4+ T cells in IL-2 ko genetic background to OVAp. As expected, these cells proliferated poorly in the absence of IL-2 and did not secrete IL-2. Addition of exogenous IL-2 stimulated proliferation in the presence of antigen.

FIG. 4A shows the normal cell expansion and expression of activation markers following in vivo antigen stimulation of OTII TCR transgenic CD4+ T cells in the peripheral lymphoid organs of mice receiving retrovirally-transduced bone marrow stem cells. Host mice that received retrovirally-transduced wild type or IL-2 knockout bone marrow stem cells show the expected expansion and activation of OTII TCR transgenic CD4+ T cells following immunization with OVAp. In both genetic backgrounds, the OTII TCR transgenic CD4+ T cells expanded and expressed activation markers that mark the transition from naive to effector T cell (CD69, CD62L and CD44). The upper panels of FIG. 4A show the expansion and induction of activation markers on OTII transgenic T cells in immunized wild type mice. The bottom panel of FIG. 4A shows the same for IL-2 knockout mice.

FIG. 4B shows the preferential expansion of GFP$^{high}$ OTII TCR transgenic CD4+ T cells following stimulation with antigen in vivo. Following immunization with OVAp a preferential expansion of GFP$^{high}$ OTII TCR transgenic CD4+ T cells was observed. Since the expression of GFP correlates with expression of TCR in this system, this result indicates that the selected T cells expressed higher amounts of the OTII TCRα and TCRβ chains. This result suggests that it is possible to select the optimal cells to respond to an immunological challenge in vivo using this gene delivery strategy.

FIG. 4C shows normal functional responses of OTII TCR transgenic CD4+ T cells following in vivo stimulation with antigen. OTII TCR transgenic CD4+ T cells that were stimulated with antigen in vivo acquired effector functions. OT.II TCR transgenic CD4+ T cells in both wt and IL-2 ko genetic backgrounds were obtained from the spleens of immunized mice. These cells were stimulated with OVAp in vitro. The upper panels of FIG. 4C shows that immunized OTII TCR transgenic CD4+ T cells in wt genetic background performed enhanced proliferation to OVAp and secreted IFNγ. These are characteristics of functional effector T cells. The middle and lower panels of FIG. 4C show the response of primed OTII TCR transgenic CD4+ T cells in IL-2 ko genetic background to OVAp, restimulated with (lower) or without (upper) exogenous IL-2. These cells show the expected dependence on IL-2 for proliferation and IFNγ production.

These results demonstrated that retrovirus-mediated expression of TCR cDNAs in bone marrow precursor cells could give rise to functionally mature T cells on different genetic backgrounds that respond normally to antigen exposure in vivo.

Example 3

Generation of Wild Type Mice Expressing Antigen-Specific TCRs

The ability to generate wild-type mice expressing antigen-specific TCRs was investigated. Bone marrow cells were obtained from wild-type B6 mice that had been previously treated with 5-fluorouracil as described above. Bone marrow cells were infected with the MIG retrovirus comprising sequences encoding the OTII TCRα and TCRβ subunits, as well as a GFP marker protein. The infected bone marrow cells were then transferred into an irradiated host animal and allowed to reconstitute functionally normal T cells.

As can be seen in FIG. 6A, approximately 65% of the cells extracted from the thymi of mice receiving infected BM cells expressed GFP. FIG. 6B shows that of the CD4+GFP+ thymocytes, about 21% expressed the OTII Vβ element. Further, the GFP positive thymocytes showed normal distribution of CD4 and CD8 markers (FIG. 6C).

In addition, infected BM cells were found to develop into mature CD4+ T cells expressing transgenic TCRs in the peripheral lymph nodes. FIG. 7A shows that approximately 44% of the cells in the peripheral lymph nodes were GFP positive. Many of the GFP positive cells were CD4+ T cells expressing OTII TCR Vβ (FIGS. 7B and 7C), indicating that retrovirus mediated expression of TCR cDNAs in wild type bone marrow precursor cells can result in normal T cell development in a host.

Example 4

In Vitro Demonstration of Functional Expression of Antigen-Specific TCRs Using Lentiviral Vector A tri-cistronic lentiviral vector was constructed based on the lentiviral vector described in (Lois et al., Science 295: 868-872 (2002); U.S. patent application Ser. No. 10/243,817, both of which are incorporated by reference in their entirety). A diagram of the vector is shown in FIG. 8. Briefly, cDNAs encoding OTII TCRα and β and GFP were cloned separately into the FUW lentiviral vector. The cDNAs were separated by internal ribosome entry site (IRES) elements (U.S. Pat. No. 4,937,190). The vector also comprised an ubiquitin promoter (Ubi) and a woodchuck hepatitis virus response element (WRE; Zufferey et al. J. Virol. 74:3668-3681 (1999); Deglon et al. Hum. Gene Ther. 11:179-190 (2000)), as indicated.

Recombinant lentivirus was generated by co-transfecting 293 cells with the lentiviral vector and packaging vectors VsVg, pRRE and pRSV rev (Yee et al. Methods Cell Biol. 43A:99-112 (1994); Dull et al. J. Virol. 72(11):8463-8471 (1998)). Retrovirus was collected and titred and used for infection of bone marrow stem cells.

The recombinant lentivirus is advantageous because it is able to infect non-dividing cells. As a result, bone marrow cells do not need to be stimulated in vitro and manipulations can be minimized.

Infection of naive T cells with the tri-cistronic recombinant lentivirus was found to mediate expression of functional OTII TCR that is able to respond to antigen challenge. As diagrammed in FIG. 9A, spleen cells were obtained from wild-type B6 mice and infected with the recombinant lentivirus. The spleen cells were then stimulated with Ova. The infected spleen cells showed proliferation in response to Ova stimulation. FACS analysis of cells after 3 days stimulation with Ova showed that the majority of the cells were GFP+ and expressed both OTII TCR α and β. The left panel of FIG. 9B shows that nearly all cells were GFP positive, indicating that they were successfully infected. The right panel of FIG. 9B indicates that greater than 90% of the cells express both OTII TCR α and β. The preferential proliferation and expansion of infected cells means that these cells responded to antigen challenge. Detection of OTII α and β expression on these cells confirmed tri-cistronic recombinant lentivirus mediated functional expression of antigen specific TCR.

Example 5

Lentivirus Infection of Fresh Isolated BM Mediated Stable Gene Transfer into Hematopoietic Stem Cells The efficiency and stability of lentiviral mediated gene transfer into freshly isolated hematopoietic stem cells was investigated. Bone marrow cells were obtained from untreated wild-type mice and infected with FUW lentivirus comprising a GFP marker gene. The infected bone marrow cells were then transferred into a wild-type host mouse that had received sub-lethal irradiation (FIG. 10), where they were allowed to develop into mature T cells. Cells in the bone marrow, thymus and peripheral lymph nodes were then extracted and analyzed for GFP expression. As shown in FIG. 11A, all three compartments comprised a significant number of cells that expressed the GFP transgene. In addition, both B cells and T cells showed expression of the transgene (FIG. 12A), indicating that the transgene was integrated into hematopoietic stem cells.

Bone marrow cells from the first host mouse were then transferred into a second host mouse (FIG. 10A). The bone marrow cells were not manipulated in any way during the transfer. As can be seen in FIG. 11B, GFP expression was maintained in the bone marrow, thymus and peripheral lymph nodes in the second host mouse. Further, GFP expression was seen in both B cells and T cells (FIG. 12B). These results indicate that the transgene was stably integrated into hematopoietic stem cells and would not be silenced by time.

Example 6

Generation of Functional T Cells

Polynucleotide delivery systems comprising cDNAs encoding the alpha and beta chains of the OTI and OTII T cell receptor were generated from the MIG vector. The sequences encoding the α and β chains of the T cell receptors in each vector were separated by an EMCV virus IRES element and expression was driven by a single promoter. These constructs were delivered into bone marrow cells from mice and the cells were transferred back into host mice, as described in Example 3. Cells were then analyzed for T cell expression. Antigen-specific cytotoxic T cells accounted for up to 20% of the total periphery CD8+ T cells, and antigen-specific helper T cells accounted for up to 10% of the total periphery CD4+ T cells.

Monospecific OVA-responding helper T cells were observed to be maintained through two generations of bone marrow transfer. Upon challenge with OVA antigen, the monospecific helper T cells activated and expanded up to 50% of the total periphery CD4+ T cells. Expression of the TCR has been observed for over 1 year in mice.

Example 7

Treatment of Cancer

Hematopoietic stem cells (HSCs), typically bone marrow cells, are isolated from a patient suffering from cancer. One or more distinct epitopes that are specific for the cancer from which the patient suffers are identified. T cell receptors that specifically bind those epitopes are identified and cloned. The HSCs are transfected with a vector encoding the alpha and beta chains of a T cell receptor that were cloned. An IRES element is disposed between the alpha and beta chains. The vector also comprises a gene that enhances immune cell function by preventing the development of tolerance. The gene sequence is preceded by an IRES sequence in the vector. Following transfection, the stem cells are transferred back into the patient, where they mature into an immune cell population that is primed against the tumor. The immune cells are caused to expand by injecting the patient with purified antigen.

Example 8

Treatment of Melanoma

Bone marrow stem cells are isolated from a patient suffering from melanoma. The cells are transfected with a vector encoding a T cell receptor that is specific to a melanoma antigen, such as the vector of SEQ ID NO: 2, which encodes a TCR specific for gp-100, or the vector of SEQ ID NO: 3, which encodes a TCR specific for the melanoma antigen Mart-1. The transfected cells are then reintroduced into the patient where they mature into functional T cells. The T cells are subsequently expanded by injecting the patient with purified antigen.

Example 9

Construction of Tricistronic Retroviruses for Directing Cell Fate

This example demonstrates the successful expression of a functional TCR in a hybridoma cell line. The tricistronic MIG retroviral expression vector was created by placing GFP downstream of the pCITE1 IRES (Novagen) and cloning it into MSCV 2.2 vector (Van Parijs et al. 1999, Immunity, Vol. 11, 281-288). This retroviral vector expresses both GFP, to mark infected cells, and a heterologous gene of interest. OTII T Cell Receptor (TCR) α and β chain cDNAs were cloned into this vector, interspersed by a foot-and-mouth disease virus 2A sequence of 11 amino acids ((shown schematically in FIG. 13A, and described in more detail below). The OTII TCR is a well-defined TCR derived from a CD4+ class II-restricted T cell clone that responds to a known antigen, residues 323-339 of chicken ovalbumin (OVAp). The OTII TCR was used as a model system in our experiments. The vector also comprises a woodchuck hepatitis virus response element (WRE; Zufferey et al. J. Virol. 74:3668-3681 (1999); Deglon et al. Hum. Gene Ther. 11: 179-190 (2000)), as indicated. The sequence of a MIG-OTII-2A (SEQ ID NO: 4) vector is shown in SEQ ID NO:4. A MIG-OTI-2A vector (SEQ ID NO: 5) may also be utilized in a similar fashion.

OTII MIG-TCR-2A retroviruses were used to infect the THZ hybridoma cell line. This cell line has expresses endogenous CD3, so it can express TCRs on its surface. FIG. 13C illustrates the MIG-TCR-2A vector-mediated co-expression of three genes: TCRα, TCRβ, and GFP. The panels of FIG. 13C show that infected THZ cells (identified by expression of the GFP marker gene) expressed OTII TCRα, TCRβ, on surface, as well as GFP.

Example 10

In Vivo Generation of Antigen-Specific B Lymphocytes by Genetic Programming of Hematopoietic Stem Cells The ability to generate antigen-specific B lymphocytes in vivo was investigated. A tricistronic retroviral vector MIG-aHEL-2A was constructed to co-express the cDNAs for an anti-HEL (hen egg lysozyme) antibody heavy and light chains, and the enhanced green fluorescent protein (shown schematically in FIG. 14A, sequence provided SEQ ID NO: 14).

FIG. 14A is a schematic representation of the tricistronic MIG-aHEL-2A viral vector co-expressing the cDNAs for the anti-HEL (hen egg lysozyme) antibody heavy and light chains, as well as EGFP. The tricistronic MIG retroviral expression vector was created by placing enhanced EGFP downstream of the pCITE1 IRES (Novagen) and cloning it into MSCV 2.2 vector (Van Parijs et al. 1999, Immunity, Vol. 11, 281-288). This retroviral vector expresses both EGFP, to, mark infected cells, and a heterologous gene of interest. The vector comprises the anti-HEL antibody heavy (μ) and light (κ) chains interspersed by a 2A sequence as described above. The vector also comprises a woodchuck hepatitis virus response element (WRE; Zufferey et al. J. Virol. 74:3668-3681 (1999); Deglon et al. Hum. Gene Ther. 11: 179-190

(2000)), as indicated. The sequence of a MIG-aHEL-2A viral vector utilized is shown as SEQ ID NO: 14.

An in vivo experiment was conducted using MIG-aHEL-2A retroviruses to transduce RAG1−/− hematopoietic stem cells (HSCs). The cells were then transferred into RAG1−/− recipients (FIG. 14B). The recipients were allowed to reconstitute their immune system for 8 weeks, and then were analyzed for B cell generation. The experimental results show that transgenic B cells were generated in bone marrow (FIG. 14C), and mature B cells were detected in the periphery (FIG. 14D).

FIG. 14B illustrates a schematic diagram of an in vivo experiment for generating antigen-specific B lymphocytes in vivo by genetic programming of hematopoietic stem cells (HSCs). HSCs are obtained from RAG1−/− mice and transduced with MIG-aHEL retroviruses (or retroviruses comprising cDNA encoding another desired antibody). The transduced cells are then transferred into RAG1−/− hosts and are allowed to reconstitute the immune system. Monospecific B cells were generated using this method.

FIG. 14C illustrates development of transgenic B cells in the bone marrow of RAG1−/− mice that received RAG1−/− HSCs transduced with MIG-aHEL-2A viruses. Eight weeks after bone marrow transplantation, bone marrow cells were collected and analyzed for B cell development. The distribution of B220 and IgMa on GFP+ and GFP− cells are shown. Bone marrow cells of anti-HEL transgenic mice and RAG1−/− mice are shown as controls.

FIG. 14D shows detection of transgenic B cells in the periphery of RAG1−/− mice that received RAG1−/− HSCs transduced with MIG-aHEL-2A viruses. Eight weeks after bone marrow transplantation, spleen and lymph node cells were collected and analyzed for the presence of mature B cells. The distribution of B220 and IgMa on GFP+ and GFP− cells are shown. Spleen and lymph node cells of anti-HEL transgenic mice and RAG1−/− mice are shown as controls.

REFERENCES

Barnden, M. J., Allison, J., Heath, W. R., and Carbone, F. R. (1998). Defective TCR expression in transgenic mice constructed using cDNA-based alpha- and beta-chain genes under the control of heterologous regulatory elements. Immunol Cell Biol 76, 34-40.

Berg, L. J., Fazekas de St Groth, B., Ivars, F., Goodnow, C. C., Gilfillan, S., Garchon, H. J., and Davis, M. M. (1988). Expression of T-cell receptor alpha-chain genes in transgenic mice. Mol Cell Biol 8, 5459-69.

Bluthmann, H., Kisielow, P., Uematsu, Y., Malissen, M., Krimpenfort, P., Berns, A., von Boehmer, H., and Steinmetz, M. (1988). T-cell-specific deletion of T-cell receptor transgenes allows functional rearrangement of endogenous alpha- and beta-genes. Nature 334, 156-9.

Clay, T. M., Custer, M. C., Sachs, J., Hwu, P., Rosenberg, S. A., and Nishimura, M. I. (1999). Efficient transfer of a tumor antigen-reactive TCR to human peripheral blood lymphocytes confers anti-tumor reactivity. J Immunol 163, 507-13.

Cooper, L. J., Kalos, M., Lewinsohn, D. A., Riddell, S. R., and Greenberg, P. D. (2000). Transfer of specificity for human immunodeficiency virus type 1 into primary human T lymphocytes by introduction of T-cell receptor genes. J Virol 74, 8207-12.

DeFelipe. Skipping the co-expression problem: the new 2A "CHYSEL" technology. Genetic Vaccines and Ther 2:13 (2004).

DeFelipe et al. Targeting of Proteins Derived from Self-Processing Polyproteins Containing Multiple Signal Sequences. Traffic 5:616-626 (2004)

Deglon et al. Hum. Gene Ther. 11:179-190 (2000)

Dembic, Z., Haas, W., Weiss, S., McCubrey, J., Kiefer, H., von Boehmer, H., and Steinmetz, M. (1986). Transfer of specificity by murine alpha and beta T-cell receptor genes. Nature 320, 232-8.

Dull et al. J. Virol. 72 (11):8463-8471 (1998)

Fanning et al. The Journal of Gene Medicine 5:645-653 (2003)

Fujio, K., Misaki, Y., Setoguchi, K., Morita, S., Kawahata, K., Kato, I., Nosaka, T., Yamamoto, K., and Kitamura, T. (2000). Functional reconstitution of class II MHC-restricted T cell immunity mediated by retroviral transfer of the alpha beta TCR complex. J Immunol 165, 528-32.

Jacques et al. Nature 418:435-438 (2000)

Kessels, H. W., Wolkers, M. C., van den Boom, M. D., van der Valk, M. A., and Schumacher, T. N. (2001). Immunotherapy through TCR gene transfer. Nat Immunol 2, 957-61.

Kouskoff, V., Signorelli, K., Benoist, C., and Mathis, D. (1995). Cassette vectors directing expression of T cell receptor genes in transgenic mice. J Immunol Methods 180, 273-80.

Kowalczyk et al. Acta Biochimica Polonica 50:613-624 (2003)

Lois et al., Science 295:868-872 (2002)

Mamalaki, C., Elliott, J., Norton, T., Yannoutsos, N., Townsend, A. R., Chandler, P., Simpson, E., and Kioussis, D. (1993). Positive and negative selection in transgenic mice expressing a T-cell receptor specific for influenza nucleoprotein and endogenous superantigen. Dev Immunol 3, 159-74.

Moss, P. A. (2001). Redirecting T cell specificity by TCR gene transfer. Nat Immunol 2, 900-1.

Pircher, H., Burki, K., Lang, R., Hengartner, H., and Zinkernagel, R. M. (1989). Tolerance induction in double specific T-cell receptor transgenic mice varies with antigen. Nature 342, 559-61.

Ponomarev et al. Neoplasia 3:480-488 (2001)

Qin et al. Proc. Natl. Acad. Sci. USA 100:183-188 (2003)

Robbins et al. Gene Therapy 10:902-911 (2003)

Rondon et al. Ann. Rev. Microbiol. 51:257-283 (1997)

Sadelain M. et al. Nature Reviews Cancer 3:35-45 (2003)

Stanislawski, T., Voss, R. H., Lotz, C., Sadovnikova, E., Willemsen, R. A., Kuball, J., Ruppert, T., Bolhuis, R. L., Melief, C. J., Huber, C., Stauss, H. J., and Theobald, M. (2001). Circumventing tolerance to a human MDM2-derived tumor antigen by TCR gene transfer. Nat Immunol 2, 962-70.

Tarner et al. Ann. NY Acad Sci. 998:512-519 (2003)

Tong et al. Cancer Gene Therapy 10:1-13 (2003)

Uematsu, Y., Ryser, S., Dembic, Z., Borgulya, P., Krimpenfort, P., Berns, A., von Boehmer, H., and Steinmetz, M. (1988). In transgenic mice the introduced functional T cell receptor beta gene prevents expression of endogenous beta genes. Cell 52, 831-41.

Yee et al. Methods Cell Biol. 43A:99-112 (1994)

Zufferey et al. J. Virol. 74:3668-3681 (1999)

What is claimed is:

1. A method of producing a population of antigen-specific T cells in a mammal comprising:
    contacting a hematopoietic stem cell ex vivo with a polynucleotide delivery system comprising an antigen-specific polynucleotide such that the antigen-specific polynucleotide is expressed in the hematopoietic stem cell and directs the differentiation of the hematopoietic stem cell into the antigen-specific T cell; and
    transferring the hematopoietic stem cell into the mammal, wherein the polynucleotide delivery system comprises a single promoter operably linked to the antigen-specific polynucleotide.

2. The method of claim 1, wherein the hematopoietic stem cell is a primary bone marrow cell.

3. The method of claim 1 wherein an IRES element or 2A element is disposed between a first and second portion of the antigen-specific polynucleotide.

4. The method of claim 3 wherein the first portion is an α subunit and the second portion is a β subunit of a T cell receptor.

5. The method of claim 1 wherein the polynucleotide delivery system comprises a modified retrovirus.

6. The method of claim 5 wherein the polynucleotide delivery system comprises a modified lentivirus.

7. The method of claim 1 wherein the polynucleotide delivery system further comprises a gene that enhances T cell function.

8. The method of claim 7 wherein the gene and the antigen-specific polynucleotide are operably linked to the single promoter.

9. The method of claim 7 wherein the gene encodes an immunomodulatory protein.

10. The method of claim 9 wherein the immunomodulatory protein is the IL2 receptor CD25.

11. The method of claim 7 wherein the gene encodes a cytokine.

12. The method of claim 11 wherein the cytokine is selected from the group consisting of IL-2, IL-4 and IFN-γ.

13. The method of claim 7 wherein the gene encodes a cytokine receptor.

14. The method of claim 13 wherein the cytokine receptor is selected from the group consisting of IL-2R, CD25, IL-4R, IL-7R and IL-15R.

15. The method of claim 1 wherein the hematopoietic stem cell is obtained from the mammal in which the T cell is to be generated.

16. The method of claim 1 wherein transferring the hematopoietic stem cell into the mammal comprises injection into the peripheral blood.

* * * * *